(12) United States Patent
Wood et al.

(10) Patent No.: US 8,399,485 B2
(45) Date of Patent: Mar. 19, 2013

(54) ACYL BIPIPERIDINYL COMPOUNDS USEFUL AS GPR 119 AGONISTS

(75) Inventors: Harold B. Wood, Westfield, NJ (US);
Alan D. Adams, Cranford, NJ (US);
Stanley Freeman, Avenel, NJ (US);
Jason W. Szewczyk, New York, NY (US); Conrad Santini, Stirling, NJ (US);
Yong Huang, Colonia, NJ (US); Ralph T. Mosley, Roselle, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 268 days.

(21) Appl. No.: 12/517,142

(22) PCT Filed: Dec. 10, 2007

(86) PCT No.: PCT/US2007/025225
§ 371 (c)(1),
(2), (4) Date: Jun. 1, 2009

(87) PCT Pub. No.: WO2008/076243
PCT Pub. Date: Jun. 26, 2008

(65) Prior Publication Data
US 2010/0075987 A1    Mar. 25, 2010

Related U.S. Application Data

(60) Provisional application No. 60/874,907, filed on Dec. 14, 2006.

(51) Int. Cl.
*A61K 31/445* (2006.01)
(52) U.S. Cl. ...... 514/316; 544/242; 546/189; 546/268.1; 548/128; 548/202; 548/262.2; 548/335.1
(58) Field of Classification Search .................. 514/316; 544/242; 546/189, 268.1; 548/128, 202, 548/262.2, 335.1
See application file for complete search history.

(56) References Cited

U.S. PATENT DOCUMENTS

| | | | |
|---|---|---|---|
| 5,364,865 A | 11/1994 | Diana | |
| 6,800,646 B1 * | 10/2004 | DeCrescenzo et al. | 514/316 |
| 2006/0154866 A1 | 7/2006 | Chu et al. | |

FOREIGN PATENT DOCUMENTS

| | | | |
|---|---|---|---|
| EP | 0 577 217 A1 | | 5/1994 |
| WO | 98/46599 | | 10/1998 |
| WO | 99/20606 | | 4/1999 |
| WO | 00/46221 | | 8/2000 |
| WO | WO 00/59498 | * | 10/2000 |
| WO | 02/50045 A1 | | 6/2002 |
| WO | 03/088962 A1 | | 10/2003 |
| WO | 2004/065380 A1 | | 8/2004 |
| WO | 2004/076413 A2 | | 9/2004 |
| WO | 2005/007647 A1 | | 1/2005 |
| WO | 2005/061489 A1 | | 7/2005 |
| WO | 2005/101989 A2 | | 11/2005 |
| WO | 2006/015259 A2 | | 2/2006 |
| WO | WO 2006/021457 | * | 2/2006 |
| WO | WO 2006/021457 | * | 3/2006 |
| WO | 2006/067531 A1 | | 6/2006 |
| WO | 2006/067532 A1 | | 6/2006 |
| WO | 2006/070208 A1 | | 7/2006 |
| WO | 2006/076231 A2 | | 7/2006 |

OTHER PUBLICATIONS

A. J. W. Orry et al., "Modeling and Docking the Endothelin G-Protein-Coupled Receptor", Biophysical Journal, vol. 79, pp. 3083-3094 (2000).
Z. Chu et al., "Agonists of the Orphan GPCR 19 AJ Promote Insulin Secretion by Stimulating Both GLP-1 Producing Endocrine Cells and Pancreatic Beta Cells", The Endocrine Society, Program & Abstracts, p. 1-19, 87th Annual Meeting, San Diego, CA (Jun. 4-7, 2005).
H. Overton et al., "Deorphanization of a G protein-coupled receptor for oleoylethanolamide and its use in the discovery of small-molecule hypophagic agents", Cell Metabolism, vol. 3, pp. 167-175 (Mar. 2006).
T. Soga et al., "Lysophosphatidylcholine enhances glucose-dependent insulin secretion via an orphan G-protein-coupled receptor", Biochemical and Biophysical Research Communications, vol. 326, pp. 744-751 (2005).

* cited by examiner

*Primary Examiner* — Douglas M Willis
(74) *Attorney, Agent, or Firm* — Anna L. Cocuzzo; John C. Todaro

(57) ABSTRACT

Bipiperidyl compounds of the formula: (I) are disclosed as useful for treating or preventing type 2 diabetes and similar conditions. Pharmaceutically acceptable salts and solvates are included as well. The compounds are useful as agonists of the g-protein coupled receptor GPR-119.

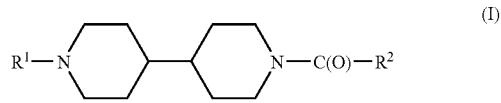

17 Claims, No Drawings

ACYL BIPIPERIDINYL COMPOUNDS USEFUL AS GPR 119 AGONISTS

CROSS-REFERENCE TO RELATED APPLICATIONS

This application is a U.S. National Phase application under 35 U.S.C. §371 of PCT Application No. PCT/US2007/025225, filed Dec. 10, 2007, which published as WO 2008/076243 on Jun. 26, 2008, and claims priority under 35 U.S.C. §119 from U.S. Provisional Application No. 60/874,907, filed Dec. 14, 2006.

BACKGROUND OF THE INVENTION

The present invention relates to G-protein coupled receptor agonists. In particular, the present invention is directed to agonists of GPR 119 that are useful for the treatment of diabetes, especially type 2 diabetes, obesity, the metabolic syndrome and related diseases and conditions.

Diabetes is a disease derived from multiple causative factors. It is characterized by elevated levels of plasma glucose (hyperglycemia) in the fasting state or after administration of glucose during an oral glucose tolerance test. There are two generally recognized forms of diabetes. In type 1 diabetes, or insulin-dependent diabetes mellitus (IDDM), patients produce little or no insulin, the hormone which regulates glucose utilization. In type 2 diabetes, or noninsulin-dependent diabetes mellitus (T2DM), insulin is still produced in the body, and patients demonstrate resistance to the effects of insulin in stimulating glucose and lipid metabolism in the main insulin-sensitive tissues, namely, muscle, liver and adipose tissue. These patients often have normal levels of insulin, and may have hyperinsulinemia (elevated plasma insulin levels), as they compensate for the reduced effectiveness of insulin by secreting increased amounts of insulin.

Insulin resistance is not primarily caused by a diminished number of insulin receptors but rather by a post-insulin receptor binding defect that is not yet completely understood. This lack of responsiveness to insulin results in insufficient insulin-mediated activation of uptake, oxidation and storage of glucose in muscle, and inadequate insulin-mediated repression of lipolysis in adipose tissue and of glucose production and secretion in the liver.

Persistent or uncontrolled hyperglycemia that occurs with diabetes is associated with increased and premature morbidity and mortality. Often abnormal glucose homeostasis is associated both directly and indirectly with obesity, hypertension, and alterations of the lipid, lipoprotein and apolipoprotein metabolism, as well as other metabolic and hemodynamic disease. Patients with type 2 diabetes mellitus have a significantly increased risk of macrovascular and microvascular complications, including atherosclerosis, coronary heart disease, stroke, peripheral vascular disease, hypertension, nephropathy, neuropathy, and retinopathy. Therefore, therapeutic control of glucose homeostasis, lipid metabolism, obesity, and hypertension are critically important in the clinical management and treatment of diabetes mellitus.

Patients who have insulin resistance often have several symptoms that together are referred to as syndrome X, or the metabolic syndrome. According to one widely used definition, a patient having metabolic syndrome is characterized as having three or more symptoms selected from the following group of five symptoms: (1) abdominal obesity; (2) hypertriglyceridemia; (3) low high-density lipoprotein cholesterol (HDL); (4) high blood pressure; and (5) elevated fasting glucose, which may be in the range characteristic of Type 2 diabetes if the patient is also diabetic. Each of these symptoms is defined clinically in the Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670. Patients with metabolic syndrome, whether or not they have or develop overt diabetes mellitus, have an increased risk of developing the macrovascular and microvascular complications that occur with type 2 diabetes, such as atherosclerosis and coronary heart disease.

Obesity, a multifactorial pathophysiological state, is characterized by excessive adiposity relative to body mass. Clinically, obesity is defined by the body mass index [BMI=weight (kg)/height (m)$^2$], corresponding to BMI values ≧30. Obesity and being overweight increases the risk of developing conditions such as high blood pressure, type 2 diabetes, heart disease, stroke, osteoarthritis, sleep apnea, gallbladder disease and cancer of the breast, prostate and colon. Higher body weights are also associated with increases in all-cause mortality.

The mainstay of treatment for obesity is an energy-limited diet and increased exercise. Guidelines for the management of obesity through such regimes have been published (e.g. Snow et al., Ann. Intern. Med. 142:525 [2005]). Although high compliance is difficult to achieve, such programs can produce an average weight loss of ~8%. A more intractable therapeutic problem appears to be weight loss maintenance. Of dieters who manage to lose 10% or more of their body mass in studies, 80-95% will regain that weight within two to five years. It appears that the homeostatic mechanisms regulating body weight are very robust, and vigorously defend against weight loss.

There are limited pharmacological therapies for the treatment of obesity. Orlistat (Xenical®), which reduces intestinal fat absorption by inhibiting pancreatic lipase, and the anorectic agent sibutramine (Reductil®, Meridia®), a central monoamine re-uptake inhibitor, are the primary agents used to treat obesity, but are associated with gastrointestinal and cardiovascular side effects, respectively, and have limited efficacy and durability in reducing body weight. Other anorectics such as phentermine, bupropion, and diethylpropion have limited use due to side effects and, many of these drugs, like sibutramine, are schedule IV controlled substances due to the risk of addiction. Recently, a CB-1 antagonist, rimonabant (Accomplia) has been launched but long term durability and efficacy remains to be determined, and the drug has CNS side effects including dysphoria.

In patients with BMI>40 who fail to achieve their weight loss goals (with or without medication) and who develop obesity-related complications, referral for bariatric surgery may be indicated, but as with other surgical procedures, there is an attendant risk of complications.

There are several available treatments for type 2 diabetes, each of which has its own limitations and potential risks. Physical exercise and a reduction in dietary intake of calories often dramatically improve the diabetic condition and are the usual recommended first-line treatment of type 2 diabetes and of pre-diabetic conditions associated with insulin resistance. Compliance with this treatment is very poor because of well-entrenched sedentary lifestyles and excess food consumption, especially of foods containing high amounts of fat and carbohydrates. Pharmacologic treatments have focused on three areas of pathophysiology: (1) Hepatic glucose production (biguanides), (2) insulin resistance (PPAR agonists), and (3) insulin secretion.

The biguanides are a class of drugs that are widely used to treat type 2 diabetes. The two best known biguanides, phenformin and metformin, cause some correction of hyperglycemia. The biguanides act primarily by inhibiting hepatic glucose production, and they also are believed to modestly improve insulin sensitivity. The biguanides can be used as monotherapy or in combination with other anti-diabetic drugs, such as insulin or an insulin secretagogues, without increasing the risk of hypoglycemia. However, phenformin and metformin can induce lactic acidosis and nausea/diarrhea. Metformin has a lower risk of side effects than phenformin and is widely prescribed for the treatment of Type 2 diabetes.

The glitazones (i.e. 5-benzylthiazolidine-2,4-diones) are a newer class of compounds that can ameliorate hyperglycemia and other symptoms of type 2 diabetes. The glitazones that are currently marketed (rosiglitazone and pioglitazone) are agonists of the peroxisome proliferator activated receptor (PPAR) gamma subtype. The PPAR-gamma agonists substantially increase insulin sensitivity in muscle, liver and adipose tissue in several animal models of type 2 diabetes, resulting in partial or complete correction of elevated plasma glucose levels without the occurrence of hypoglycemia. PPAR-gamma agonism is believed to be responsible for the improved insulin sensititization that is observed in human patients who are treated with the glitazones. New PPAR agonists are currently being developed. Many of the newer PPAR compounds are agonists of one or more of the PPAR alpha, gamma and delta subtypes. Compounds that are agonists of both the PPAR alpha and PPAR gamma subtypes (PPAR alpha/gamma dual agonists) are promising because they reduce hyperglycemia and also improve lipid metabolism. The currently marketed PPAR gamma agonists are modestly effective in reducing plasma glucose and HemoglobinAlC. The currently marketed compounds do not greatly improve lipid metabolism and may actually have a negative effect on the lipid profile. Thus, the PPAR compounds represent an important advance in diabetic therapy, but further improvements are still needed.

Another widely used drug treatment involves the administration of insulin secretagogues, such as the sulfonylureas (e.g. tolbutamide and glipizide). These drugs increase the plasma level of insulin by stimulating the pancreatic β-cells to secrete more insulin. Insulin secretion in the pancreatic β-cell is under strict regulation by glucose and an array of metabolic, neural and hormonal signals. Glucose stimulates insulin production and secretion through its metabolism to generate ATP and other signaling molecules, whereas other extracellular signals act as potentiators or inhibitors of insulin secretion through GPCR's present on the plasma membrane. Sulfonylureas and related insulin secretagogues act by blocking the ATP-dependent K+ channel in β-cells, which causes depolarization of the cell and the opening of the voltage-dependent Ca2+ channels with stimulation of insulin release. This mechanism is non-glucose dependent, and hence insulin secretion can occur regardless of the ambient glucose levels. This can cause insulin secretion even if the glucose level is low, resulting in hypoglycemia, which can be fatal in severe cases. The administration of insulin secretagogues must therefore be carefully controlled. The insulin secretagogues are often used as a first-line drug treatment for Type 2 diabetes.

There has been a renewed focus on pancreatic islet-based insulin secretion that is controlled by glucose-dependent insulin secretion. This approach has the potential for stabilization and restoration of β-cell function. In this regard, several orphan G-protein coupled receptors (GPCR's) have recently been identified that are preferentially expressed in the β-cell and are implicated in glucose dependent insulin secretion (GDIS). GPR119 is a cell-surface Gs-coupled GPCR that is highly expressed in human (and rodent) islets as well as in insulin-secreting cell lines. A naturally-occurring long-chain fatty acid amide, oleoylethanolamide (OEA) and several long chain saturated and unsaturated lysophospholipids such as 1-palmitoyl-lysophosphatidylcholine and 2-oleoyl-lysophosphatidylcholine, as well as synthetic compounds, have recently been identified as ligands for GPR119 (Overton, H. A. et al., Cell Metab. 3: 167 [2006]; Soga, T. et al., Biochem. Biophys. Res. Comm. 326: 744 [2005]). Acute administration of a synthetic small molecule GPR119 agonist to rats reduces 24 h cumulative food intake without significantly altering locomotor activity and in chronic studies, reduces cumulative food intake and body weight (Overton, H. A. et al., Cell Metab. 3: 167 [2006]) indicating that GPR119 agonists may be effective anti-obesity agents. Synthetic GPR119 agonists also augment the release of insulin from isolated static mouse islets only under conditions of elevated glucose, and improve glucose tolerance in diabetic mice and diet-induced obese (DIO) C57/B6 mice without causing hypoglycemia. GPR119 agonists therefore have the potential to function as anti-hyperglycemic agents that produce weight loss. There are several potential advantages of GPR119 as a potential target for the treatment of type 2 diabetes and obesity. First, since GPR119-mediated insulin secretion is glucose dependent, there is little or no risk of hypoglycemia. Second, the weight loss efficacy of GPR119 agonists should contribute to antihyperglycemic efficacy in diabetic and pre-diabetic obese subjects, and activation of GPR119 may allow for the simultaneous treatment of the common co-morbidities of obesity and impaired glucose tolerance/diabetes. Third, the limited tissue distribution of GPR119 in humans (mainly in islets and the GI tract) suggests that there would be less chance for side effects associated with GPR119 activity in other tissues. Fourth, GPR119 agonists may have the potential to restore or preserve islet function since GPR119 agonists reportedly increase GLP-1 levels in rodents (Chu, Z. L. et al Abstract P1-19, ENDO 2005 87th Annual Meeting, San Diego, Calif.). GLP-1 is an incretin hormone that effects GDIS and exerts anti-apoptotic and proliferative effects on islets. A protective effect on islets upon GPR119 agonism would be highly advantageous, because long term diabetes therapy often leads to the gradual diminution of islet activity, such that after extended periods of treatment with multiple oral antihyperglycemic agents, it is often necessary to treat type 2 diabetic patients with daily insulin injections. By restoring or preserving islet function, GPR119 agonists may delay or prevent the diminution and loss of islet function in a type 2 diabetic patient.

SUMMARY OF THE INVENTION

A compound represented by formula I

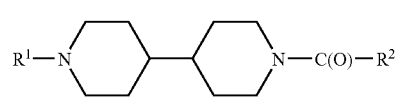

I or a pharmaceutically acceptable salt or solvate thereof wherein:

R[1] represents a 6-10 membered Aryl group or a 5-10 membered Heteroaryl group containing one or two rings, at least one nitrogen atom, 0-2 additional nitrogen atoms, and 0-1 oxygen or sulfur atom, said Aryl or Heteroaryl group being optionally substituted with 1-3 halo groups and 1-2 members selected from the group consisting of:
(1) CN or OH;
(2) $C_{1-6}$alkyl, $OC_{1-6}$alkyl or $C_{3-6}$cycloalkyl, said members being optionally substituted with 1-3 halo groups and 1-2 members selected from the group consisting of:
  i) $S(O)_xC_{1-3}$alkyl, wherein x is 0, 1 or 2 and the alkyl portion is optionally substituted with 1-3 halo atoms;
  ii) a 5-10 membered Heteroaryl moiety optionally substituted with 1-3 halo atoms or $C_{1-3}$alkyl groups;
  iii) $C_{1-3}$alkoxy or halo$C_{1-3}$alkoxy;
  iv) CN;
  v) $NH_2$, $NHC_{1-3}$alkyl and $N(C_{1-3}alkyl)_2$ the alkyl portions being optionally substituted with 1-3 halo groups;
  vi) OH;
  vii) $C(O)C_{1-6}$alkyl the alkyl portion being optionally substituted with 1-3 halo atoms;
  viii) phenyl optionally substituted with 1-2 halo atoms or $C_{1-3}$alkyl groups;
  ix) $C(O)NR^dR^e$ or $NR^dC(O)R^e$, wherein $R^d$ is selected from H and $C_{1-3}$alkyl and $R^e$ is selected from H, $C_{1-6}$alkyl, $C_{3-6}$cycloalkyl, a 5-6 membered Heteroaryl group and phenyl;
  x) $C(O)_2R^e$, wherein $R^e$ is as defined above;
  xi) Heteroaryl optionally substituted with 1-2 halo or $C_{1-3}$alkyl groups;
(3) $S(O)_xC_{1-6}$alkyl, and $SO_2NR^dR^e$ wherein the $C_{1-6}$alkyl group is optionally substituted with 1-3 halo groups and x, $R^d$ and $R^e$ are as defined above;
(4) $NH_2$, $NH(C_{1-6}alkyl)$ or $N(C_{1-6}alkyl)_2$, wherein the alkyl portions are optionally substituted with 1-3 halo groups and 1 group selected from i) through xi) above;
(5) $C(O)NR^dR^e$ or $NR^dC(O)R^e$ wherein $R^d$ and $R^e$ are as defined above;
(6) $C(O)C_{1-6}$alkyl optionally substituted with 1-3 halo atoms;
(7) $CO_2R^e$, wherein $R^e$ is as defined above;
(8) Phenyl, a 5-10 membered Heteroaryl or a 5-10 membered Heterocyclic moiety, each being optionally substituted with 1-3 halo atoms and 1-2 $C_{1-3}$ alkyl groups;
and
$R^2$ is selected from the group consisting of $C_{1-8}$alkyl, $C_{3-6}$cycloalkyl, $OC_{1-8}$alkyl and O-Phenyl, the phenyl portion of which being optionally substituted with 1-3 halo groups and 0-1 $C_{1-3}$alkyl, haloalkyl, alkoxy or haloalkoxy groups, and each of said $C_{1-8}$alkyl, $C_{3-6}$cycloalkyl and $OC_{1-8}$alkyl being optionally substituted with 1-3 halo groups, and 0-1 members selected from the group consisting of OH, oxo, CN, $OC_{1-6}$alkyl, halo$C_{1-6}$alkoxy, pyridyl, $C(O)C_{1-3}$alkyl, phenyl, and C(O)phenyl,
said phenyl, pyridyl and the phenyl portion of C(O)phenyl being optionally substituted with 1-3 halo atoms, and 1-2 $C_{1-6}$alkyl or $OC_{1-6}$alkyl groups.

DETAILED DESCRIPTION OF THE INVENTION

The invention is described herein in detail using the terms defined below unless otherwise specified.

"Alkyl", as well as other groups having the prefix "alk", such as alkoxy, and the like, means carbon chains which may be linear, branched, or cyclic, or combinations thereof, containing the indicated number of carbon atoms. If no number is specified, 1-6 carbon atoms are intended for linear and 3-7 carbon atoms for branched alkyl groups. Examples of alkyl groups include methyl, ethyl, propyl, isopropyl, butyl, sec- and tert-butyl, pentyl, hexyl, heptyl, octyl, nonyl and the like. Cycloalkyl is a subset of alkyl; if no number of atoms is specified, 3-7 carbon atoms are intended, forming 1-3 carbocyclic rings that are fused. "Cycloalkyl" also includes monocyclic rings fused to an aryl group in which the point of attachment is on the non-aromatic portion. Examples of cycloalkyl include cyclopropyl, cyclobutyl, cyclopentyl, cyclohexyl, cycloheptyl, tetrahydronaphthyl, decahydronaphthyl, indanyl and the like. Haloalkoxy and haloOalkyl are used interchangeably and refer to halo substituted alkyl groups linked through the oxygen atom. Haloalkyl and haloalkoxy include mono-substituted as well as multiple substituted alkyl and alkoxy groups, up to perhalo substituted alkyl and alkoxy. For example, trifluoromethyl and trifluoromethoxy are included.

"Aryl" (Ar) means phenyl or naphthyl, preferably phenyl.

"Heteroaryl" (HAR) unless otherwise specified, means monocyclic aromatic ring systems containing 5-6 atoms, at least one of which is a heteroatom selected from O, S, S(O), $SO_2$ and N. Examples include, but are not limited to, pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl and the like. Heteroaryl also includes such groups in charged form, e.g., pyridinium.

"Halogen" (Halo) includes fluorine, chlorine, bromine and iodine.

One aspect of the invention that is of interest relates to a compound represented by formula I

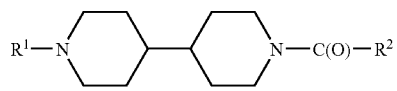

I or a pharmaceutically acceptable salt or solvate thereof wherein:
$R^1$ represents a 6-10 membered Aryl group or a 5-10 membered Heteroaryl group containing one or two rings, at least one nitrogen atom, 0-2 additional nitrogen atoms, and 0-1 oxygen or sulfur atom, said Aryl or Heteroaryl group being optionally substituted with 1-3 halo groups and 1-2 members selected from the group consisting of:
(1) CN or OH;
(2) $C_{1-6}$alkyl, $OC_{1-6}$alkyl or $C_{3-6}$cycloalkyl, said members being optionally substituted with 1-3 halo groups and 1-2 members selected from the group consisting of:
  i) $S(O)_xC_{1-3}$alkyl, wherein x is 0, 1 or 2 and the alkyl portion is optionally substituted with 1-3 halo atoms;
  ii) a 5-10 membered Heteroaryl moiety optionally substituted with 1-3 halo atoms or $C_{1-3}$ alkyl groups;
  iii) $C_{1-3}$alkoxy or halo$C_{1-3}$alkoxy;
  iv) CN;
  v) $NH_2$, $NHC_{1-3}$ alkyl and $N(C_{1-3}alkyl)_2$ the alkyl portions being optionally substituted with 1-3 halo groups;
  vi) OH;
  vii) $C(O)C_{1-6}$alkyl the alkyl portion being optionally substituted with 1-3 halo atoms;
  viii) phenyl optionally substituted with 1-2 halo atoms or $C_{1-3}$alkyl groups;
  ix) $C(O)NR^dR^e$ or $NR^dC(O)R^e$, wherein $R^d$ is selected from H and $C_{1-3}$alkyl and $R^e$ is selected from H, $C_{1-6}$alkyl, $C_{3-6}$cycloalkyl, a 5-6 membered Heteroaryl group and phenyl;
  x) $C(O)_2R^e$, wherein $R^e$ is as defined above;

xi) Heteroaryl optionally substituted with 1-2 halo or $C_{1-3}$alkyl groups;

(3) $S(O)_xC_{1-6}$alkyl, and $SO_2NR^dR^e$ wherein the $C_{1-6}$alkyl group is optionally substituted with 1-3 halo groups and x, $R^d$ and $R^e$ are as defined above;

(4) $NH_2$, $NH(C_{1-6}$alkyl) or $N(C_{1-6}$alkyl$)_2$, wherein the alkyl portions are optionally substituted with 1-3 halo groups and 1 group selected from i) through xi) above;

(5) $C(O)NR^dR^e$ or $NR^dC(O)R^e$ wherein $R^d$ and $R^e$ are as defined above;

(6) $C(O)C_{1-6}$alkyl optionally substituted with 1-3 halo atoms;

(7) $CO_2R^e$, wherein $R^e$ is as defined above;

(8) Phenyl, a 5-10 membered Heteroaryl or a 5-10 membered Heterocyclic moiety, each being optionally substituted with 1-3 halo atoms and 1-2 $C_{1-3}$ alkyl groups; and $R^2$ is selected from the group consisting of $C_{1-8}$alkyl, $C_{3-6}$cycloalkyl, $OC_{1-8}$alkyl and O-Phenyl, the phenyl portion of which being optionally substituted with 1-3 halo groups and 0-1 $C_{1-3}$ alkyl, haloalkyl, alkoxy or haloalkoxy groups, and each of said $C_{1-8}$alkyl, $C_{3-6}$cycloalkyl and $OC_{1-8}$alkyl being optionally substituted with 1-3 halo groups, and 0-1 members selected from the group consisting of OH, oxo, CN, $OC_{1-6}$alkyl, halo$C_{1-6}$alkoxy, pyridyl, $C(O)C_{1-3}$ alkyl, phenyl, and C(O)phenyl, said phenyl, pyridyl and the phenyl portion of C(O)phenyl being optionally substituted with 1-3 halo atoms, and 1-2 $C_{1-6}$alkyl or $OC_{1-6}$alkyl groups.

An aspect of the invention that is of interest relates to a compound of formula I or a pharmaceutically acceptable salt or solvate thereof wherein $R^1$ represents a 6-10 membered Aryl group, optionally substituted as described above. Within this subset of the invention, all other variables are as originally defined.

More particularly, an aspect of the invention that is of interest relates to a compound of formula I or a pharmaceutically acceptable salt or solvate thereof wherein $R^1$ represents phenyl optionally substituted as described above. Within this subset of the invention, all other variables are as originally defined.

Another aspect of the invention that is of interest relates to a compound of formula I or a pharmaceutically acceptable salt or solvate thereof wherein $R^1$ represents a 5-10 membered heteroaryl group, optionally substituted as described above. Within this subset of the invention, all other variables are as originally defined.

Another aspect of the invention that is of interest relates to a compound of formula I or a pharmaceutically acceptable salt or solvate thereof wherein $R^1$ represents a 5-10 membered heteroaryl group, selected from the group consisting of: thiazolyl, thiadiazolyl, pyridyl, pyrimidinyl, pyrazinyl and benzopyrazinyl, said heteroaryl group being optionally substituted as described above. Within this subset of the invention, all other variables are as originally defined.

More particularly, an aspect of the invention that is of interest relates to a compound of formula I or a pharmaceutically acceptable salt or solvate thereof wherein $R^1$ represents a member selected from the group consisting of phenyl, pyridyl, pyrimidinyl and pyrazinyl, said group being optionally substituted as described above. Within this subset of the invention, all other variables are as originally defined.

Even more particularly, an aspect of the invention that is of interest relates to a compound of formula I or a pharmaceutically acceptable salt or solvate thereof wherein $R^1$ represents phenyl or pyrimidinyl, said group being optionally substituted as described above. Within this subset of the invention, all other variables are as originally defined.

Another aspect of the invention that is of interest relates to a compound of formula I or a pharmaceutically acceptable salt wherein $R^1$ is described as above and is optionally substituted with 1-2 halo atoms selected from fluoro, chloro and bromo, and 1-2 members selected from the group consisting of:

(1) CN or OH;
(2) $C_{1-3}$alkyl, $OC_{1-3}$alkyl or $C_{3-6}$cycloalkyl, said members being optionally substituted with 1-3 halo atoms selected from fluoro and chloro and 1 member selected from the group consisting of:
  i) $S(O)_xC_{1-3}$ alkyl, wherein x is 0 or 2 and the alkyl portion is optionally substituted with 1-3 fluorine atoms;
  ii) a 5-10 membered Heteroaryl moiety optionally substituted with 1-3 halo atoms selected from fluorine and chlorine, or $C_{1-3}$alkyl groups;
  iii) $C_{1-3}$alkoxy or halo$C_{1-3}$alkoxy;
  iv) CN;
  v) $NH_2$, $NHC_{1-3}$alkyl and $N(C_{1-3}$alkyl$)_2$ the alkyl portions being optionally substituted with 1-3 halo groups;
  vi) OH;
  vii) $C(O)C_{1-3}$ alkyl the alkyl portion being optionally substituted with 1-3 halo atoms;
  viii) phenyl optionally substituted with 1-2 halo atoms selected from fluorine and chlorine, or $C_{1-3}$ alkyl groups;
  ix) $C(O)NR^dR^e$ or $NR^dC(O)R^e$, wherein $R^d$ is selected from H and methyl, and $R^e$ is selected from H, methyl, $C_{3-6}$cycloalkyl, phenyl and a 5-6 membered Heteroaryl group selected from thiazole, imidazole and triazole;
  x) $CO_2R^e$, wherein $R^e$ is as defined above;
  xi) Heteroaryl optionally substituted with 1-2 halo or $C_{1-3}$alkyl groups;

(3) $S(O)_xC_{1-3}$ alkyl, and $SO_2NR^dR^e$ wherein the x, $R^d$ and $R^e$ are as defined above and the $C_{1-3}$alkyl portion is optionally substituted with 1-3 halo groups selected from Cl and F;

(4) $NH_2$, $NHCH_3$ or $N(CH_3)_2$, wherein the alkyl portions are optionally substituted with 1-3 fluorine atoms;

(5) $C(O)NR^dR^e$ or $NR^dC(O)R^e$ wherein $R^d$ and $R^e$ are as defined above;

(6) $C(O)C_{1-3}$alkyl optionally substituted with 1-3 fluorine atoms;

(7) $CO_2R^e$, wherein $R^e$ is as defined above; and (8) Phenyl, a 5-10 membered Heteroaryl or a 5-10 membered Heterocyclic moiety, each being optionally substituted with 1-3 fluorine atoms and 1-2 $C_{1-3}$ alkyl groups. Within this subset of the invention, all other variables are as originally defined.

More particularly, an aspect of the invention that is of interest relates to a compound of formula I or a pharmaceutically acceptable salt wherein $R^1$ is phenyl or a 5-9 membered Heteroaryl group as described above, optionally substituted with 1-2 halo atoms selected from fluoro and chloro, and 1-2 members selected from the group consisting of:

(1) CN or OH;
(2) $CH_3$, $OCH_3$ or cyclopropyl, being optionally substituted with 1-3 halo atoms selected from fluoro and chloro and 1 member selected from the group consisting of:
  i) $SO_2C_{1-3}$alkyl, wherein the alkyl portion is optionally substituted with 1-3 fluorine atoms;
  ii) a 5-6 membered Heteroaryl moiety selected from triazole, pyrazole, thiadiazole, imidazole and oxazole, said moiety being optionally substituted with 1-2 halo atoms selected from fluorine and chlorine, or $CH_3$ groups;
  iii) $OCH_3$ or $OCF_3$;
  iv) CN;

v) $NH_2$, $NHCH_3$ and $N(CH_3)_2$ the alkyl portions of which are optionally substituted with 1-3 fluorine atoms;
vi) OH;
vii) $C(O)CH_3$ the alkyl portion being optionally substituted with 1-3 fluorine atoms;
viii) phenyl optionally substituted with 1-2 $CH_3$ groups or halo atoms selected from fluorine and chlorine;
ix) $C(O)NR^dR^e$ or $NR^dC(O)R^e$, wherein $R^d$ is selected from H and methyl, and $R^e$ is selected from H, methyl, $C_{3-6}$cycloalkyl, phenyl and a 5-6 membered Heteroaryl group selected from thiazole, imidazole and triazole;
x) $CO_2R^e$, wherein $R^e$ is as defined above;
xi) Heteroaryl optionally substituted with 1-2 halo or $C_{1-3}$alkyl groups;

(3) $S(O)_xC_{1-3}$ alkyl, and $SO_2NR^dR^e$ wherein the x, $R^d$ and $R^e$ are as defined above and the $C_{1-3}$alkyl portion is optionally substituted with 1-3 halo groups selected from Cl and F;

(4) $NH_2$, $NHCH_3$ or $N(CH_3)_2$, wherein the alkyl portions are optionally substituted with 1-3 fluorine atoms;

(5) $C(O)NR^dR^e$ or $NR^dC(O)R^e$ wherein $R^d$ and $R^e$ are as defined above;

(6) $C(O)CH_3$alkyl optionally substituted with 1-3 fluorine atoms;

(7) $CO_2R^e$, wherein $R^e$ is as defined above; and (8) Phenyl, a 5-10 membered Heteroaryl or a 5-10 membered Heterocyclic moiety, each being optionally substituted with 1-3 fluorine atoms and 1-2 $C_{1-3}$ alkyl groups. Within this subset of the invention, all other variables are as originally defined.

Another aspect of the invention that is of interest relates to a compound of formula I or a pharmaceutically acceptable salt thereof wherein:

$R^2$ is selected from the group consisting of $C_{1-7}$ alkyl, $C_{3-6}$cycloalkyl, $OC_{1-6}$alkyl and O-Phenyl, the phenyl portion of which being optionally substituted with 1-3 halo groups selected from chloro and fluoro, and 0-1 $C_{1-3}$alkyl, halo$C_{1-3}$alkyl, $C_{1-3}$alkoxy or halo$C_{1-3}$alkoxy groups, wherein the halo atoms are fluorine or chlorine, and each of said $C_{1-7}$alkyl, $C_{3-6}$cycloalkyl and $OC_{1-6}$alkyl being optionally substituted with 1-3 fluoro or chloro groups, and 0-1 members selected from the group consisting of OH, oxo, CN, $OC_{1-3}$alkyl, halo$C_{1-3}$alkoxy, $C(O)C_{1-3}$alkyl, phenyl, and $C(O)$phenyl, said phenyl and the phenyl portion of $C(O)$phenyl being optionally substituted with 1-3 chlorine or fluorine atoms, and 1-2 $C_{1-3}$alkyl or $OC_{1-3}$alkyl groups. Within this subset of the invention, all other variables are as originally defined.

Even more particularly, an aspect of the invention that is of interest relates to a compound of formula I or a pharmaceutically acceptable salt or solvate thereof wherein:

$R^2$ is selected from the group consisting of $C_{1-4}$alkyl, cyclopropyl, cyclohexyl, $OC_{1-6}$alkyl and O-Phenyl, the phenyl portion of which being optionally substituted with 1-3 halo groups selected from chloro and fluoro, and 0-1 $C_{1-3}$alkyl, halo$C_{1-3}$alkyl, $C_{1-3}$alkoxy or halo$C_{1-3}$alkoxy groups, wherein the halo atoms are fluorine or chlorine, and each of said $C_{1-4}$alkyl, cyclopropyl, cyclohexyl and $OC_{1-6}$alkyl being optionally substituted with 1-3 fluoro or chloro groups, and 0-1 members selected from the group consisting of OH, oxo, CN, $OCH_3$, $OCF_3$, $C(O)CH_3$, phenyl, and $C(O)$phenyl, said phenyl and the phenyl portion of $C(O)$phenyl being optionally substituted with 1-3 chlorine or fluorine atoms, and 1-2 $CH_3$ or $OCH_3$ groups. Within this subset of the invention, all other variables are as originally defined.

An aspect of the invention that is of more interest relates to a compound of formula I or a pharmaceutically acceptable salt or solvate thereof wherein:

$R^1$ represents a member selected from the group consisting of phenyl, pyridyl, pyrimidinyl and pyrazinyl; said group being optionally substituted with 1-2 halo atoms selected from fluoro, chloro and bromo, and 1-2 members selected from the group consisting of:

(1) CN or OH;

(2) $C_{1-3}$alkyl, $OC_{1-3}$alkyl or $C_{3-6}$cycloalkyl, said members being optionally substituted with 1-3 halo atoms selected from fluoro and chloro and 1 member selected from the group consisting of:
i) $S(O)_xC_{1-3}$alkyl, wherein x is 0 or 2 and the alkyl portion is optionally substituted with 1-3 fluorine atoms;
ii) a 5-10 membered Heteroaryl moiety optionally substituted with 1-3 halo atoms selected from fluorine and chlorine, or $C_{1-3}$alkyl groups;
iii) $C_{1-3}$alkoxy or halo$C_{1-3}$alkoxy;
iv) CN;
v) $NH_2$, $NHC_{1-3}$alkyl and $N(C_{1-3}$alkyl$)_2$ the alkyl portions being optionally substituted with 1-3 halo groups;
vi) OH;
vii) $C(O)C_{1-3}$alkyl the alkyl portion being optionally substituted with 1-3 halo atoms;
viii) phenyl optionally substituted with 1-2 halo atoms selected from fluorine and chlorine, or $C_{1-3}$alkyl groups;
ix) $C(O)NR^dR^e$ or $NR^dC(O)R^e$, wherein $R^d$ is selected from H and methyl, and $R^e$ is selected from H, methyl, $C_{3-6}$cycloalkyl, phenyl and a 5-6 membered Heteroaryl group selected from thiazole, imidazole and triazole;
x) $CO_2R^e$, wherein $R^e$ is as defined above;
xi) Heteroaryl optionally substituted with 1-2 halo or $C_{1-3}$alkyl groups;

(3) $S(O)_xC_{1-3}$alkyl, and $SO_2NR^dR^e$ wherein the x, $R^d$ and $R^e$ are as defined above and the $C_{1-3}$ alkyl portion is optionally substituted with 1-3 halo groups selected from Cl and F;

(4) $NH_2$, $NHCH_3$ or $N(CH_3)_2$, wherein the alkyl portions are optionally substituted with 1-3 fluorine atoms;

(5) $C(O)NR^dR^e$ or $NR^dC(O)R^e$ wherein $R^d$ and $R^e$ are as defined above;

(6) $C(O)C_{1-3}$alkyl optionally substituted with 1-3 fluorine atoms;

(7) $CO_2R^e$, wherein $R^e$ is as defined above; and (8) Phenyl, a 5-10 membered Heteroaryl or a 5-10 membered Heterocyclic moiety, each being optionally substituted with 1-3 fluorine atoms and 1-2 $C_{1-3}$ alkyl groups, and $R^2$ is selected from the group consisting of $C_{1-7}$alkyl, $C_{3-6}$cycloalkyl, $OC_{1-6}$alkyl and O-Phenyl, the phenyl portion of which being optionally substituted with 1-3 halo groups selected from chloro and fluoro, and 0-1 $C_{1-3}$alkyl, $C_{1-3}$alkoxy or halo$C_{1-3}$alkoxy groups, wherein the halo atoms are fluorine or chlorine, and each of said $C_{1-7}$alkyl, $C_{3-6}$cycloalkyl and $OC_{1-6}$alkyl being optionally substituted with 1-3 fluoro or chloro groups, and 0-1 members selected from the group consisting of OH, oxo, CN, $OC_{1-3}$alkyl, halo$C_{1-3}$alkoxy, $C(O)C_{1-3}$alkyl, phenyl, and $C(O)$phenyl, said phenyl and the phenyl portion of $C(O)$phenyl being optionally substituted with 1-3 chlorine or fluorine atoms, and 1-2 $C_{1-3}$alkyl or $OC_{1-3}$alkyl groups. Within this subset of the invention, all other variables are as originally defined.

More particularly, an aspect of the invention that is of increased interest relates to a compound of formula I or a pharmaceutically acceptable salt or solvate thereof wherein:

$R^1$ represents a member selected from the group consisting of phenyl, pyridyl, pyrimidinyl and pyrazinyl, optionally substituted with 1-2 halo atoms selected from fluoro and chloro, and 1-2 members selected from the group consisting of:

(1) CN or OH;

(2) CH$_3$, OCH$_3$ or cyclopropyl, being optionally substituted with 1-3 halo atoms selected from fluoro and chloro and 1 member selected from the group consisting of:
  i) SO$_2$C$_{1-3}$alkyl, wherein the alkyl portion is optionally substituted with 1-3 fluorine atoms;
  ii) a 5-6 membered Heteroaryl moiety selected from triazole, pyrazole, thiadiazole, imidazole and oxazole, said moiety being optionally substituted with 1-2 halo atoms selected from fluorine and chlorine, or CH$_3$ groups;
  iii) OCH$_3$ or OCF$_3$;
  iv) CN;
  v) NH$_2$, NHCH$_3$ and N(CH$_3$)$_2$ the alkyl portions of which are optionally substituted with 1-3 fluorine atoms;
  vi) OH;
  vii) C(O)CH$_3$ the alkyl portion being optionally substituted with 1-3 fluorine atoms;
  viii) phenyl optionally substituted with 1-2 CH$_3$ groups or halo atoms selected from fluorine and chlorine;
  ix) C(O)NR$^d$R$^e$ or NR$^d$C(O)R$^e$, wherein R$^d$ is selected from H and methyl, and R$^e$ is selected from H, methyl, C$_{3-6}$cycloalkyl, phenyl and a 5-6 membered Heteroaryl group selected from thiazole, imidazole and triazole;
  x) CO$_2$R$^e$, wherein R$^e$ is as defined above;
  xi) Heteroaryl optionally substituted with 1-2 halo or C$_{1-3}$ alkyl groups;

(3) S(O)$_x$C$_{1-3}$alkyl, and SO$_2$NR$^d$R$^e$ wherein the x, R$^d$ and R$^e$ are as defined above and the C$_{1-3}$alkyl portion is optionally substituted with 1-3 halo groups selected from Cl and F;

(4) NH$_2$, NHCH$_3$ or N(CH$_3$)$_2$, wherein the alkyl portions are optionally substituted with 1-3 fluorine atoms;

(5) C(O)NR$^d$R$^e$ or NR$^d$C(O)R$^e$ wherein R$^d$ and R$^e$ are as defined above;

(6) C(O)CH$_3$alkyl optionally substituted with 1-3 fluorine atoms;

(7) CO$_2$R$^e$, wherein R$^e$ is as defined above; and (8) Phenyl, a 5-10 membered Heteroaryl or a 5-10 membered Heterocyclic moiety, each being optionally substituted with 1-3 fluorine atoms and 1-2 C$_{1-3}$ alkyl groups, and R$^2$ is selected from the group consisting of C$_{1-4}$alkyl, cyclopropyl, cyclohexyl, OC$_{1-6}$alkyl and O-Phenyl, the phenyl portion of which being optionally substituted with 1-3 halo groups selected from chloro and fluoro, and 0-1 C$_{1-3}$alkyl, haloC$_{1-3}$alkyl, C$_{1-3}$alkoxy or haloC$_{1-3}$alkoxy groups, wherein the halo atoms are fluorine or chlorine, and each of said C$_{1-4}$alkyl, cyclopropyl, cyclohexyl and OC$_{1-6}$alkyl being optionally substituted with 1-3 fluoro or chloro groups, and 0-1 members selected from the group consisting of OH, oxo, CN, OCH$_3$, OCF$_3$, C(O)CH$_3$, phenyl, and C(O) phenyl, said phenyl and the phenyl portion of C(O)phenyl being optionally substituted with 1-3 chlorine or fluorine atoms, and 1-2 CH$_3$ or OCH$_3$ groups. Within this subset of the invention, all other variables are as originally defined.

Examples of species that fall within the present invention are found in the examples contained herein.

Utilities

Compounds of the present invention are potent agonists of the GPR119 receptor. The compounds of the invention, and pharmaceutically acceptable salts thereof are modulators of the receptor known as GPR 119, and are therefore useful in the treatment of diseases that are modulated by GPR119 ligands and agonists. Many of these diseases are summarized below.

Treatment and prevention of the following diseases and conditions are included in the present invention: Also, the compounds of the invention may be used for the manufacture of a medicament for treating one or more of these diseases or conditions:

(1) non-insulin dependent diabetes mellitus (type 2 diabetes);
(2) hyperglycemia;
(3) the metabolic syndrome;
(4) obesity;
(5) ischemia and myocardial infarction;
(6) neurological disorders such as alzheimer's disease, schizophrenia, and impaired cognition;
(5) hypercholesterolemia;
(6) hypertriglyceridemia (elevated levels of triglyceride-rich-lipoproteins);
(7) mixed or diabetic dyslipidemia;
(8) low HDL cholesterol;
(9) high LDL cholesterol;
(10) hyperapoBliproteinemia; and
(11) atherosclerosis.

More particularly, the following diseases and conditions can be treated using the compounds of formula I or a pharmaceutically acceptable salt or solvate thereof. The compounds may be used for manufacturing a medicament for the treatment or prevention of one or more of these diseases or conditions:

(1) Type 2 diabetes, and specifically hyperglycemia;
(2) Metabolic syndrome;
(3) Obesity; and
(4) Hypercholesterolemia or dyslipidemias.

Because the compounds are agonists of the GPR119 receptor, the compounds will be useful for lowering glucose, lipids, and insulin resistance in diabetic patients and in non-diabetic patients who have impaired glucose tolerance and/or are in a pre-diabetic condition. The compounds are useful to ameliorate hyperinsulinemia, which often occurs in diabetic or pre-diabetic patients, by modulating the swings in the level of serum glucose that often occurs in these patients. The compounds are useful for treating or reducing insulin resistance. The compounds are useful for treating or preventing gestational diabetes.

The compounds, compositions, and medicaments as described herein are useful for reducing the risks of adverse sequelae associated with metabolic syndrome, and in reducing the risk of developing atherosclerosis, delaying the onset of atherosclerosis, and/or reducing the risk of sequelae of atherosclerosis. Sequelae of atherosclerosis include angina, claudication, heart attack, stroke, and others.

By keeping hyperglycemia under control, the compounds are useful to delay or for preventing vascular restenosis and diabetic retinopathy.

The compounds of this invention are useful in improving or restoring β-cell function, so that they may be useful in treating type 1 diabetes or in delaying or preventing a patient with type 2 diabetes from needing insulin therapy.

The compounds may be useful for reducing appetite and body weight in obese subjects and may therefore be useful in reducing the risk of co-morbidities associated with obesity such as hypertension, atherosclerosis, diabetes, and dyslipidemia.

By elevating levels of active GLP-1 in vivo, the compounds are useful in treating neurological disorders such as Alzheimer's disease, multiple sclerosis, and schizophrenia.

The compounds generally are useful for treating the following diseases and conditions: (1) type 2 diabetes (also known as non-insulin dependent diabetes mellitus, or T2DM), (2) hyperglycemia, (3) low glucose tolerance, (4) insulin resistance, (5) obesity, (6) lipid disorders, (7) dyslipidemia, (8) hyperlipidemia, (9) hypertriglyceridemia, (10) hypercholesterolemia, (11) low HDL levels, (12) high LDL levels, (13) atherosclerosis and its sequelae, (14) vascular restenosis, (15) abdominal obesity, (16) retinopathy, (17) metabolic syndrome, (18) high blood pressure, (19) Alzheimer's disease, (20) schizophrenia, (21) multiple sclerosis, and (22) insulin resistance.

One aspect of the invention provides a method for the treatment and control of mixed or diabetic dyslipidemia, hypercholesterolemia, atherosclerosis, low HDL levels, high LDL levels, hyperlipidemia, and/or hypertriglyceridemia, which comprises administering to a patient in need of such treatment a therapeutically effective amount of a compound of formula I or a pharmaceutically acceptable salt or solvate thereof. The compound may be used alone or advantageously may be administered with a cholesterol biosynthesis inhibitor, particularly an HMG-CoA reductase inhibitor such as lovastatin, simvastatin, rosuvastatin, pravastatin, fluvastatin, atorvastatin, rivastatin, itavastatin, or ZD-4522. The compound may also be used advantageously in combination with other lipid lowering drugs such as cholesterol absorption inhibitors (for example stanol esters, sterol glycosides such as tiqueside, and azetidinones such as ezetimibe), ACAT inhibitors (such as avasimibe), CETP inhibitors (for example torcetrapib), niacin, bile acid sequestrants, microsomal triglyceride transport inhibitors, and bile acid reuptake inhibitors. These combination treatments are useful for the treatment or control of conditions selected from the group consisting of hypercholesterolemia, atherosclerosis, hyperlipidemia, hypertriglyceridemia, dyslipidemia, high LDL, and low HDL.

Another aspect of the invention provides a method for the treatment and control of obesity or metabolic syndrome, which comprises administering to a patient in need of such treatment a therapeutically effective amount of a compound having formula I or a pharmaceutically acceptable salt or solvate thereof. The compound may be used alone or advantageously may be administered with an anti-obesity agent, particularly a lipase inhibitor such as orlistat, or a monoamine neurotransmitter uptake inhibitor such as sibutramine, phentermine and the like. The compound may also be used advantageously in combination with CB-1 inverse agonists or antagonists such as rimonabant.

Administration and Dose Ranges

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of Formula I or a pharmaceutically acceptable salt or solvate thereof are administered orally.

The effective dosage of active ingredient employed may vary depending on the particular compound employed, the mode of administration, the condition being treated and the severity of the condition being treated. Such dosage may be ascertained readily by a person skilled in the art.

When treating or controlling diabetes mellitus and/or hyperglycemia or hypertriglyceridemia or other diseases for which compounds of Formula I are indicated, generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. For most large mammals, the total daily dosage is from about 1.0 milligrams to about 1000 milligrams. In the case of a 70 kg adult human, the total daily dose will generally be from about 1 milligram to about 350 milligrams. For a particularly potent compound, the dosage for an adult human may be as low as 0.1 mg. The dosage regimen may be adjusted within this range or even outside of this range to provide the optimal therapeutic response.

Oral administration will usually be carried out using tablets or capsules. Examples of doses in tablets and capsules are 0.1 mg, 0.25 mg, 0.5 mg, 1 mg, 2 mg, 5 mg, 10 mg, 25 mg, 50 mg, 100 mg, 200 mg, 350 mg, 500 mg, 700 mg, 750 mg, 800 mg and 1000 mg. Other oral forms may also have the same or similar dosages.

Pharmaceutical Compositions

Another aspect of the present invention provides pharmaceutical compositions which comprise a compound of Formula I and a pharmaceutically acceptable carrier. The pharmaceutical compositions of the present invention comprise a compound of Formula I or a pharmaceutically acceptable salt or solvate as an active ingredient, as well as a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids. A pharmaceutical composition may also comprise a prodrug, or a pharmaceutically acceptable salt thereof, if a prodrug is administered.

The compositions are typically suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the condition being treated and on the particular active ingredient selected. They may be conveniently presented in unit dosage form and prepared by any of the methods well-known in the art of pharmacy.

In practical use, the compound of Formula I, or the pharmaceutically acceptable salt or solvate thereof can be combined as the active ingredient in intimate admixture with the pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage form. Solid pharmaceutical carriers are therefore typically employed. If desired, tablets may be coated by standard aqueous or nonaqueous techniques. Such compositions and preparations typically comprise at least about 0.1 percent of active compound, the remainder of the composition being the carrier. The percentage of active compound in these compositions may, of course, be varied and is conveniently between about 2 percent to about 60 percent of the weight of the dosage form. The amount of active compound in such therapeutically useful compositions is such that an effective dosage will be delivered.

Alternatively, the active compound can be administered intranasally as, for example, in the form of liquid drops or a spray.

The tablets, capsules and the like also typically contain a binder. Examples of suitable binders include gum tragacanth, acacia, gelatin and a synthetic or semisynthetic starch derivative, such as hydroxypropylmethylcellulose (HPMC); excipients such as dicalcium phosphate; a disintegrating agent such as corn starch, potato starch, alginic acid; a lubricant such as magnesium stearate; and in some instances, a sweetening agent such as sucrose, lactose or saccharin. When the dosage form employed is a capsule, it may contain, in addition to the components described above, a liquid carrier such as a fatty oil.

Various other materials may be present as coatings or to modify the physical form of the dosage unit. For instance, tablets may be coated with shellac, sugar or both. Syrups and elixirs typically contain, in addition to the active ingredient, sucrose as a sweetening agent, methyl or propylparabens as a preservative, a dye and a flavoring such as cherry or orange flavor.

The compound of formula I or a pharmaceutically acceptable salt or solvate thereof may also be administered parenterally. Solutions or suspensions of these active compounds can be prepared in water, saline or another biocompatible vehicle, suitably mixed with a surfactant, buffer, and the like. Dispersions can also be prepared in glycerol, liquid polyethylene glycols and mixtures thereof in an oil. Under ordinary conditions of storage and use, these preparations can also contain a preservative to prevent the growth of microorganisms.

The pharmaceutical forms suitable for injectable use include sterile aqueous solutions and dispersions, and sterile powders for the extemporaneous preparation of sterile injectable solutions and dispersions. The preparation should be prepared under sterile conditions and be fluid to the extent that easy syringability exists. It should be sufficiently stable under the conditions of manufacture and storage and preserved against the growth of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and suitable oils.

Combination Therapy

Compounds of Formula I may be used in combination with other drugs that may also be useful in the treatment or amelioration of the diseases and conditions described herein. Such other drugs may be administered, by a route and in an amount commonly used therefor, contemporaneously or sequentially with a compound of Formula I or a pharmaceutically acceptable salt or solvate thereof. In the treatment of patients who have type 2 diabetes, insulin resistance, obesity, metabolic syndrome, neurological disorders, and co-morbidities that accompany these diseases, more than one drug is commonly administered. The compounds of this invention may generally be administered to a patient who is already taking one or more other drugs for these conditions.

When a compound of Formula I is used contemporaneously with one or more other drugs, a pharmaceutical composition in unit dosage form containing such other drugs and the compound of Formula I is preferred. However, the combination therapy also includes therapies in which the compound of Formula I and one or more other drugs are administered on different overlapping schedules. It is also contemplated that when used in combination with one or more other active ingredients, the compound of the present invention and the other active ingredients may be used in lower doses than when each is used singly. Accordingly, the pharmaceutical compositions of the present invention include those that contain one or more other active ingredients, in addition to a compound of Formula I.

Examples of other active ingredients that may be administered in combination with a compound of Formula I, and either administered separately or in the same pharmaceutical composition, include, but are not limited to:

(a) PPAR gamma agonists and partial agonists, including both glitazones and non-glitazones (e.g. troglitazone, pioglitazone, englitazone, MCC-555, rosiglitazone, balaglitazone, netoglitazone, T-131, LY-300512, and LY-818;

(b) biguanides such as metformin and phenformin;

(c) protein tyrosine phosphatase-1B (PTP-1B) inhibitors;

(d) dipeptidyl peptidase IV (DPP-4) inhibitors, such as sitagliptin, saxagliptin, denagliptin, SYR-322, and vildagliptin;

(e) insulin or insulin mimetics;

(f) sulfonylureas such as tolbutamide, glimepiride, glipizide, and related materials;

(g) α-glucosidase inhibitors (such as acarbose);

(h) agents which improve a patient's lipid profile, such as (i) HMG-CoA reductase inhibitors (lovastatin, simvastatin, rosuvastatin, pravastatin, fluvastatin, atorvastatin, rivastatin, itavastatin, ZD-4522 and other statins), (ii) bile acid sequestrants (cholestyramine, colestipol, and dialkylaminoalkyl derivatives of a cross-linked dextran), (iii) nicotinyl alcohol, nicotinic acid or a salt thereof, (iv) PPARα agonists such as fenofibric acid derivatives (gemfibrozil, clofibrate, fenofibrate and bezafibrate), (v) cholesterol absorption inhibitors, such as for example ezetimibe, (vi) acyl CoA:cholesterol acyltransferase (ACAT) inhibitors, such as avasimibe, (vii) CETP inhibitors, such as torcetrapib, and (viii) phenolic antioxidants, such as probucol;

(i) PPARα/γ dual agonists, such as muraglitazar, tesaglitazar, farglitazar, and JT-501;

(j) PPARδ agonists such as those disclosed in WO97/28149;

(k) antiobesity compounds such as fenfluramine, dexfenfluramine, phentiramine, subitramine, orlistat, neuropeptide Y5 inhibitors, Mc4r agonists, cannabinoid receptor 1 (CB-1) antagonists/inverse agonists, and $β_3$ adrenergic receptor agonists;

(l) ileal bile acid transporter inhibitors;

(m) agents intended for use in inflammatory conditions such as aspirin, non-steroidal anti-inflammatory drugs, glucocorticoids, azulfidine, and cyclo-oxygenase 2 selective inhibitors;

(n) glucagon receptor antagonists;

(o) GLP-1, (p) GIP-1, (q) GLP-1 analogs, such as exendins, for example exenatide (Byetta), exenatide-LAR, and liraglutide (r) Hydroxysterol dehydrogenase-1 (HSD-1) inhibitors.

The above combinations include combinations of a compound of the present invention not only with one other active compound, but also with two or more other active compounds. Non-limiting examples include combinations of compounds having Formula I or a pharmaceutically acceptable salt or solvate thereof with two or more active compounds selected from biguanides, sulfonylureas, HMG-CoA reductase inhibitors, other PPAR agonists, PTP-1B inhibitors, DPP-4 inhibitors, and anti-obesity compounds.

Another aspect of the invention that is of interest is a pharmaceutical composition comprised of a compound of formula I or a pharmaceutically acceptable salt or solvate thereof in combination with a pharmaceutically acceptable carrier.

Another aspect of the invention that is of interest relates to a method of treating hyperglycemia, diabetes or insulin resistance in a mammalian patient in need of such treatment which comprises administering to said patient a compound in accordance with formula I or a pharmaceutically acceptable salt or solvate thereof in an amount that is effective to treat hyperglycemia, diabetes or insulin resistance.

More particularly, another aspect of the invention that is of interest relates to a method of treating type 2 diabetes in a mammalian patient in need of such treatment comprising administering to the patient a compound in accordance with formula I or a pharmaceutically acceptable salt or solvate thereof in an amount that is effective to treat type 2 diabetes.

Yet another aspect of the invention that is of interest relates to a method of treating non-insulin dependent diabetes mellitus in a mammalian patient in need of such treatment comprising administering to the patient a compound in accordance with formula I or a pharmaceutically acceptable salt or solvate thereof in an amount that is effective to treat non-insulin dependent diabetes mellitus.

Yet another aspect of the invention that is of interest relates to a method of treating obesity in a mammalian patient in need of such treatment comprising administering to said patient a compound in accordance with formula I or a pharmaceutically acceptable salt or solvate thereof in an amount that is effective to treat obesity.

Yet another aspect of the invention that is of interest relates to a method of treating Syndrome X in a mammalian patient in need of such treatment, comprising administering to said patient a compound in accordance with formula I or a pharmaceutically acceptable salt or solvate thereof in an amount that is effective to treat Syndrome X.

Yet another aspect of the invention that is of interest relates to a method of treating a lipid disorder selected from the group consisting of dyslipidemia, hyperlipidemia, hypertriglyceridemia, hypercholesterolemia, low HDL and high LDL in a mammalian patient in need of such treatment, comprising administering to said patient a compound in accordance with formula I or a pharmaceutically acceptable salt or solvate thereof in an amount that is effective to treat said lipid disorder.

Yet another aspect of the invention that is of interest relates to a method of treating atherosclerosis in a mammalian patient in need of such treatment, comprising administering to said patient a compound in accordance with a compound in accordance with formula I or a pharmaceutically acceptable salt or solvate thereof in an amount that is effective to treat atherosclerosis.

Yet another aspect of the invention that is of interest relates to a method of treating a condition selected from the group consisting of: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, (21) hypertension and other conditions and disorders where insulin resistance is a component, in a mammalian patient in need of such treatment, comprising administering to the patient a compound in accordance with formula I or a pharmaceutically acceptable salt or solvate thereof in an amount that is effective to treat said condition.

Yet another aspect of the invention that is of interest relates to a method of delaying the onset of a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, (21) hypertension and other conditions and disorders where insulin resistance is a component in a mammalian patient in need thereof, comprising administering to the patient a compound in accordance with formula I or a pharmaceutically acceptable salt or solvate thereof in an amount that is effective to delay the onset of said condition.

Yet another aspect of the invention that is of interest relates to a method of reducing the risk of developing a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, (21) hypertension and other conditions and disorders where insulin resistance is a component in a mammalian patient in need thereof, comprising administering to the patient a compound in accordance with formula I or a pharmaceutically acceptable salt or solvate thereof in an amount that is effective to reduce the risk of developing said condition.

Yet another aspect of the invention that is of interest relates to a method of treating a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, (21) hypertension and other conditions and disorders where insulin resistance is a component, in a mammalian patient in need of such treatment, comprising administering to the patient a compound in accordance with formula I or a pharmaceutically acceptable salt or solvate thereof in an amount that is effective to treat said condition, and a compound selected from the group consisting of:

(a) DP-IV inhibitors;
(b) insulin sensitizers selected from the group consisting of (i) PPAR agonists and (ii) biguanides;
(c) insulin and insulin mimetics;
(d) sulfonylureas and other insulin secretagogues;
(e) α-glucosidase inhibitors;
(f) glucagon receptor antagonists;
(g) GLP-1, GLP-1 mimetics, and GLP-1 receptor agonists;
(h) GIP, GIP mimetics, and GIP receptor agonists;
(i) PACAP, PACAP mimetics, and PACAP receptor 3 agonists;
(j) cholesterol lowering agents selected from the group consisting of
  (i) HMG-CoA reductase inhibitors, (ii) sequestrants, (iii) nicotinyl alcohol, nicotinic acid and salts thereof, (iv) PPARα agonists, (v) PPARα/γ dual agonists, (vi) inhibitors of cholesterol absorption, (vii) acyl CoA:cholesterol acyltransferase inhibitors, and (viii) anti-oxidants;
(k) PPARδ agonists;
(l) antiobesity compounds;
(m) ileal bile acid transporter inhibitors;
(n) anti-inflammatory agents excluding glucocorticoids;
(o) protein tyrosine phosphatase-1B (PTP-1B) inhibitors; and
(p) antihypertensives including those acting on the angiotensin or renin systems, such as angiotensin converting enzyme inhibitors, angiotensin II receptor antagonists or renin inhibitors, such as captopril, cilazapril, enalapril, fosinopril, lisinopril, quinapril, ramapril, zofenopril, candesartan, cilexetil, eprosartan, irbesartan, losartan, tasosartan, telmisartan, and valsartan;
said compounds being administered to the patient in an amount that is effective to treat said condition.

Yet another aspect of the invention that is of interest relates to a method of treating a condition selected from the group consisting of hypercholesterolemia, atherosclerosis, low HDL levels, high LDL levels, hyperlipidemia, hypertriglyceridemia and dyslipidemia, in a mammalian patient in need of such treatment, comprising administering to the patient a compound in accordance with formula I or a pharmaceutically acceptable salt or solvate thereof and an HMG-CoA reductase inhibitor, in amounts that are effective to treat said condition.

More particularly, another aspect of the invention that is of interest relates to a method of treating a condition selected from the group consisting of hypercholesterolemia, atherosclerosis, low HDL levels, high LDL levels, hyperlipidemia, hypertriglyceridemia and dyslipidemia, in a mammalian patient in need of such treatment, comprising administering to the patient a compound in accordance with formula I or a pharmaceutically acceptable salt or solvate thereof and an HMG-CoA reductase inhibitor in the form of a statin, said compounds being administered in amounts that are effective for treating said condition. Statins useful in this regard include the group consisting of lovastatin, simvastatin, pravastatin, fluvastatin, atorvastatin, itavastatin, ZD-4522 and rivastatin.

A method of reducing the risk of developing a condition selected from the group consisting of hypercholesterolemia, atherosclerosis, low HDL levels, high LDL levels, hyperlipidemia, hypertriglyceridemia and dyslipidemia, and the sequelae of such conditions comprising administering to a mammalian patient in need of such treatment a therapeutically effective amount of a compound as defined in Claim 1 and an HMG-CoA reductase inhibitor.

More particularly, another aspect of the invention that is of interest relates to a method of delaying the onset or reducing the risk of developing atherosclerosis in a human patient in need of such treatment comprising administering to the patient a compound in accordance with formula I or a pharmaceutically acceptable salt or solvate thereof and an HMG-CoA reductase inhibitor in the form of a statin, said compounds being administered in amounts that are effective for treating said condition. Statins useful in this regard include the group consisting of lovastatin, simvastatin, pravastatin, fluvastatin, atorvastatin, itavastatin, ZD-4522 and rivastatin.

More particularly, another aspect of the invention that is of interest relates to a method of treating, delaying the onset or reducing the risk of developing atherosclerosis in a human patient in need of such treatment comprising administering to the patient a compound in accordance with formula I or a pharmaceutically acceptable salt or solvate thereof and a cholesterol absorption inhibitor, said compounds being administered in amounts that treat, delay the onset, or reduce the risk of developing atherosclerosis.

Even more particularly, another aspect of the invention that is of interest relates to a method of treating, delaying the onset or reducing the risk of developing atherosclerosis in a human patient in need of such treatment comprising administering to the patient a compound in accordance with formula I or a pharmaceutically acceptable salt or solvate thereof and a cholesterol absorption inhibitor, wherein the cholesterol absorption inhibitor is ezetimibe, said compounds being administered in amounts that treat, delay the onset, or reduce the risk of developing atherosclerosis.

Yet another aspect of the invention that is of interest relates to a pharmaceutical composition that is comprised of: (1) a compound according to formula I or a pharmaceutically acceptable salt or solvate thereof,
(2) a compound selected from the group consisting of:
(a) DP-IV inhibitors;
(b) insulin sensitizers selected from the group consisting of (i) PPAR agonists and (ii) biguanides;
(c) insulin and insulin mimetics;
(d) sulfonylureas and other insulin secretagogues;
(e) α-glucosidase inhibitors;
(f) glucagon receptor antagonists;
(g) GLP-1, GLP-1 mimetics, and GLP-1 receptor agonists;
(h) GIP, GIP mimetics, and GIP receptor agonists;
(i) PACAP, PACAP mimetics, and PACAP receptor 3 agonists;
(j) cholesterol lowering agents selected from the group consisting of (i) HMG-CoA reductase inhibitors, (ii) sequestrants, (iii) nicotinyl alcohol, nicotinic acid or a salt thereof, (iv) PPARα agonists, (v) PPARα/γ dual agonists, (vi) inhibitors of cholesterol absorption, (vii) acyl CoA:cholesterol acyltransferase inhibitors, and (viii) anti-oxidants;
(k) PPARδ agonists;
(l) antiobesity compounds;
(m) ileal bile acid transporter inhibitors;
(n) anti-inflammatory agents other than glucocorticoids;
(o) protein tyrosine phosphatase-1B (PTP-1B) inhibitors; and
(p) antihypertensives including those acting on the angiotensin or renin systems, such as angiotensin converting enzyme inhibitors, angiotensin II receptor antagonists or renin inhibitors, such as captopril, cilazapril, enalapril, fosinopril, lisinopril, quinapril, ramapril, zofenopril, candesartan, cilexetil, eprosartan, irbesartan, losartan, tasosartan, telmisartan, and valsartan; and
(3) a pharmaceutically acceptable carrier Another aspect of the invention that is of interest relates to the use of a compound in accordance with formula I or a pharmaceutically acceptable salt or solvate thereof in the manufacture of a medicament for use in treating a disease or condition described herein.

The compounds of the invention can be prepared using the synthetic schemes described herein. The following abbreviations are used in the synthetic schemes:

Ac is acetyl [CH$_3$C(O)—]; Ac$_2$O is acetic anhydride; AcAc is acetyl acetonoate; Ar is Aryl; ArX is an aryl halide; 9-BBN is 9-borabicyclo[3.3.1]nonane; Bn is benzyl; BOC is tert Butyloxycarbonyl; DBU is diazabicycloundecane; DIAD is diisopropylazodicarboxylate; MAL is diisobutylaluminum hydride; DMF is N,N-dimethylformamide; DMSO is dimethyl sulfoxide; EDAC (or EDC) is 1-ethyl-3-[3-(dimethylamino)propyl]-carbodiimide HCl; Et$_3$N is triethylamine; Et is ethyl; EtOAc is ethyl acetate; EtOH is ethanol; HCl is hydrochloric acid; Het-X is heterocyclic halide; HOBt is 1-hydroxybenzotriazole; HPLC is high performance liquid chromatography; LG is leaving group; M is molar; mmol is millimole; Me is methyl; MeOH is methanol; MsCl methanesulfonyl chloride; N is normal; NaHMDS is sodium hexamethyldisiliazide; NaOAc is sodium acetate; NaOtBu is sodium tert-butoxide; NMO is N-methylmorpholine N oxide; NMP is N-methylpyrrolidinone; PG is protecting group; Pd(dba)$_2$ is tris(dibenzylideneacetone)dipalladium; PdCl$_2$(Ph$_3$P)$_2$ is dichlorobis-(triphenylphosphene) palladium; PG Denotes an unspecified protecting group; Ph is phenyl; PhMe is toluene; PPh$_3$ is triphenylphosphine; PMB is para-methoxybenzyl; RT is room temperature; TBAF is tetrabutyl ammonium fluoride; TBS is tert-butyldimethylsilyl; tBu is tert-butyl; Tf is triflate; TFA is trifluoroacetic acid; THF is tetrahydrofuran; TLC is thin layer chromatography; TMEDA is tetramethylethylenediamine; TMS is trimethylsilyl; TPAP is tetrapropylammonium perruthenate. In the general schemes, the designations R$_1$-R$_5$ serve as placeholders. The ring containing H shown below denotes a heterocycle. In scheme 4, E is an ester forming group, e.g., propyl, butyl, and the like.

General Schemes

The substituted bipiperidines of this invention can be prepared by any of several methods. The specific examples detailed below may employ some of the following general procedures.

Substituted aryl and heteroaryl coupling intermediates shown in the schemes are commercially available or may be prepared from readily accessible aryl, heterocycles, or other congeners via a host of routes. Intermediates are accessible through either modification of a preformed heteroaryl scaffold or through de novo ring synthesis.

Many of the piperidine intermediates required for the preparation of this invention are available commercially or through published procedures. One of the most useful means synthese utilizes a reduction of a suitable pyridine. Low pressure reductions with hydrogen and 5-10% Pd on charcoal or similar hydrogenation catalyst in acetic acid lead to the appropriate piperidine (scheme 1).

Various aryl (heteroaryl)/amine coupling methods are well suited to production of these intermediates. A general method, SnAr displacement, is depicted in Scheme 2.

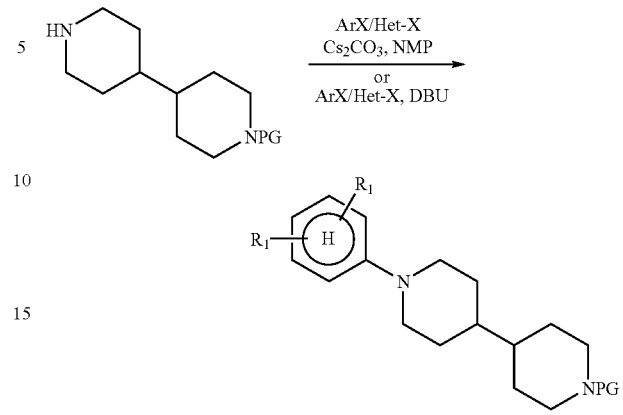

One useful synthetic method is Buchwald coupling, as outlined in Scheme 3 and described in several literature reviews. Scheme 3 indicates convenient methods for coupling the required partners.

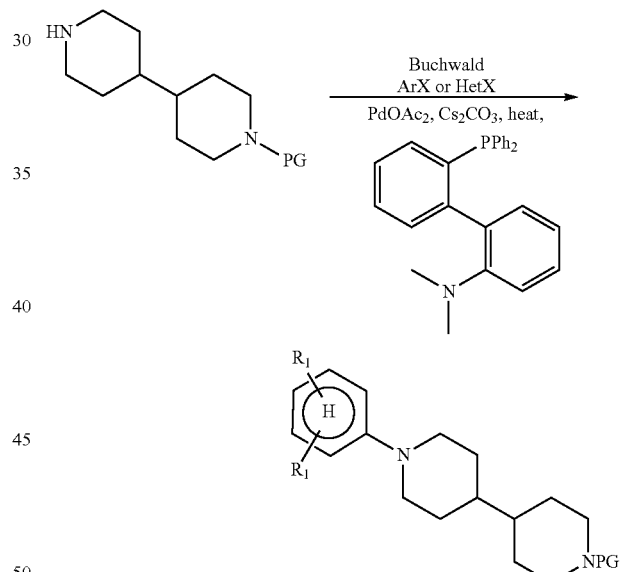

Heterocyclic residues of either Arl or the Het fragment are obtainable by de novo ring synthesis. An example of de novo ring synthesis for thiazole and pyrimidine cases is shown in Scheme 4. A host of methods can be used.

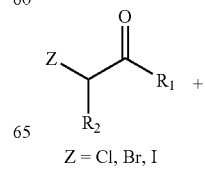

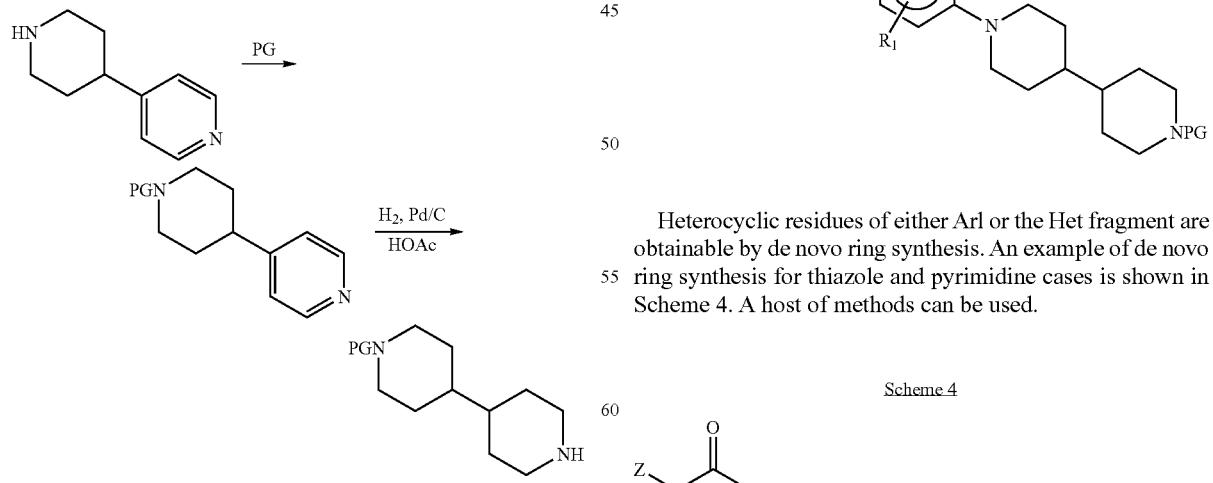

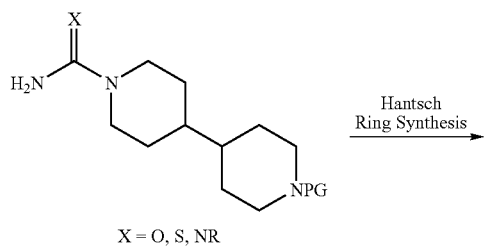
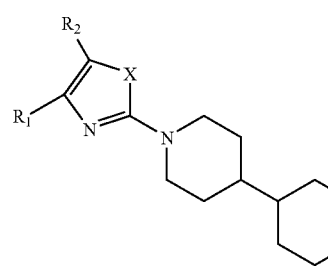
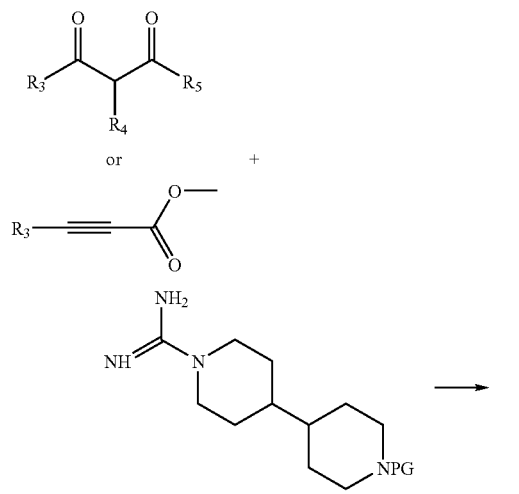
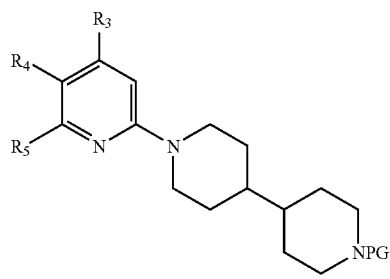
When the N-Aryl or N-heteroaryl residue is substituted with an X group (where X=Cl, Br, I or OTf) it is possible to further functionalize the residue utilizing palladium organometallic mediated coupling reactions. A method with extraordinarily broad applicability are palladium mediated couplings outlined in Scheme 5.
Scheme 5
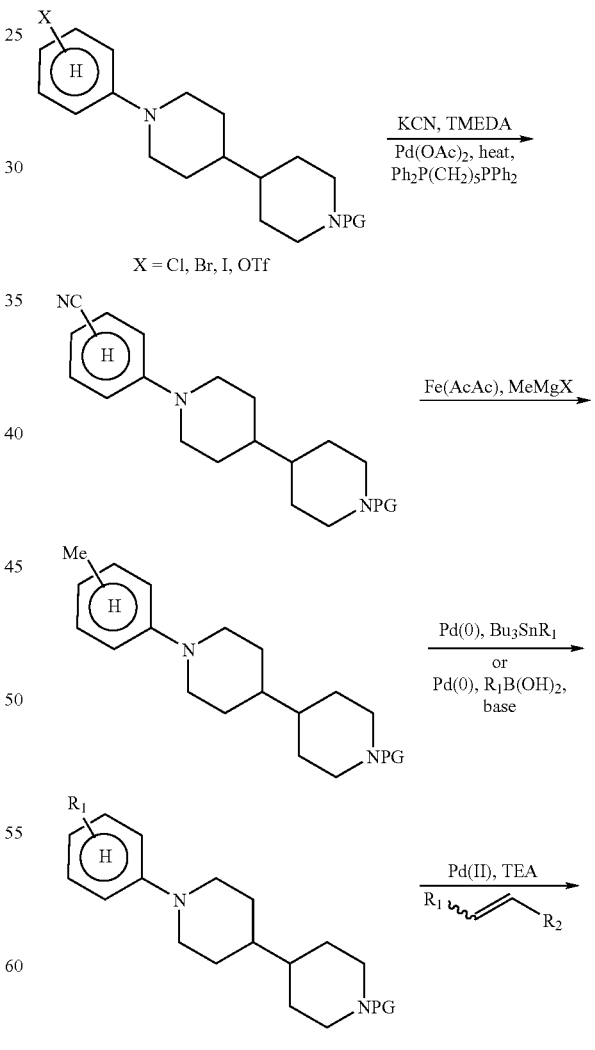

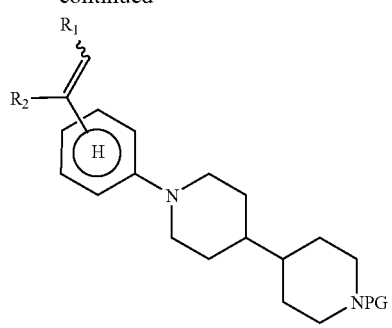

Removal of the protecting group from the N-fuctionalized derivatives described above produces compounds that can be further functionalized. Scheme 6 describes methods of preparation.

Scheme 6

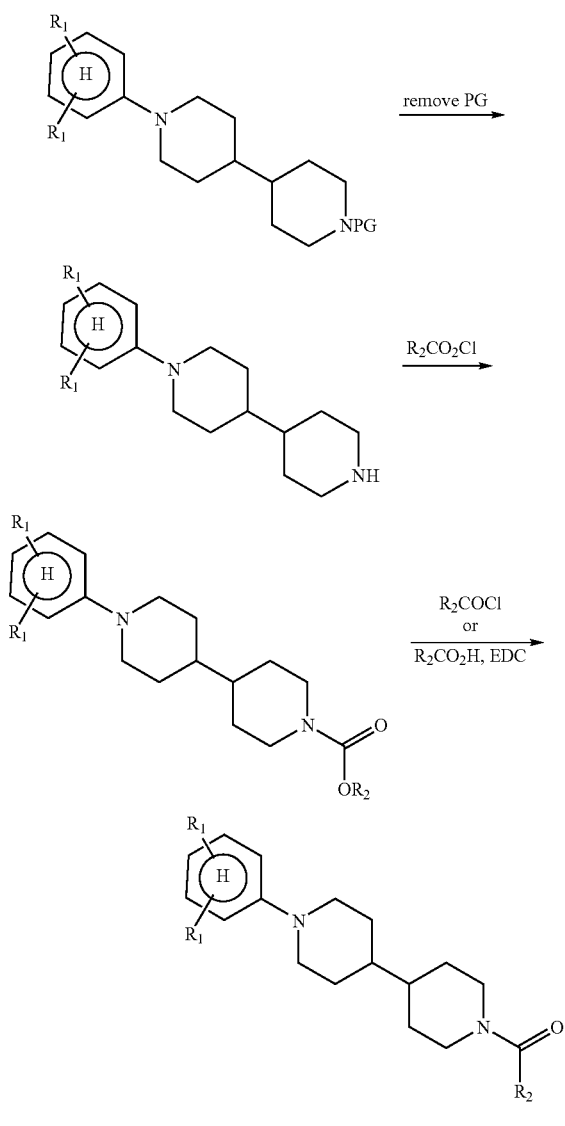

General Procedure 1 (Nucleophilic Aromatic Substitution)

EXAMPLE 1.1 tert-butyl 1'-[4-(methylsulfonyl)phenyl]-4,4'-bipiperidine-1-carboxylate

A solution of tert-butyl 4,4'-bipiperidine-1-carboxylate (100 mg; 0.373 mmol,) obtained from commercially available sources (Arch Chemical or ABChem Inc.) and 1-fluoro-4-(methylsulfonyl)benzene (65 mg; 0.373) in DMF (5 mL) was treated with cesium carbonate (182 mg; 0.559 mmol) and stirred at 60 C for 18 h. The reaction was diluted with ethyl acetate (50 mL). The organic phase then washed twice with water (2×150 mL). The organic phase was dried over $Na_2SO_3$, filtered, and concentrated in vac to a residue. The crude product was purified by chromatography on silica gel and eluted with ethyl acetate. The title compound was isolated.

500 MHz NMR ($CDCl_3$): δ 7.74 (d, 2H, J=9 Hz), 6.93 (d, 2H, J=8.5 Hz), 4.13 (bs, 2H), 3.91 (d, 2H, J=13 Hz), 3.00 (s, 3H), 2.84 (t, 2H, J=11.5 Hz), 2.64 (t, 2H, J=12.5 Hz), 1.81 (d, 2H, J=10 Hz), 1.68 (d, 2H, J=12.5 Hz), 1.45 (s, 9H), 1.34 (m, 4H), 1.15 (m, 2H).). LCMS calc: 422.59. obs: 423.13 (M+H).

General Procedure 2 (Buchwald Coupling)

EXAMPLE 1.2

Preparation of tert-butyl 1'-{4-[(trifluoromethyl)sulfonyl]phenyl}-4,4'-bipiperidine-1-carboxylate

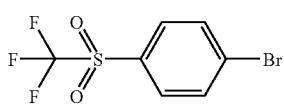

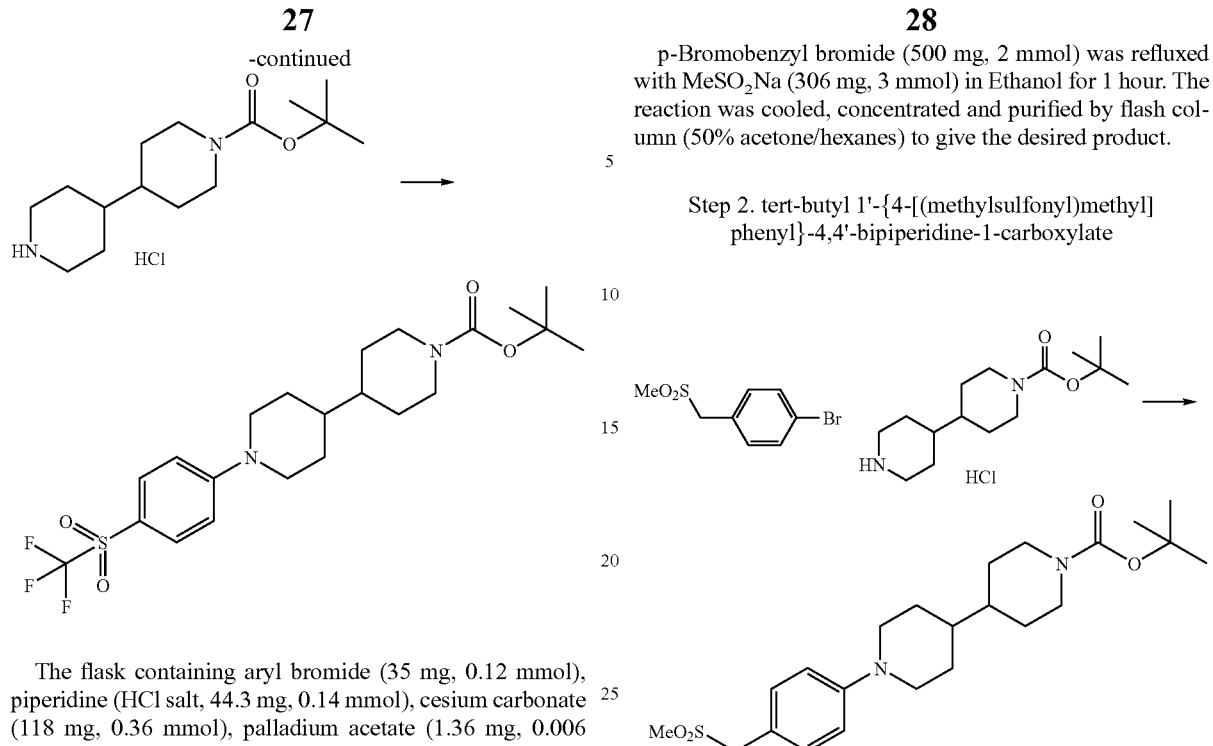

The flask containing aryl bromide (35 mg, 0.12 mmol), piperidine (HCl salt, 44.3 mg, 0.14 mmol), cesium carbonate (118 mg, 0.36 mmol), palladium acetate (1.36 mg, 0.006 mmol), 2-(diphenylphosphino)-2'-(N,N-dimethylamino)biphenyl (4.6 mg, 0.012 mmol) was applied to vacuum and refilled with argon alternatively for 3 times. DMF (0.24 mL) was added through a syringe, and the mixture was degassed for another 3 times. The reaction mixture was stirred under argon at 90° C. overnight, after cooling down, ethyl acetate (4 mL) was added, and the mixture was washed with water (0.5 mL×2), brine and dried over sodium sulfate. Purification with preparative TLC (30/70 Ethyl acetate/Hexane) yielded the title compound.

LRMS calc: 476.2. obs: 377.1 (M−99), 321.1 (M−55), 499.1 (M+23).

General Procedure 3:

EXAMPLE 1.23 (Table 1)

Preparation of tert-butyl 1'-{4-[(methylsulfonyl)methyl]phenyl}-4,4'-bipiperidine-1-carboxylate Step 1. 4-bromobenzyl methyl sulfone p-Bromobenzyl bromide (500 mg, 2 mmol) was refluxed with MeSO$_2$Na (306 mg, 3 mmol) in Ethanol for 1 hour. The reaction was cooled, concentrated and purified by flash column (50% acetone/hexanes) to give the desired product.

Step 2. tert-butyl 1'-{4-[(methylsulfonyl)methyl]phenyl}-4,4'-bipiperidine-1-carboxylate

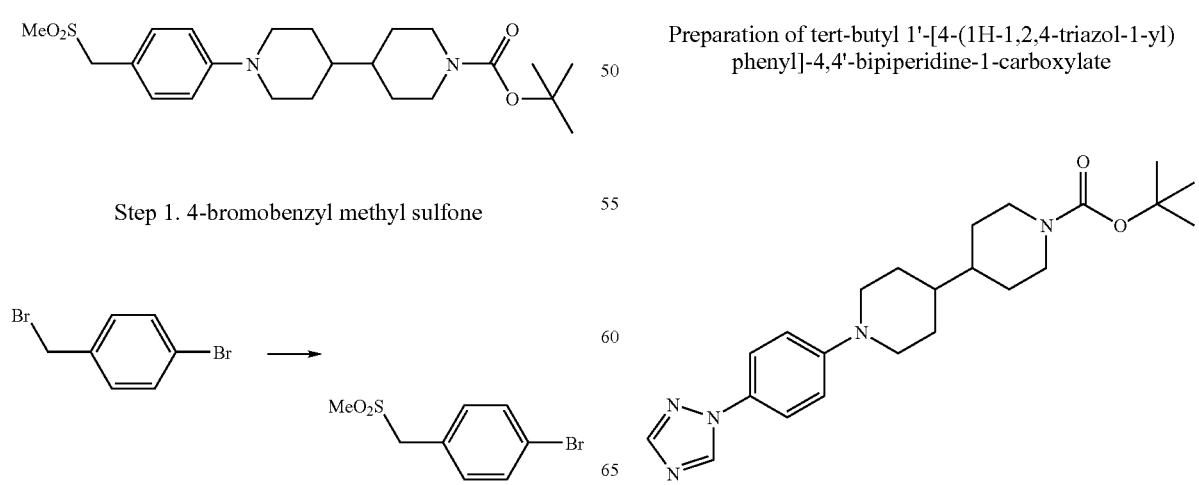

The flask containing aryl bromide (50 mg, 0.2 mmol), piperidine (HCl salt, 73 mg, 0.24 mmol), cesium carbonate (163 mg, 0.5 mmol), palladium acetate (2.24 mg, 0.01 mmol), bis(tri-tert-butylphosphoranyl)palladium (3.4 mg, 0.067 mmol) was applied to vacuum and refilled with argon alternatively for 3 times. Dioxane (0.5 mL) was added through a syringe, and the mixture was degassed for another 3 times. The reaction mixture was stirred under argon at 80° C. for 3 hours, after cooling down, ethyl acetate (4 mL) was added, and the mixture was washed with water (0.5 mL×2), brine and dried over sodium sulfate. Purification with preparative TLC (30% acetone/hexanes) yielded the title compound. LRMS calc: 436.2. obs: 437.2 (M+1).

General Procedure 4:

EXAMPLE 1.24 (Table 1)

Preparation of tert-butyl 1'-[4-(1H-1,2,4-triazol-1-yl)phenyl]-4,4'-bipiperidine-1-carboxylate

Step 1 tert-butyl 1'-(4-iodophenyl)-4,4'-bipiperidine-1-carboxylate

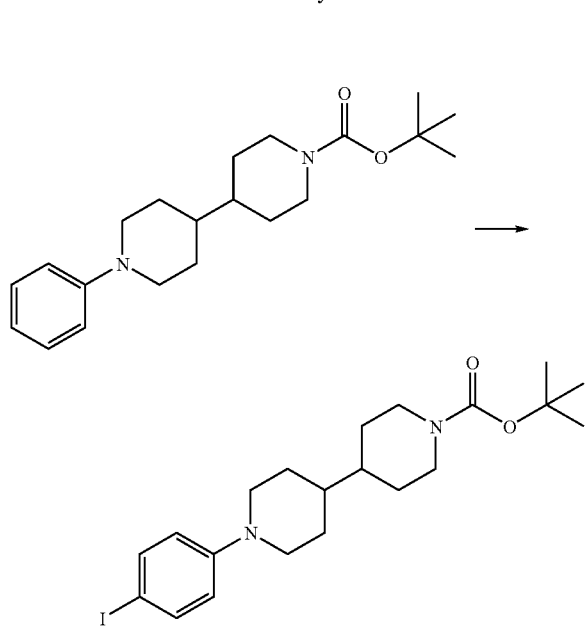

To a solution of tert-butyl 1'-phenyl-4,4'-bipiperidine-1-carboxylate (0.688 g, 2 mmol), synthesized similarly as described for example 301, in methylene chloride (40 mL) was added bis(collidine)iodine (I) hexafluorophosphate (2.05 g, 4 mmol). After stirring the reaction mixture for 10 min at room temperature, the solvent was removed under vacuum and the residue purified by chromatography on silica gel (hexane/ether).

Step 2 tert tert-butyl 1'-[4-(1H-1,2,4-triazol-1-yl)phenyl]-4,4'-bipiperidine-1-carboxylate

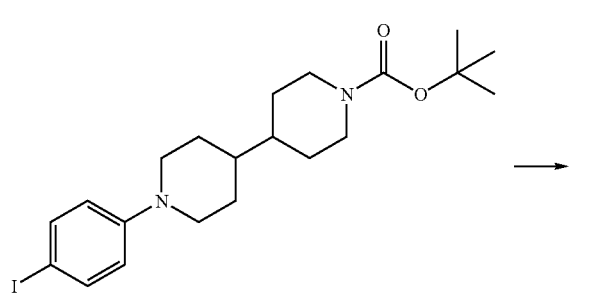

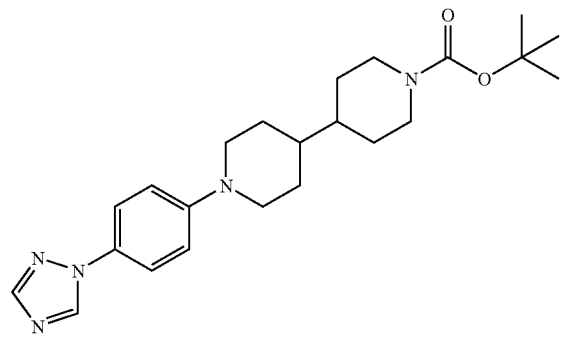 [SMILES: CC(C)(C)OC(=O)N1CCC(C2CCN(c3ccc(-n4cncn4)cc3)CC2)CC1]

tert-Butyl 1'-(4-iodophenyl)-4,4'-bipiperidine-1-carboxylate (17 mg, 0.036 mmol) from Step 1, 1H-1,2,4-triazole (7.5 mg, 0.108 mmol), CuI (0.7 mg, 0.0036 mmol), N,N-dimethylethane-1,2-diamine (1 mg, 0.0072 mmol), $K_3PO_4$ (16 mg, 0.0756 mmol) were mixed in a 1 dram vial, followed by addition of DMF (0.1 mL). The reaction vessel was degassed and back-filled with Ar 3 times, before it was heated at 100° C. for 20 hours. The reaction was cooled, diluted with water, extracted with EtOAc, concentrated and purified by PTLC to give the title compound.

500 MHz NMR ($CDCl_3$): δ 8.49 (s, 1H), 8.12 (s, 1H), 7.53 (d, 2H, J=9 Hz), 7.03 (d, 2H, J=9 Hz), 4.17 (bs, 2H), 3.81 (d, 2H, J=12.5 Hz), 2.75 (dt, 2H, J=12.3 Hz, 2.3 Hz), 2.69 (bs, 2H), 1.85 (d, 2H, J=11.9 Hz), 1.74 (d, 2H, J=12.1 Hz), 1.49 (s, 9H), 1.44 (m, 2H), 1.29 (m, 2H), 1.20 (m, 2H).

TABLE 1

| Example | Procedure | Chemical name | Chemical Structure | (M + 1) |
|---|---|---|---|---|
| 1.1 | 1 | tert-butyl 1'-[4-(methylsulfonyl)phenyl]-4,4'-bipiperidine-1-carboxylate | 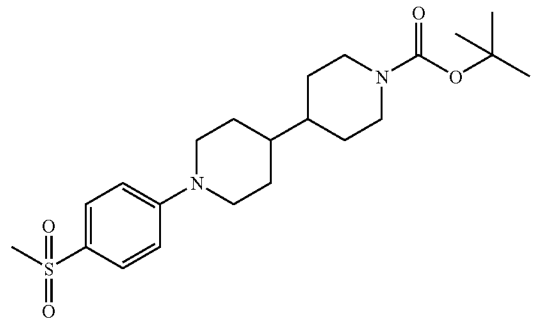 [SMILES: CC(C)(C)OC(=O)N1CCC(C2CCN(c3ccc(S(C)(=O)=O)cc3)CC2)CC1] | 423.1 |
| 1.2 | 1 | tert-butyl 1'-{4-[(trifluoromethyl)sulfonyl]phenyl}-4,4'-bipiperidine-1-carboxylate | 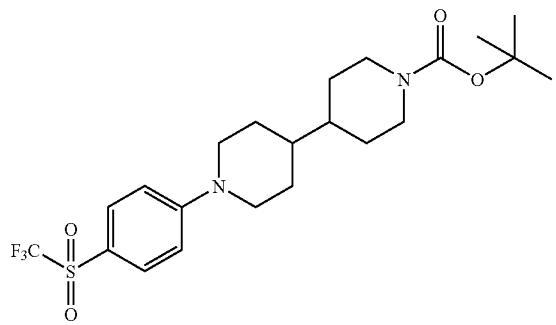 [SMILES: CC(C)(C)OC(=O)N1CCC(C2CCN(c3ccc(S(=O)(=O)C(F)(F)F)cc3)CC2)CC1] | 377.1 |
| 1.3 | 1 | tert-butyl 1'-[2-fluoro-4-(methylsulfonyl)phenyl]-4,4'-bipiperidine-1-carboxylate | 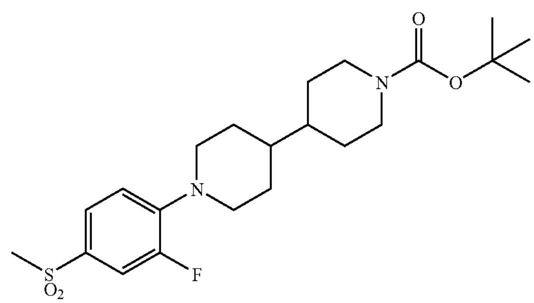 [SMILES: CC(C)(C)OC(=O)N1CCC(C2CCN(c3ccc(S(C)(=O)=O)cc3F)CC2)CC1] | 441.45 |
| 1.4 | 1 | tert-butyl 1'-[4-(methylsulfonyl)-2-(trifluoromethyl)phenyl]-4,4'-bipiperidine-1-carboxylate | 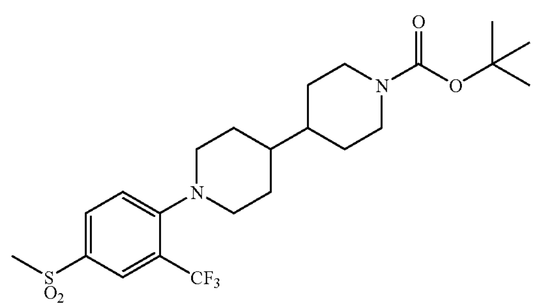 [SMILES: CC(C)(C)OC(=O)N1CCC(C2CCN(c3ccc(S(C)(=O)=O)cc3C(F)(F)F)CC2)CC1] | 491.2 |
| 1.5 | 2 | tert-butyl 1'-{4-[2-(methylsulfonyl)ethyl]phenyl}-4,4'-bipiperidine-1-carboxylate | 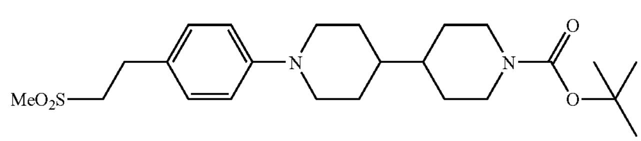 [SMILES: CC(C)(C)OC(=O)N1CCC(C2CCN(c3ccc(CCS(C)(=O)=O)cc3)CC2)CC1] | 451.1 |
| 1.6 | 2 | tert-butyl 1'-(4-acetylphenyl)-4,4'-bipiperidine-1-carboxylate | 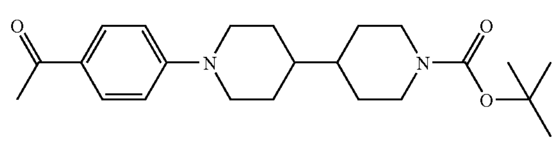 [SMILES: CC(=O)c1ccc(N2CCC(C3CCN(C(=O)OC(C)(C)C)CC3)CC2)cc1] | 387.6 |

TABLE 1-continued

| Example | Procedure | Chemical name | Chemical Structure | (M + 1) |
|---------|-----------|---------------|--------------------|---------|
| 1.7 | 2 | tert-butyl 1'-(4-methylphenyl)-4,4'-bipiperidine-1-carboxylate | 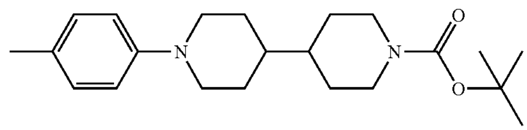 [SMILES: Cc1ccc(N2CCC(C3CCN(C(=O)OC(C)(C)C)CC3)CC2)cc1] | 359.1 |
| 1.8 | 2 | tert-butyl 1'-(4-chlorophenyl)-4,4'-bipiperidine-1-carboxylate | 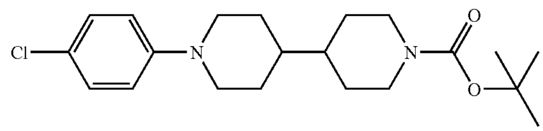 [SMILES: CC(C)(C)OC(=O)N1CCC(C2CCN(c3ccc(Cl)cc3)CC2)CC1] | 379.1 |
| 1.9 | 2 | tert-butyl 1'-(3-chloro-5-fluorophenyl)-4,4'-bipiperidine-1'-carboxylate | 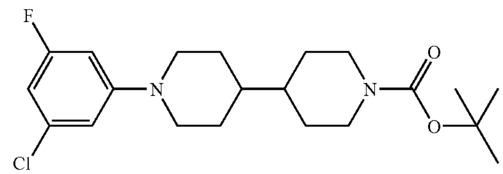 | 341.1 (M − 55) |
| 1.10 | 2 | tert-butyl 1'-(3-chloro-4-methylphenyl)-4,4'-bipiperidine-1-carboxylate | 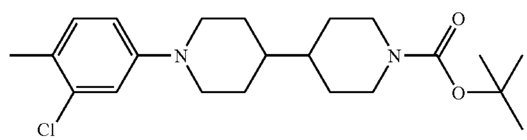 | 393.5 |
| 1.11 | 2 | tert-butyl 1'-(3-chloro-4-cyanophenyl)-4,4'-bipiperidine-1-carboxylate | 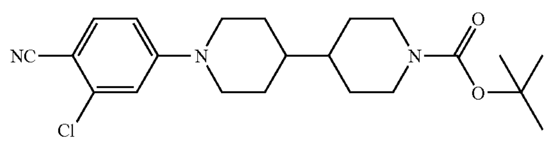 | 404.2 |
| 1.12 | 2 | tert-butyl 1'-(4-acetyl-3-chlorophenyl)-4,4'-bipiperidine-1-carboxylate | 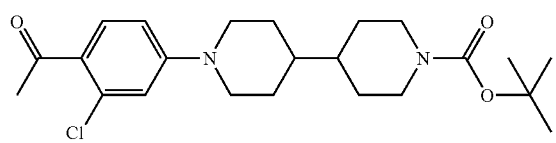 [SMILES: CC(=O)c1ccc(N2CCC(C3CCN(C(=O)OC(C)(C)C)CC3)CC2)cc1Cl] | 421.1 |
| 1.13 | 2 | tert-butyl 1'-(3-cyano-4-methylphenyl)-4,4'-bipiperidine-1-carboxylate | 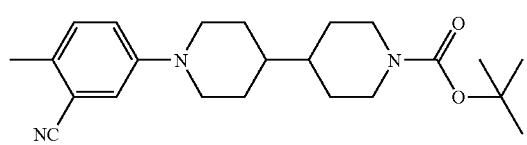 | 328.1 (M − 55) |
| 1.14 | 2 | tert-butyl 1'-(3,5-dichlorophenyl)-4,4'-bipiperidine-1-carboxylate | 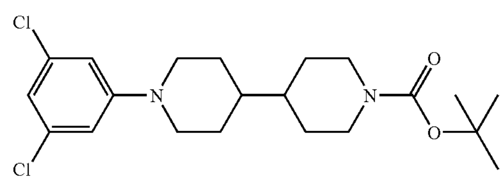 [SMILES: CC(C)(C)OC(=O)N1CCC(C2CCN(c3cc(Cl)cc(Cl)c3)CC2)CC1] | 413 |
| 1.15 | 2 | tert-butyl 1'-(3-chloro-5-cyanophenyl)-4,4'-bipiperidine-1-carboxylate | 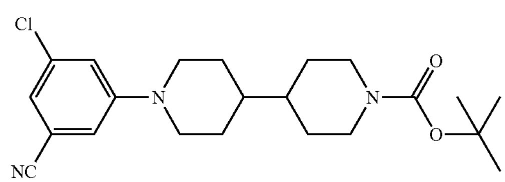 | 348.4 (M − 55) |
| 1.16 | 2 | tert-butyl 1'-(3-bromo-5-cyanophenyl)-4,4'-bipiperidine-1-carboxylate | 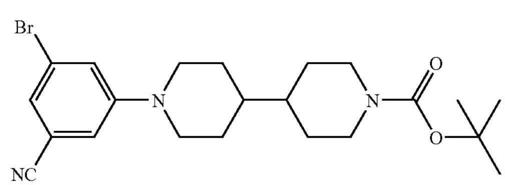 | 392 (M − 55) |

TABLE 1-continued

| Example | Procedure | Chemical name | Chemical Structure | (M + 1) |
|---|---|---|---|---|
| 1.17 | 2 | tert-butyl 1'-(3-cyano-5-fluorophenyl)-4,4'-bipiperidine-1-carboxylate | 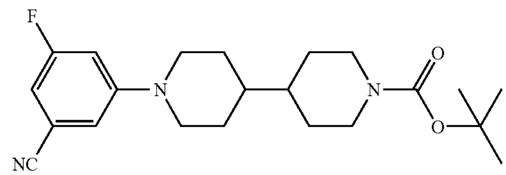 | 332.1 (M − 55) |
| 1.18 | 2 | tert-butyl 1'-(4-cyano-2-fluorophenyl)-4,4'-bipiperidine-1-carboxylate | 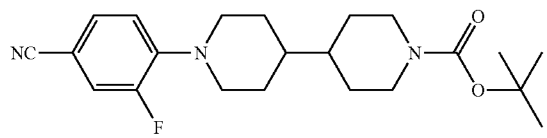 | 332.5 (M − 55) |
| 1.19 | 2 | tert-butyl 1'-[4-cyano-3-(trifluoromethyl)phenyl]-4,4'-bipiperidine-1-carboxylate | 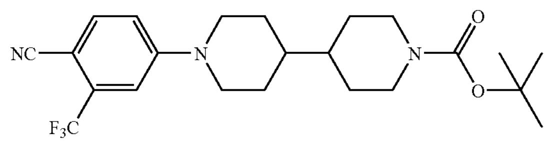 | 338.1 (M − 99) |
| 1.20 | 2 | tert-butyl 1'-[3-chloro-4-(methylsulfonyl)phenyl]-4,4'-bipiperidine-1-carboxylate | 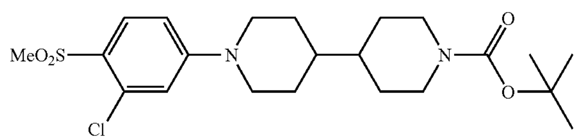 [SMILES: CC(C)(C)OC(=O)N1CCC(C2CCN(c3ccc(S(C)(=O)=O)c(Cl)c3)CC2)CC1] | 357.0 (M − 99) |
| 1.21 | 2 | tert-butyl 1'-(2-bromo-4-cyanophenyl)-4,4'-bipiperidine-1-carboxylate | 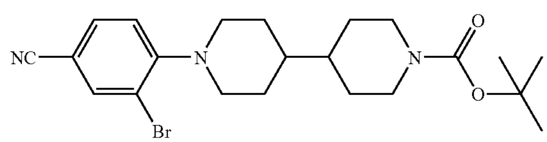 | 392.4 (M − 55) |
| 1.22 | 2 | tert-butyl 1'-(2-chloro-4-cyanophenyl)-4,4'-bipiperidine-1-carboxylate | 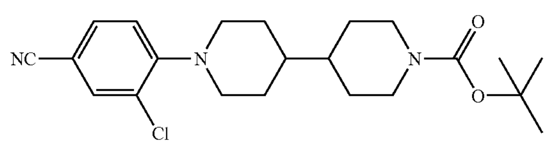 | 348.5 (M − 55) |
| 1.23 | 3 | tert-butyl 1'-{4-[(methylsulfonyl)methyl]phenyl}-4,4'-bipiperidine-1-carboxylate | 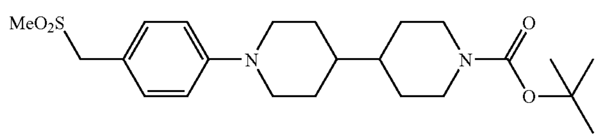 [SMILES: CC(C)(C)OC(=O)N1CCC(C2CCN(c3ccc(CS(C)(=O)=O)cc3)CC2)CC1] | 437.2 |
| 1.25 | 4 | tert-butyl 1'-(4-iodophenyl)-4,4'-bipiperidine-1-carboxylate | 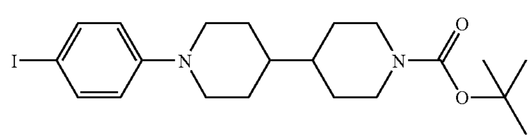 [SMILES: CC(C)(C)OC(=O)N1CCC(C2CCN(c3ccc(I)cc3)CC2)CC1] | 471.3 |
| 1.26 | 2 | tert-butyl 1'-(2-fluoro-5-methylphenyl)-4,4'-bipiperidine-1-carboxylate | 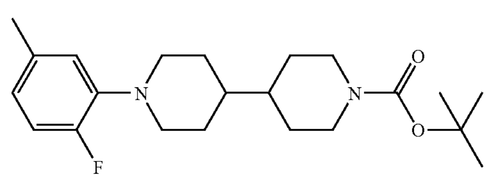 [SMILES: Cc1ccc(F)c(N2CCC(C3CCN(C(=O)OC(C)(C)C)CC3)CC2)c1] | 377.1 |
| 1.27 | 2 | tert-butyl 1'-(3,4-dimethylphenyl)-4,4'-bipiperidine-1-carboxylate | 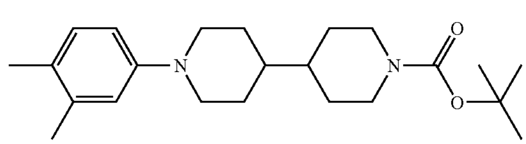 | 373.1 |

TABLE 1-continued

| Example | Procedure | Chemical name | Chemical Structure | (M + 1) |
|---|---|---|---|---|
| 1.28 | 2 | tert-butyl 1'-(3-methylphenyl)-4,4'-bipiperidine-1-carboxylate | 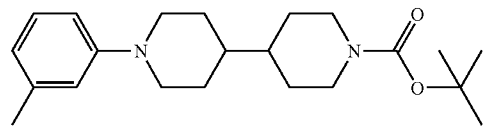 [SMILES: Cc1cccc(N2CCC(C3CCN(C(=O)OC(C)(C)C)CC3)CC2)c1] | 359.1 |
| 1.29 | 2 | tert-butyl 1'-(3-chlorophenyl)-4,4'-bipiperidine-1-carboxylate | 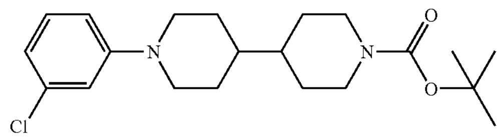 [SMILES: CC(C)(C)OC(=O)N1CCC(C2CCN(c3cccc(Cl)c3)CC2)CC1] | 323.1 (M − 55) |
| 1.30 | 2 | tert-butyl 1'-(3-chloro-2-methylphenyl)-4,4'-bipiperidine-1-carboxylate | 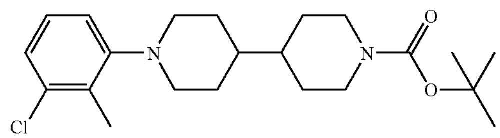 | 393.1 |
| 1.31 | 2 | tert-butyl 1'-(3,5-dimethylphenyl)-4,4'-bipiperidine-1-carboxylate | 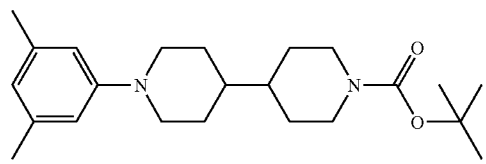 [SMILES: Cc1cc(C)cc(N2CCC(C3CCN(C(=O)OC(C)(C)C)CC3)CC2)c1] | 373.1 |
| 1.32 | 1 | tert-butyl 1'-(4-propionylphenyl)-4,4'-bipiperidine-1-carboxylate | 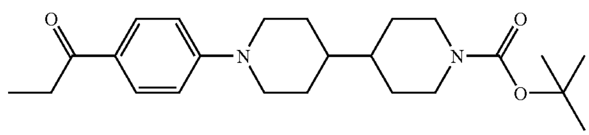 [SMILES: CCC(=O)c1ccc(N2CCC(C3CCN(C(=O)OC(C)(C)C)CC3)CC2)cc1] | 401.1 |
| 1.33 | 2 | tert-butyl 1'-(3-chloro-4-fluorophenyl)-4,4'-bipiperidine-1-carboxylate | 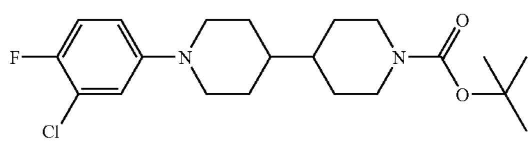 [SMILES: CC(C)(C)OC(=O)N1CCC(C2CCN(c3ccc(F)c(Cl)c3)CC2)CC1] | 397.6 |
| 1.34 | 2 | tert-butyl 1'-(3,4-difluorophenyl)-4,4'-bipiperidine-1-carboxylate | 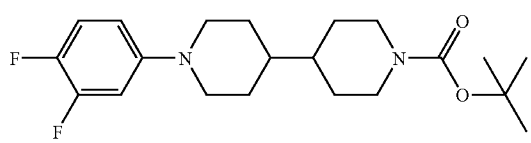 [SMILES: CC(C)(C)OC(=O)N1CCC(C2CCN(c3ccc(F)c(F)c3)CC2)CC1] | 381.5 |
| 1.35 | 2 | tert-butyl 1'-(4-chloro-3-fluorophenyl)-4,4'-bipiperidine-1-carboxylate | 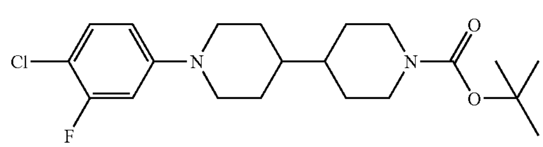 [SMILES: CC(C)(C)OC(=O)N1CCC(C2CCN(c3ccc(Cl)c(F)c3)CC2)CC1] | 397.5 |
| 1.36 | 2 | tert-butyl 1'-(3-fluorophenyl)-4,4'-bipiperidine-1-carboxylate | 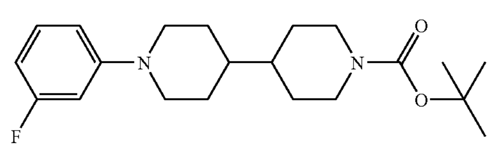 [SMILES: CC(C)(C)OC(=O)N1CCC(C2CCN(c3cccc(F)c3)CC2)CC1] | 363.6 |
| 1.37 | 2 | tert-butyl 1'-(5-cyano-2-fluorophenyl)-4,4'-bipiperidine-1-carboxylate | 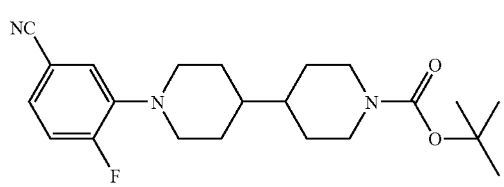 | 332.1 (M − 55) |

TABLE 1-continued

| Example | Procedure | Chemical name | Chemical Structure | (M + 1) |
|---|---|---|---|---|
| 1.38 | 1 | tert-butyl 1'-(2-chloro-4-cyanophenyl)-4,4'-bipiperidine-1-carboxylate | 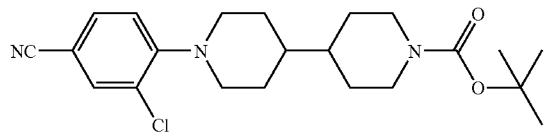 | 348.5 (M − 55) |

General Procedure 2.1 (Nucleophilic Aromatic Substitution)

EXAMPLE 2.1 tert-butyl 1'-[4-(methylsulfonyl)phenyl]-4,4'-bipiperidine-1-carboxylate

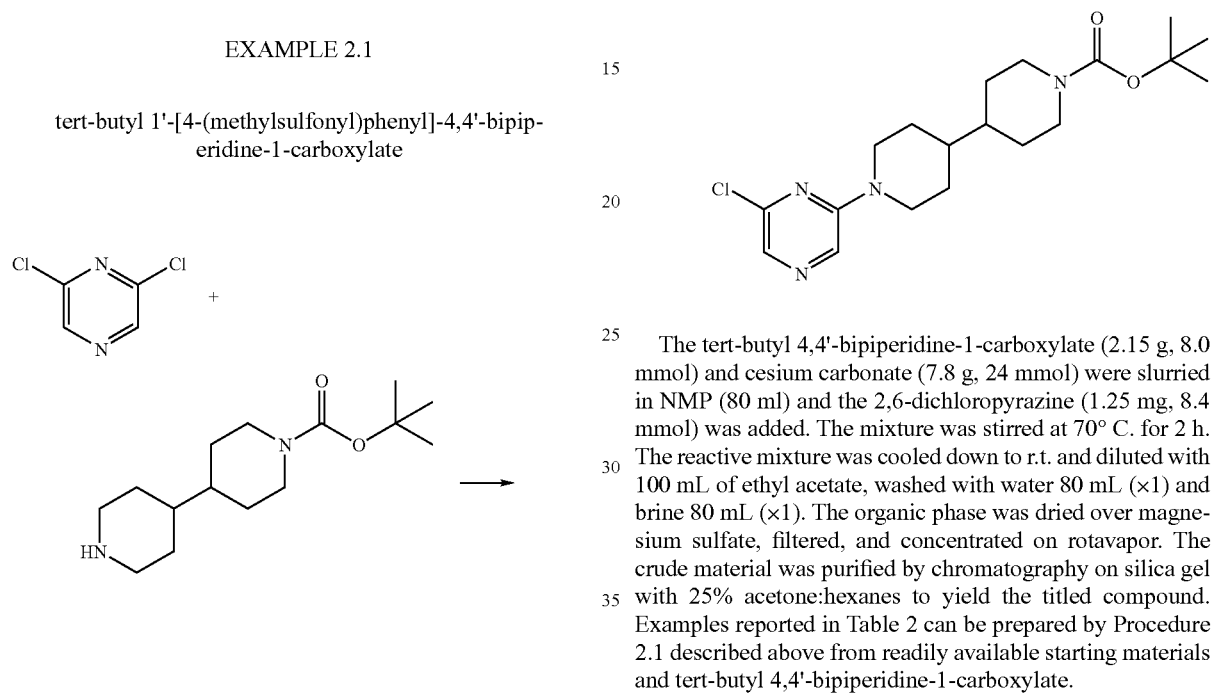

The tert-butyl 4,4'-bipiperidine-1-carboxylate (2.15 g, 8.0 mmol) and cesium carbonate (7.8 g, 24 mmol) were slurried in NMP (80 ml) and the 2,6-dichloropyrazine (1.25 mg, 8.4 mmol) was added. The mixture was stirred at 70° C. for 2 h. The reactive mixture was cooled down to r.t. and diluted with 100 mL of ethyl acetate, washed with water 80 mL (×1) and brine 80 mL (×1). The organic phase was dried over magnesium sulfate, filtered, and concentrated on rotavapor. The crude material was purified by chromatography on silica gel with 25% acetone:hexanes to yield the titled compound. Examples reported in Table 2 can be prepared by Procedure 2.1 described above from readily available starting materials and tert-butyl 4,4'-bipiperidine-1-carboxylate.

TABLE 2

| Example | Procedure | Chemical name | Chemical Structure | (M + 1) |
|---|---|---|---|---|
| 2.1 | 2.1 | tert-butyl 1'-(3,6-dimethylpyrazin-2-yl)-4,4'-bipiperidine-1-carboxylate | 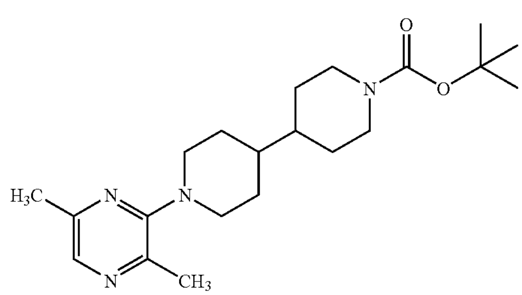 [SMILES: Cc1cnc(C)c(N2CCC(C3CCN(C(=O)OC(C)(C)C)CC3)CC2)n1] | 375.69 |

TABLE 2-continued

| Example | Procedure | Chemical name | Chemical Structure | (M + 1) |
|---|---|---|---|---|
| 2.2 | 2.1 | tert-butyl 1'-[5-(methoxycarbonyl)pyrazin-2-yl]-4,4'-bipiperidine-1-carboxylate | 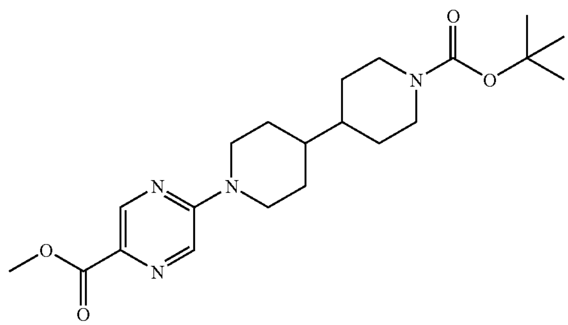 [SMILES: COC(=O)c1cnc(N2CCC(C3CCN(C(=O)OC(C)(C)C)CC3)CC2)cn1] | 405.65 |
| 2.3 | 2.1 | tert-butyl 1'-[2-(methylthio)pyrimidin-4-yl]-4,4'-bipiperidine-1-carboxylate | 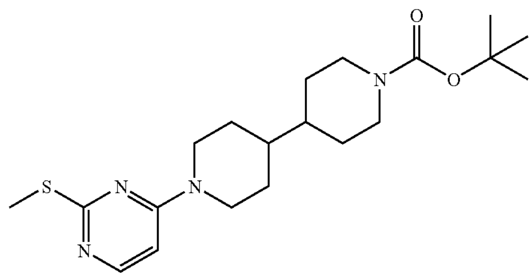 [SMILES: CSc1nccc(N2CCC(C3CCN(C(=O)OC(C)(C)C)CC3)CC2)n1] | 393.64 |
| 2.4 | 2.1 | tert-butyl 1'-(6-methoxypyrazin-2-yl)-4,4'-bipiperidine-1-carboxylate | 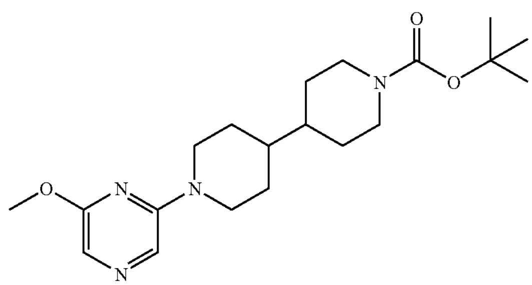 [SMILES: COc1cncc(N2CCC(C3CCN(C(=O)OC(C)(C)C)CC3)CC2)n1] | 377.67 |
| 2.5 | 2.1 | tert-butyl 1'-(6-methoxypyrimidin-4-yl)-4,4'-bipiperidine-1-carboxylate | 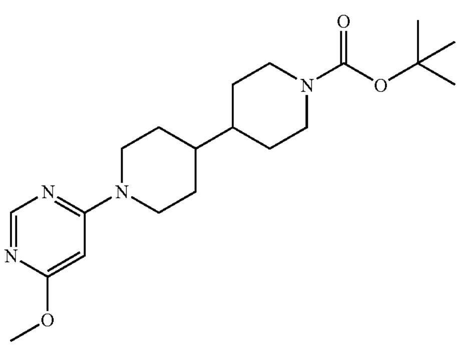 [SMILES: COc1cc(N2CCC(C3CCN(C(=O)OC(C)(C)C)CC3)CC2)ncn1] | 377.67 |
| 2.6 | 2.1 | tert-butyl 1'-(2,6-dimethoxypyrimidin-4-yl)-4,4'-bipiperidine-1-carboxylate | 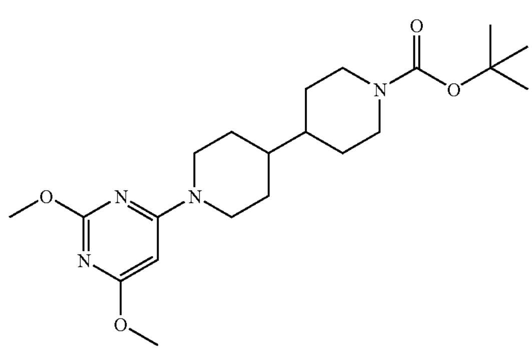 [SMILES: COc1cc(N2CCC(C3CCN(C(=O)OC(C)(C)C)CC3)CC2)nc(OC)n1] | 407.67 |
| 2.7 | 2.1 | tert-butyl 1'-(3-cyanopyrazin-2-yl)- | 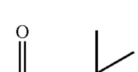 | 394.57 (M + 23) |

General Procedure 3.1:

Preparation of tert-butyl 1'-1'-[2-(trifluoromethyl)pyrimidin-4-yl]-4,4'-bipiperidine-1-carboxylate Step 1: 4-bromo-2-(trifluoromethyl)pyrimidine

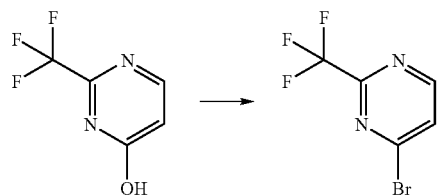 [SMILES: Oc1ccnc(C(F)(F)F)n1 ; FC(F)(F)c1nccc(Br)n1]

The 2-(trifluoromethyl)pyrimidin-4-ol (328 mg, 2.0 mmol) and PBr$_3$ (0.188 mL, 2.0 mmol) were mixed and heated at 150° C. for 3 h. The reaction was cooled down and quenched with ice water, extracted with DCM (20 mL×2) to yield the titled compound. The organic phase was concentrated and crude material was purified by preparative TLC with 20% Acetone:Hexane to yield titled compound.

Step 2: tert-butyl 1'-[2-(trifluoromethyl)pyrimidin-4-yl]-4,4'-bipiperidine-1-carboxylate

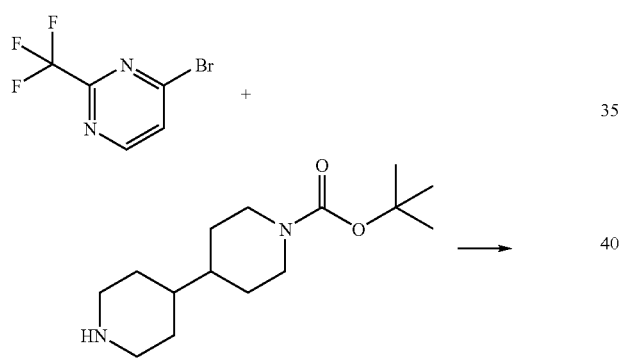

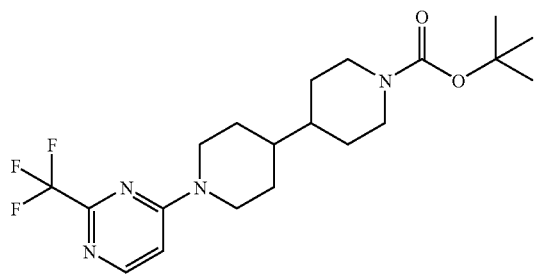

The tert-butyl 4,4'-bipiperidine-1-carboxylate (28.5 mg, 0.11 mmol) and cesium carbonate (106 mg, 0.32 mmol) were stirred in NMP (0.5 ml) and the 4-bromo-2-(trifluoromethyl)pyrimidine (12 mg, 0.053 mmol) was added. The mixture was heated at 70° C. for 2 h. The reaction was cooled down to r.t. and diluted with ethyl acetate (5 mL) and was washed with water 2 mL (×1) and brine 2 mL (×1). The organic phase was dried over magnesium sulfate, filtered, and concentrated on rotavapor. The crude material was purified by preparative TLC with 30% acetone: hexane to yield the titled compound.

LC-MS: 415.60 (M+H).

Examples reported in Table 3 can be prepared by Procedure 3.1 described above.

TABLE 3

| Example | Procedure | Chemical name | Chemical Structure | (M + 1) |
|---|---|---|---|---|
| 3.1 | 3.1 | tert-butyl 1'-[2-(trifluoromethyl)pyrimidin-4-yl]-4,4'-bipiperidine-1-carboxylate | 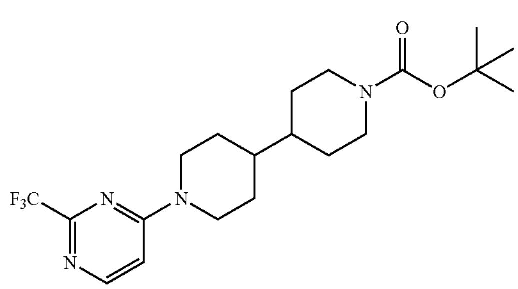 [SMILES: CC(C)(C)OC(=O)N1CCC(C2CCN(c3ccnc(C(F)(F)F)n3)CC2)CC1] | 415.60 |

TABLE 3-continued

| Example | Procedure | Chemical name | Chemical Structure | (M + 1) |
|---|---|---|---|---|
| 3.2 | 3.1 | tert-butyl 1'-[6-(trifluoromethyl)pyrimidin-4-yl]-4,4'-bipiperidine-1-carboxylate | 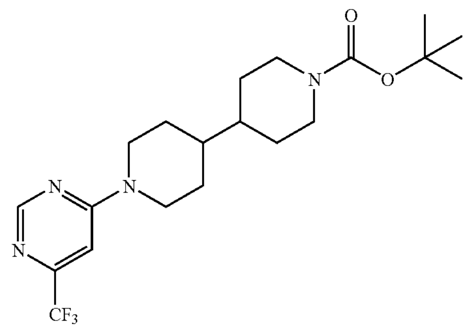 [SMILES: CC(C)(C)OC(=O)N1CCC(C2CCN(c3cc(C(F)(F)F)ncn3)CC2)CC1] | 415.60 |
| 3.3 | 3.1 | tert-butyl 1'-(2,5-dichloropyrimidin-4-yl)-4,4'-bipiperidine-1-carboxylate | 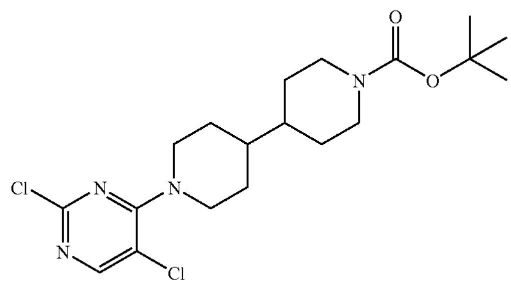 | 437.0 (M + 23) |
| 3.4 | 3.1 | tert-butyl 1'-(4,5-dichloropyrimidin-2-yl)-4,4'-bipiperidine-1-carboxylate | 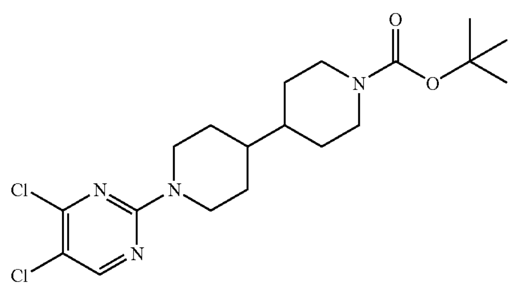 [SMILES: CC(C)(C)OC(=O)N1CCC(C2CCN(c3ncc(Cl)c(Cl)n3)CC2)CC1] | 315.0 (-Boc 100) |
| 3.5 | 3.1 | tert-butyl 1'-(4,6-dimethylpyrimidin-2-yl)-4,4'-bipiperidine-1-carboxylate | 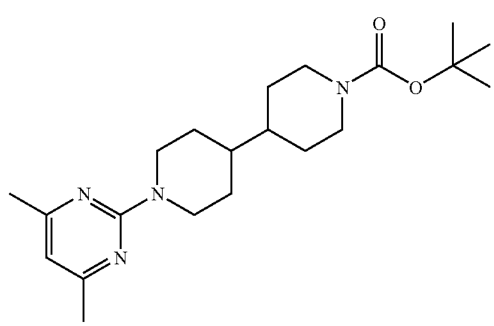 [SMILES: Cc1cc(C)nc(N2CCC(C3CCN(C(=O)OC(C)(C)C)CC3)CC2)n1] | 374.2 |
| 3.6 | 3.1 | 2,2,2-trifluoroethyl 1'-(5-fluoro-2-methylpyrimidin-4-yl)-4,4'-bipiperidine-1-carboxylate | 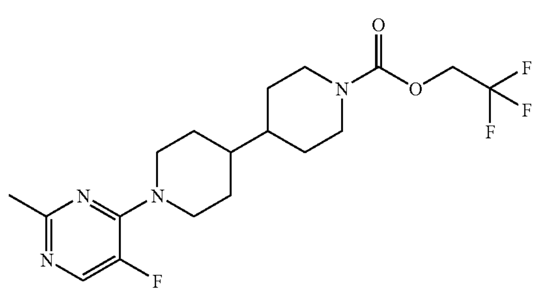 [SMILES: Cc1ncc(F)c(N2CCC(C3CCN(C(=O)OCC(F)(F)F)CC3)CC2)n1] | 405.11 |
| 3.7 | 3.1 | 2,2,2-trichloroethyl 1'-(5-fluoro-2-methylpyrimidin-4-yl)-4,4'-bipiperidine-1-carboxylate | 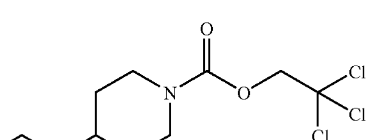 | 454.49 |

General Procedure 4.1:

Preparation of tert-butyl 1'-(6-methylpyrazin-2-yl)-4,4'-bipiperidine-1-carboxylate Step 1: tert-butyl 1'-[4-(methylsulfonyl)phenyl]-4,4'-bipiperidine-1-carboxylate: same as Procedure 2.1

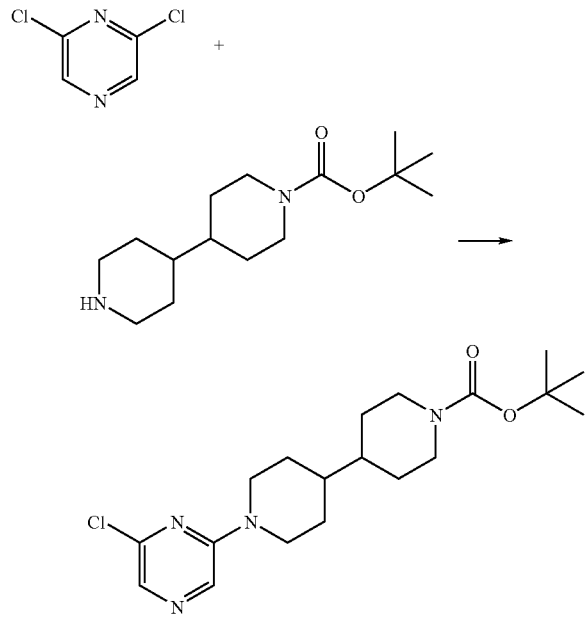

Step 2: tert-butyl 1'-(6-methylpyrazin-2-yl)-4,4'-bipiperidine-1-carboxylate

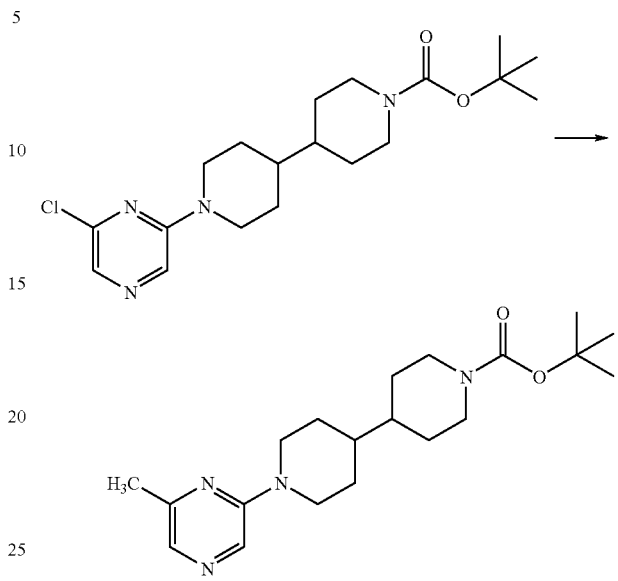

The tert-butyl 1'-[4-(methylsulfonyl)phenyl]-4,4'-bipiperidine-1-carboxylate (100 mg, 0.26 mmol) was dissolved in THF and NMP (5 mL, 1:1) at r.t. The catalyst iron (III) acetylacetonate (18.4 mg, 0.052 mmol) was added under $N_2$. Methyl magnesium bromide (3M, 0.19 mL, 0.57 mmol) was added dropwise. The reaction was stirred for more 15 min and was quenched with iced ammonia chloride solution (10 mL) and extracted with ethyl acetate (10 mL). The organic phase was washed with brine (10 mL, ×1), dried over magnesium sulfate, filtered, and concentrated on rotavapor. The crude material was purified by preparative TLC with 30% acetone: hexane to yield the title compound.

LC-MS: 361.63 (M+H).

Examples reported in Table 4 can be prepared by Procedure 4.1 described below.

TABLE 4

| Example | Procedure | Chemical name | Chemical Structure | (M + 1) |
|---|---|---|---|---|
| 4.1 | 4.1 | tert-butyl 1'-(6-methylpyrazin-2-yl)-4,4'-bipiperidine-1-carboxylate | 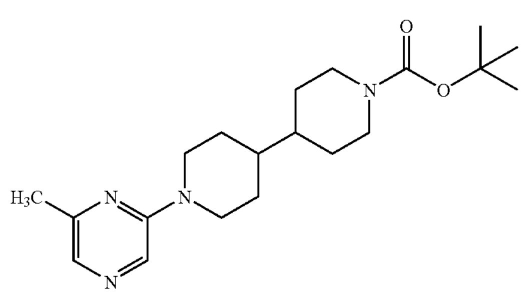 [SMILES: Cc1cncc(N2CCC(C3CCN(C(=O)OC(C)(C)C)CC3)CC2)n1] | 361.63 |

TABLE 4-continued

| Example | Procedure | Chemical name | Chemical Structure | (M + 1) |
|---|---|---|---|---|
| 4.2 | 4.1 | tert-butyl 1'-(6-methylpyrimidin-4-yl)-4,4'-bipiperidine-1-carboxylate | 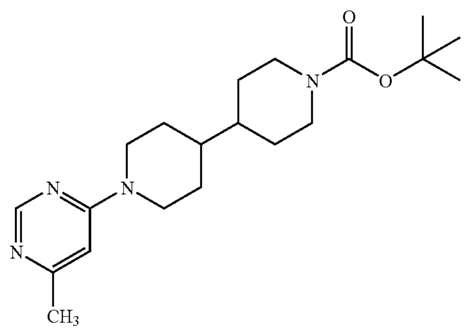 [SMILES: Cc1cc(N2CCC(C3CCN(C(=O)OC(C)(C)C)CC3)CC2)ncn1] | 361.45 |
| 4.3 | 4.1 | tert-butyl 1'-(6-cyclopropylpyrazin-2-yl)-4,4'-bipiperidine-1-carboxylate | 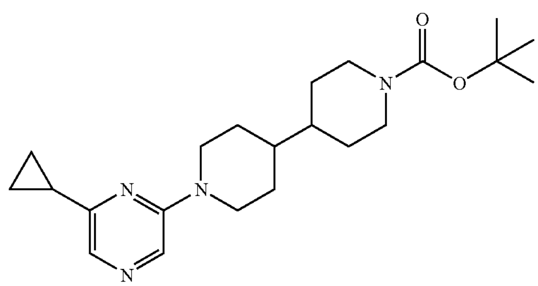 [SMILES: CC(C)(C)OC(=O)N1CCC(C2CCN(c3cncc(C4CC4)n3)CC2)CC1] | 378.13 |
| 4.4 | 4.1 | tert-butyl 1'-(5-fluoro-2-methylpyrimidin-4-yl)-4,4'-bipiperidine-1-carboxylate | 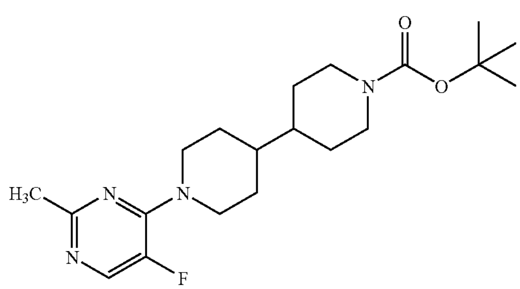 | 379.17 |
| 4.5 | 4.1 | tert-butyl 1'-(2,6-dimethylpyrimidin-4-yl)-4,4'-bipiperidine-1-carboxylate | 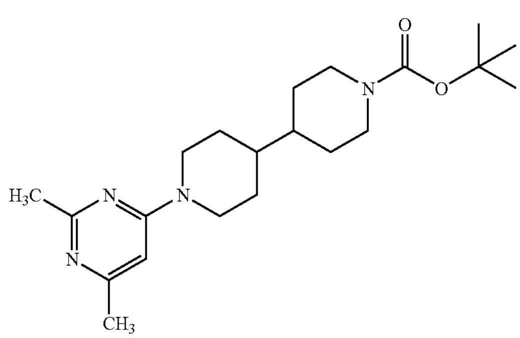 [SMILES: Cc1cc(N2CCC(C3CCN(C(=O)OC(C)(C)C)CC3)CC2)nc(C)n1] | 375.17 |
| 4.6 | 4.1 | tert-butyl 1'-(4,6-dimethylpyrimidin-2-yl)-4,4'-bipiperidine-1-carboxylate | 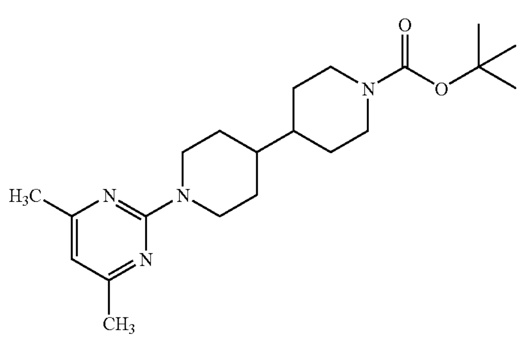 [SMILES: Cc1cc(C)nc(N2CCC(C3CCN(C(=O)OC(C)(C)C)CC3)CC2)n1] | 375.21 |
| 4.7 | 4.1 | tert-butyl 1'-(4-cyanopyridin-2-yl)-4,4'-bipiperidine-1- | 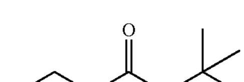 | 407.64 (M + 23) |

General Procedure 5.1:

Preparation of tert-butyl 1'-(6-cyanopyrazin-2-yl)-4,4'-bipiperidine-1-carboxylate Step 1: tert-butyl 1'-[4-(methylsulfonyl)phenyl]-4,4'-bipiperidine-1-carboxylate: same as Procedure 2.1

Step 2: tert-butyl 1'-(6-cyanopyrazin-2-yl)-4,4'-bipiperidine-1-carboxylate

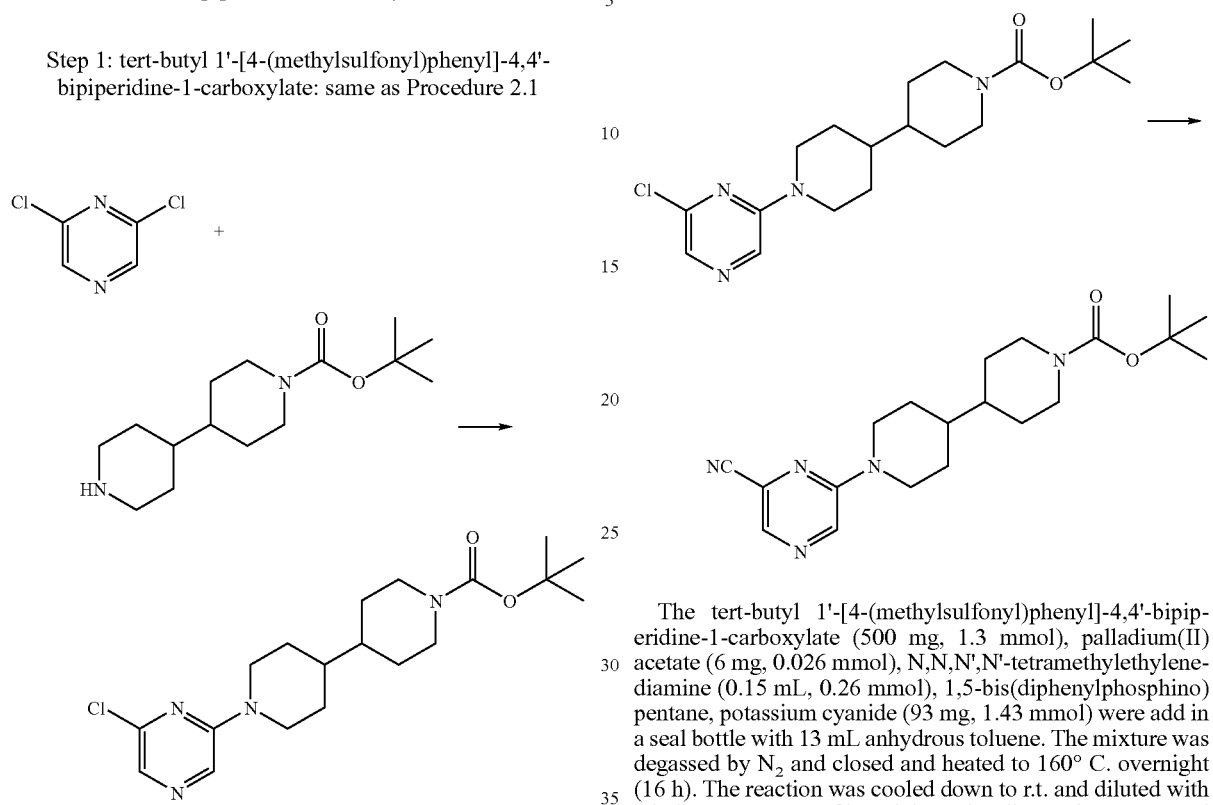

The tert-butyl 1'-[4-(methylsulfonyl)phenyl]-4,4'-bipiperidine-1-carboxylate (500 mg, 1.3 mmol), palladium(II) acetate (6 mg, 0.026 mmol), N,N,N',N'-tetramethylethylenediamine (0.15 mL, 0.26 mmol), 1,5-bis(diphenylphosphino)pentane, potassium cyanide (93 mg, 1.43 mmol) were add in a seal bottle with 13 mL anhydrous toluene. The mixture was degassed by $N_2$ and closed and heated to 160° C. overnight (16 h). The reaction was cooled down to r.t. and diluted with ethyl acetate 50 mL, filtered through celite, and concentrated on rotavapor. The crude material was purified by silica gel flash chromatography with 30% acetone: hexane to yield the title compound.

LC-MS: 394.11 (M+23).

Examples reported in Table 5 can be prepared by Procedure 5.1.

TABLE 5

| Example | Procedure | Chemical name | Chemical Structure | (M + 1) |
|---|---|---|---|---|
| 5.1 | 5.1 | tert-butyl 1'-(6-cyanopyrimidin-4-yl)-4,4'-bipiperidine-1-carboxylate | 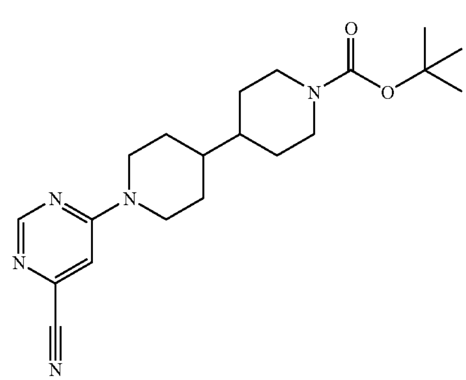 [SMILES: CC(C)(C)OC(=O)N1CCC(C2CCN(c3cc(C#N)ncn3)CC2)CC1] | 372.13 |

TABLE 5-continued

| Example | Procedure | Chemical name | Chemical Structure | (M + 1) |
|---|---|---|---|---|
| 5.2 | 5.1 | tert-butyl 1'-(2-cyanopyrimidin-4-yl)-4,4'-bipiperidine-1-carboxylate | 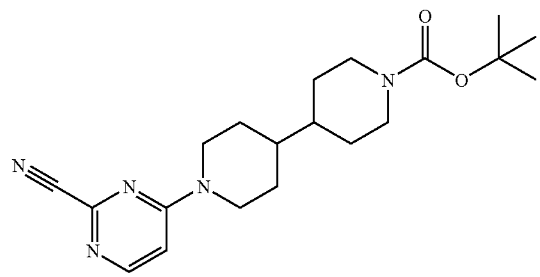 [SMILES: CC(C)(C)OC(=O)N1CCC(C2CCN(c3ccnc(C#N)n3)CC2)CC1] | 372.14 |
| 5.3 | 5.1 | tert-butyl 1'-(2-cyano-6-methylpyrimidin-4-yl)-4,4'-bipiperidine-1-carboxylate | 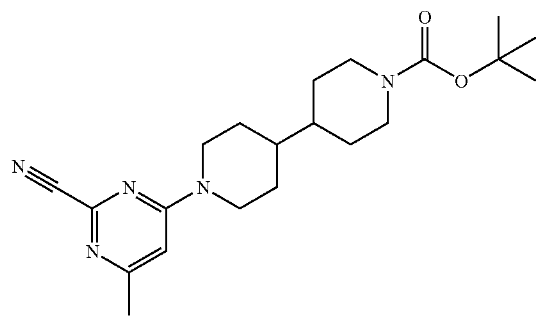 [SMILES: Cc1cc(N2CCC(C3CCN(C(=O)OC(C)(C)C)CC3)CC2)nc(C#N)n1] | 408.2 (M + 23) |
| 5.4 | 5.1 | tert-butyl 1'-[6-(aminocarbonyl)pyrimidin-4-yl]-4,4'-bipiperidine-1-carboxylate | 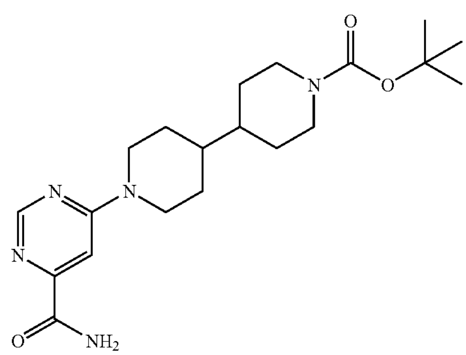 [SMILES: CC(C)(C)OC(=O)N1CCC(C2CCN(c3cc(C(N)=O)ncn3)CC2)CC1] | 390.20 |
| 5.5 | 5.1 | tert-butyl 1'-[2-(aminocarbonyl)pyrimidin-4-yl]-4,4'-bipiperidine-1-carboxylate | 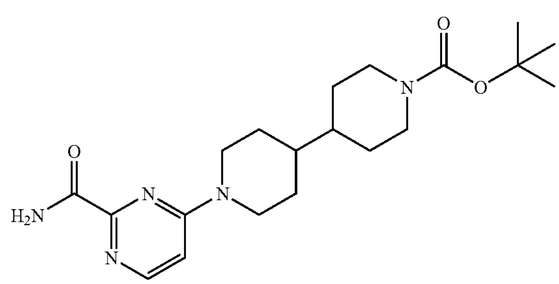 [SMILES: CC(C)(C)OC(=O)N1CCC(C2CCN(c3ccnc(C(N)=O)n3)CC2)CC1] | 390.20 |
| 5.6 | 5.1 | tert-butyl 1'-(6-cyanopyridin-2-yl)-4,4'-bipiperidine-1-carboxylate | 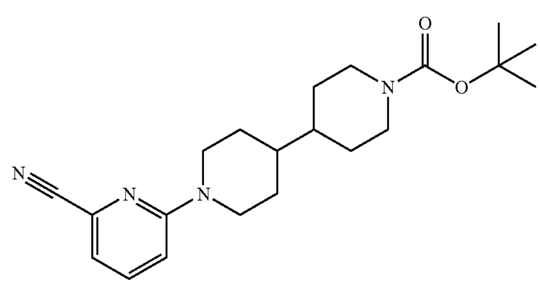 | 393.13 (M + 23) |
| 5.7 | 5.1 | tert-butyl 1'-(6-cyanopyrazin-2-yl)-4,4'-bipiperidine-1-carboxylate | 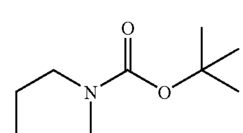 | 394.11 (M + 23) |

General Procedure 6.1:

Preparation of tert-butyl 1'-[6-(1H-1,2,4-triazol-1-yl)pyrimidin-4-yl]-4,4'-bipiperidine-1-carboxylate Step 1: tert-butyl 1'-(6-chloropyrimidin-4-yl)-4,4'-bipiperidine-1-carboxylate: same as Procedure 2.1

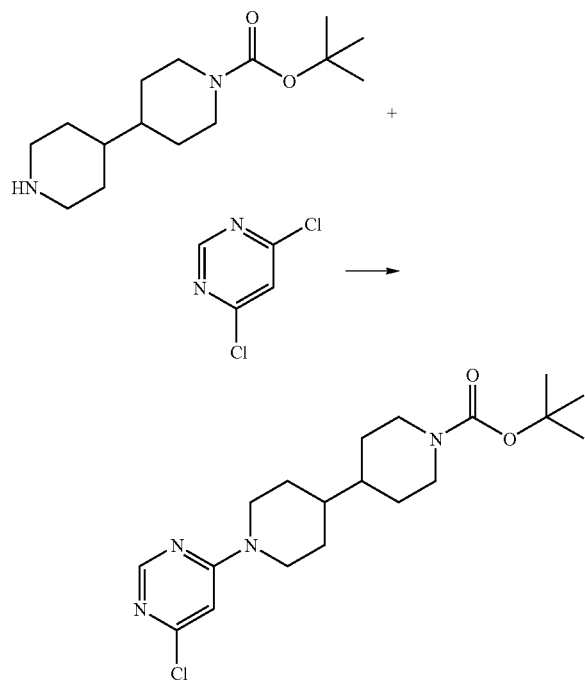

Step 2: tert-butyl 1'-[6-(1H-1,2,4-triazol-1-yl)pyrimidin-4-yl]-4,4'-bipiperidine-1-carboxylate

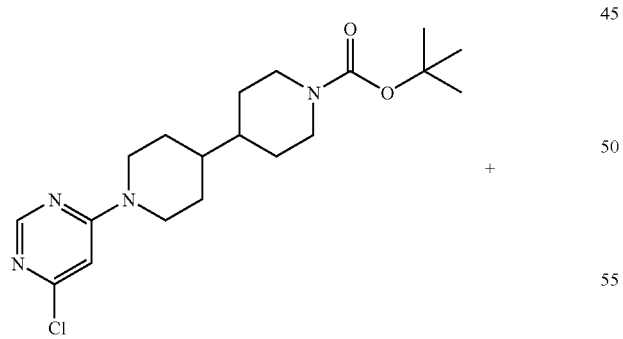

+

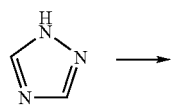

→

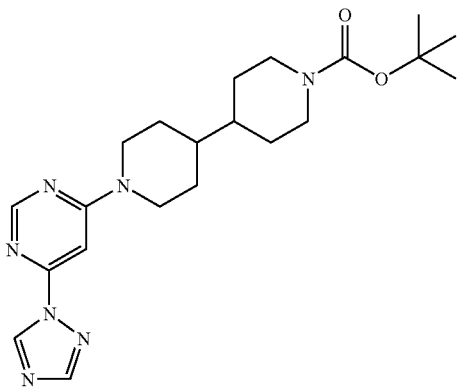

The tert-butyl 1'-(6-chloropyrimidin-4-yl)-4,4'-bipiperidine-1-carboxylate (190 mg, 0.50 mmol), 1,2,4-triazole (69 mg, 1.0 mmol), cesium carbonate (488 mg, 1.5 mmol) were added in NMP (5 mL) and heated to 140° C. for 1.5 hours. The reaction crude were cooled down to r.t. and diluted with ethyl acetate (10 mL), washed with water (5 mL, ×1) and brine (5 mL, ×1). The organic phase was dried over magnesium sulfate, filtered and concentrated on rotavapor. The crude mixture was purified by preparative TLC with 50% ethyl acetate:hexane to yield the title compound.

LC-MS: 414.13 (M+H).

Examples reported in Table 6 can be prepared by Procedure 6.1 described below.

TABLE 6

| Example | Procedure | Chemical name | Chemical Structure | (M + 1) |
|---|---|---|---|---|
| 6.1 | 6.1 | tert-butyl 1'-[6-(1H-pyrazol-1-yl)pyrimidin-4-yl]-4,4'-bipiperidine-1-carboxylate | 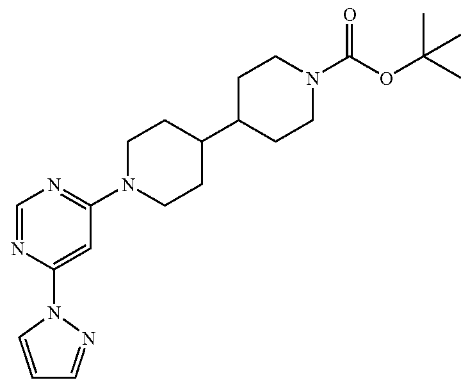 [SMILES: CC(C)(C)OC(=O)N1CCC(C2CCN(c3cc(-n4cccn4)ncn3)CC2)CC1] | 413.21 |
| 6.2 | 6.1 | tert-butyl 1'-[6-(1H-1,2,3-triazol-1-yl)pyrimidin-4-yl]-4,4'-bipiperidine-1-carboxylate | 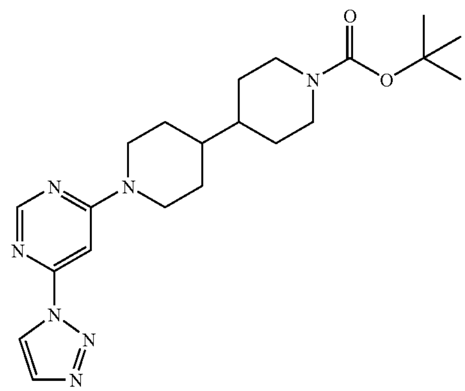 [SMILES: CC(C)(C)OC(=O)N1CCC(C2CCN(c3cc(-n4ccnn4)ncn3)CC2)CC1] | 414.11 |
| 6.3 | 6.1 | tert-butyl 1'-[6-(2H-1,2,3-triazol-2-yl)pyrimidin-4-yl]-4,4'-bipiperidine-1-carboxylate | 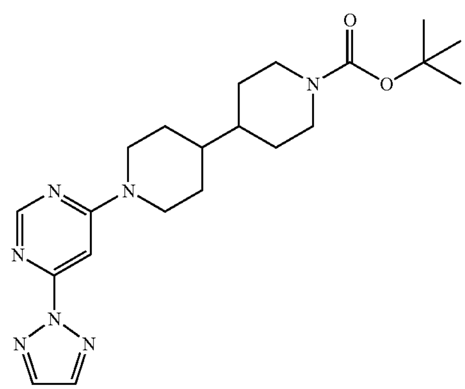 [SMILES: CC(C)(C)OC(=O)N1CCC(C2CCN(c3cc(-n4nccn4)ncn3)CC2)CC1] | 414.14 |
| 6.4 | 6.1 | tert-butyl 1'-[6-(1H-1,2,4-triazol-1-yl)pyrimidin-4-yl]-4,4'-bipiperidine-1-carboxylate | 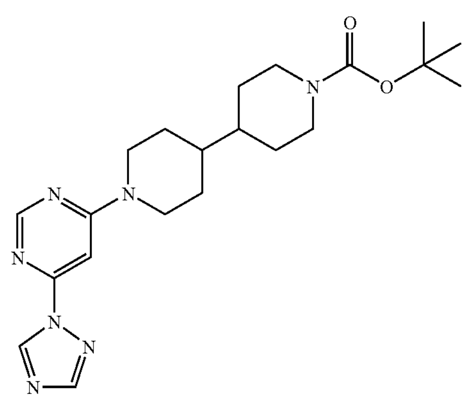 [SMILES: CC(C)(C)OC(=O)N1CCC(C2CCN(c3cc(-n4cncn4)ncn3)CC2)CC1] | 414.13 |

General Procedure 7.1:

Preparation of tert-butyl 1'-[6-(methylamino)pyrimidin-4-yl]-4,4'-bipiperidine-1-carboxylate Step 1: tert-butyl 1'-(6-chloropyrimidin-4-yl)-4,4'-bipiperidine-1-carboxylate: same as Procedure 2.1

Step 2: tert-butyl 1'-[6-(methylamino)pyrimidin-4-yl]-4,4'-bipiperidine-1-carboxylate The tert-butyl 1'-(6-chloropyrimidin-4-yl)-4,4'-bipiperidine-1-carboxylate (19 mg, 0.05 mmol) was added to methyl amine in MeOH (1N, 2 mL) in a sealed bottle and heated to 50° C. for 2 days. The reaction crude were cooled down to r.t. and concentrated on rotavapor. The crude mixture was purified by preparative TLC with 10% methanol: dichloromethane to yield title compound.

LC-MS: 376.18 (M+H)

Examples reported in Table 7 can be prepared by Procedure 7.1 described below.

TABLE 7

| Example | Procedure | Chemical name | Chemical Structure | (M+1) |
|---|---|---|---|---|
| 7.1 | 7.1 | tert-butyl 1'-[6-(methylamino)pyrimidin-4-yl]-4,4'-bipiperidine-1-carboxylate | 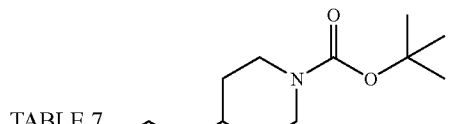 | 376.18 |
| 7.2 | 7.1 | tert-butyl 1'-[2-(methylamino)pyrimidin-4-yl]-4,4'-bipiperidine-1-carboxylate | 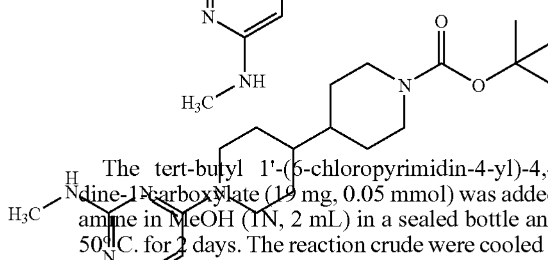 | 376.18 |

General Procedure 8.1:

Preparation of tert-butyl 1'-[6-(benzyloxy)pyrimidin-4-yl]-4,4'-bipiperidine-1-carboxylate Step 1: tert-butyl 1'-(6-chloropyrimidin-4-yl)-4,4'-bipiperidine-1-carboxylate: same as Procedure 2.1

Step 2: Preparation of tert-butyl 1'-[6-(benzyloxy)pyrimidin-4-yl]-4,4'-bipiperidine-1-carboxylate

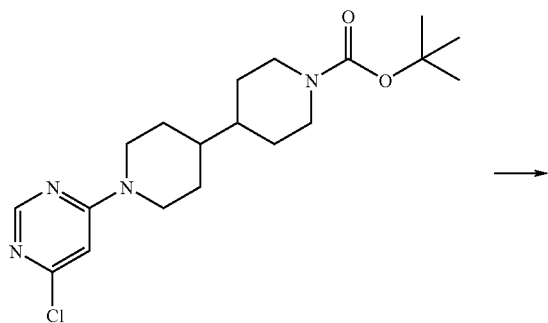

→

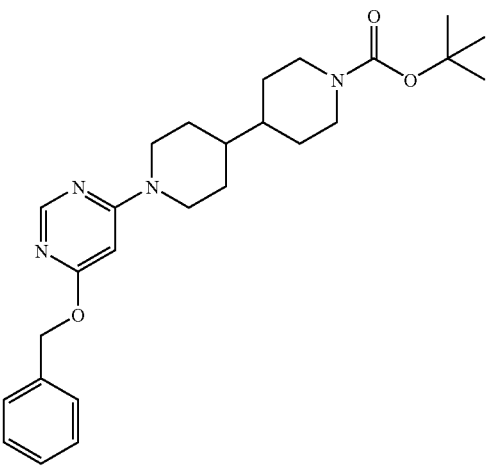

The tert-butyl 1'-(6-chloropyrimidin-4-yl)-4,4'-bipiperidine-1-carboxylate (100 mg, 0.26 mmol), phenylmethanol (0.031 mL, 0.29 mmol) were added to DMF (2.6 mL), and then sodium hydride (7 mg, 0.29 mmol) was added to the mixture. The reaction was heated to 30° C. for 30 min The reaction crude was cooled down to r.t. and quenched with ice ammonia chloride solution (10 mL) and extracted with ethyl acetate (10 mL). The organic phase was washed with brine (10 mL, ×1), dried over magnesium sulfate, filtered and concentrated by rotavapor. The crude mixture was purified by preparative TLC with 30% ethylacetate:hexane to yield the title compound.

LC-MS: 453.62 (M+H).

Examples reported in Table 8 can be prepared by Procedure 8.1 described below.

TABLE 8

| Example | Procedure | Chemical name | Chemical Structure | (M + 1) |
|---|---|---|---|---|
| 8.1 | 8.1 | tert-butyl 1'-[6-(benzyloxy)pyrazin-2-yl]-4,4'-bipiperidine-1-carboxylate | 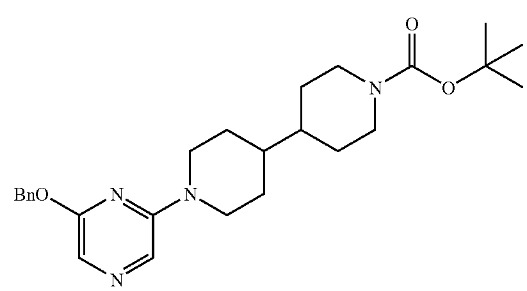 [SMILES: CC(C)(C)OC(=O)N1CCC(C2CCN(c3cncc(OCc4ccccc4)n3)CC2)CC1] | 453.62 |
| 8.2 | 8.1 | tert-butyl 1'-[6-(benzyloxy)pyrimidin-4-yl]-4,4'-bipiperidine-1-carboxylate | 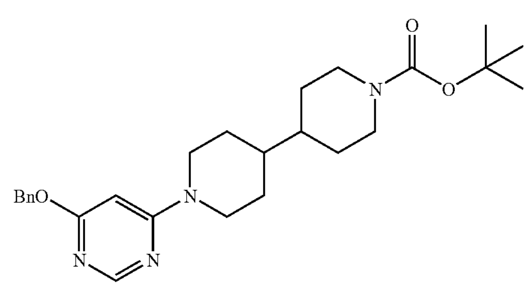 [SMILES: CC(C)(C)OC(=O)N1CCC(C2CCN(c3cc(OCc4ccccc4)ncn3)CC2)CC1] | 453.62 |

TABLE 8-continued

| Example | Procedure | Chemical name | Chemical Structure | (M + 1) |
|---|---|---|---|---|
| 8.3 | 8.1 | tert-butyl 1'-[2-(benzyloxy)pyrimidin-4-yl]-4,4'-bipiperidine-1-carboxylate | 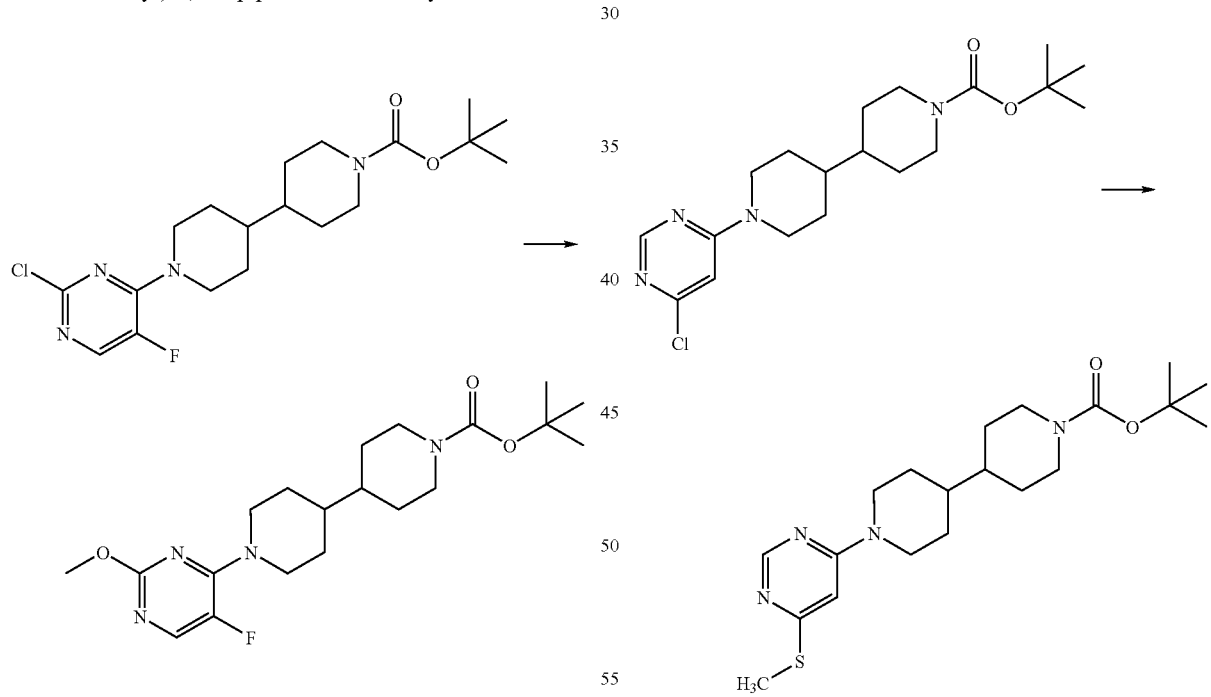 | 453.62 |

General Procedure 9.1:

Preparation of tert-butyl 1'-(5-fluoro-2-methoxypyrimidin-4-yl)-4,4'-bipiperidine-1-carboxylate Step 1: tert-butyl 1'-(2-chloro-5-fluoropyrimidin-4-yl)-4,4'-bipiperidine-1-carboxylate: same as Procedure 2.1

Step 2: tert-butyl 1'-(5-fluoro-2-methoxypyrimidin-4-yl)-4,4'-bipiperidine-1-carboxylate General Procedure 10.1:

Preparation of tert-butyl 1'-[6-(methylsulfonyl)pyrimidin-4-yl]-4,4'-bipiperidine-1-carboxylate Step 1: tert-butyl 1'-(6-chloropyrimidin-4-yl)-4,4'-bipiperidine-1-carboxylate: same as Procedure 2.1

Step 2: tert-butyl 1'-[6-(methylthio)pyrimidin-4-yl]-4,4'-bipiperidine-1-carboxylate

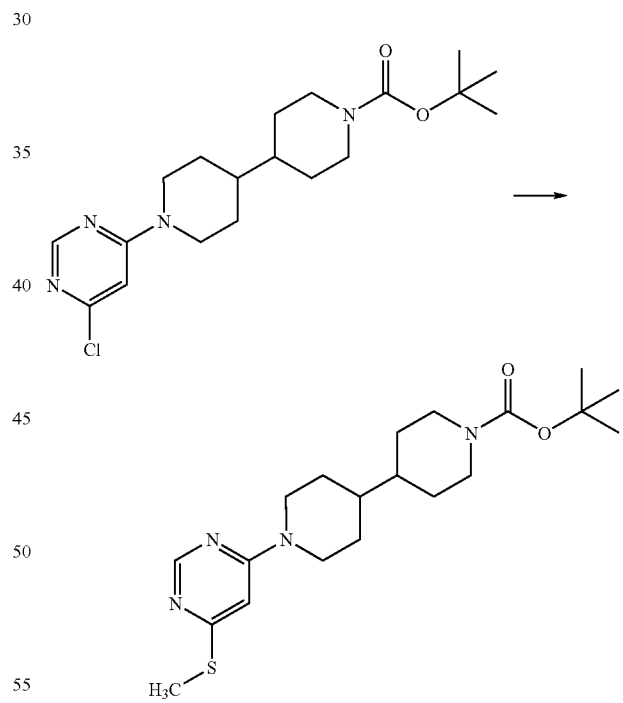

The tert-butyl 1'-(2-chloro-5-fluoropyrimidin-4-yl)-4,4'-bipiperidine-1-carboxylate (40 mg, 0.10 mmol) was added to NMP (1 mL), and then potassium methoxide (8.1 mg, 0.11 mmol) was added to the mixture. The reaction was stirred for 30 min at r.t. and was quenched with ammonium chloride solution (5 mL), extracted with ethylacetate (10 mL). The organic phase was washed with brine (10 mL, ×1), dried over magnesium sulfate, filtered and concentrated by rotavapor. The crude mixture was purified by preparative TLC with 30% acetone:hexane to yield the title compound.

LC-MS: 395.14 (M+H).

The tert-butyl 1'-(6-chloropyrimidin-4-yl)-4,4'-bipiperidine-1-carboxylate (100 mg, 0.26 mmol) was dissolved in NMP (2.6 mL), and sodium methanethiolate (18.2 mg, 0.26 mmol) was added. The reaction was stirred at r.t. for 30 min. The reaction crude was diluted with ethyl acetate (10 mL) and was washed with water (10 mL, ×1) and brine (10 mL, ×1), dried over magnesium sulfate, filtered and concentrated by rotavapor. The crude mixture was purified by preparative TLC with 30% ethylacetate:hexane to yield the title compound.

LC-MS: 393.64 (M+H).

Step 3: tert-butyl 1'-[6-(methylsulfonyl)pyrimidin-4-yl]-4,4'-bipiperidine-1-carboxylate.

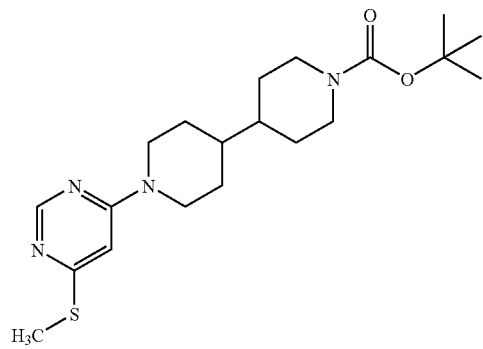 [SMILES: CSc1cc(N2CCC(C3CCN(C(=O)OC(C)(C)C)CC3)CC2)ncn1]

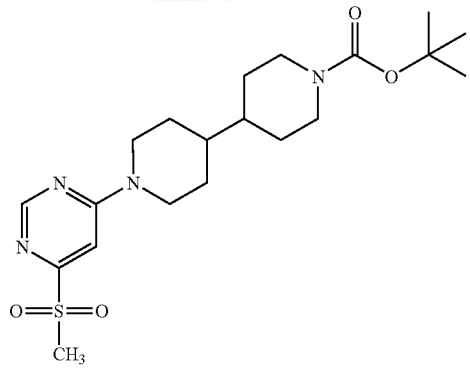

The tert-butyl 1'-[6-(methylthio)pyrimidin-4-yl]-4,4'-bipiperidine-1-carboxylate (100 mg, 0.25 mmol) was dissolved in dichloromethane (2.5 mL) and mCPBA was added (126 mg, 0.55 mmol, max 77%). The reaction was stirred at r.t. for 1 h and was diluted with dichloromethane (10 mL). The reaction mixture was washed with sodium thiosulfate solution (10 mL, 1N, 1×) and saturated sodium bicarbonate solution (10 mL, ×1). The organic phase was dried over magnesium sulfate, filtered and concentrated by rotavapor. The crude mixture was purified by flash silica gel column chromatography with 30% acetone:hexane to yield the title compound.

LCMS: 447.58 (M+23).

Examples reported in Table 10 can be prepared by Procedure 10.1 described below.

TABLE 10

| Example | Procedure | Chemical name | Chemical structure | (M+1) |
|---------|-----------|---------------|--------------------|-------|
| 10.1 | 10.1 | tert-butyl 1'-[6-(methylthio)pyrimidin-4-yl]-4,4'-bipiperidine-1-carboxylate | 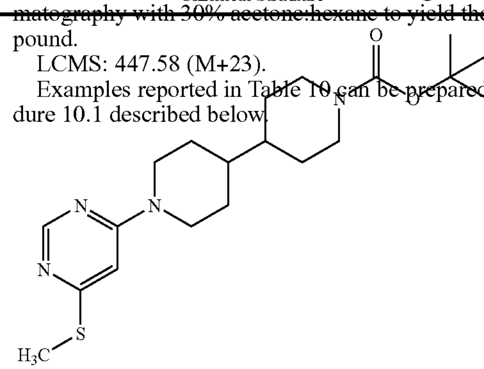 | 393.64 |
| 10.2 | 10.1 | tert-butyl 1'-[6-(methylsulfonyl)pyrimidin-4-yl]-4,4'-bipiperidine-1-carboxylate | 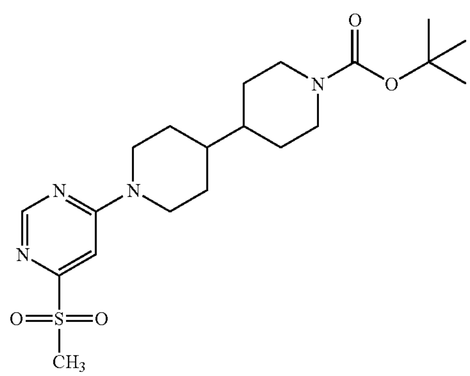 [SMILES: CC(C)(C)OC(=O)N1CCC(C2CCN(c3cc(S(C)(=O)=O)ncn3)CC2)CC1] | 447.58 |

General Procedure 11.1 (Nucleophilic Aromatic Substitution)

EXAMPLE 11.1 tert-butyl 1'-(6-chloropyrazin-2-yl)-4,4'-bipiperidine-1-carboxylate

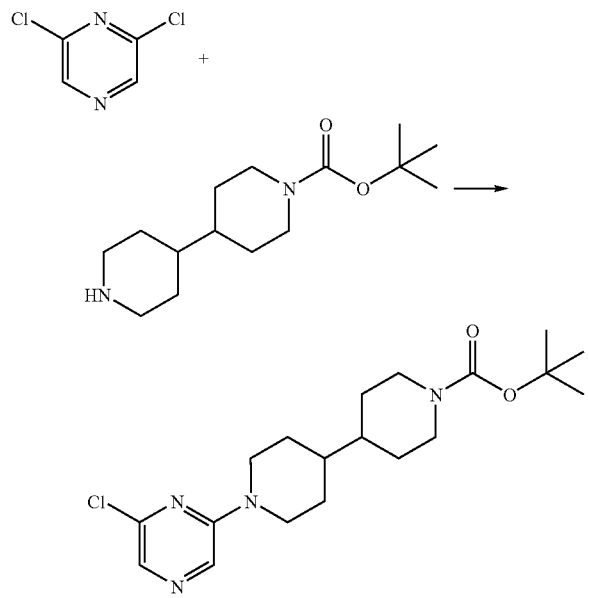

The tert-butyl 4,4'-bipiperidine-1-carboxylate (100 mg, 0.45 mmol) and cesium carbonate (364 mg, 1.1 mmol) were slurried in NMP (0.75 ml) and the 2,6-dichloropyrazine (67 mg, 0.45 mmol) added. The mixture was stirred at 70 C overnight. The slurry was diluted with 15% saturated sodium bicarbonate:water (40 ml) and extracted with DCM (3×25 ml). The combined organic fraction was washed with 4:1 water:saturated sodium bicarbonate (2×), brine, dried over magnesium sulfate, filtered, and the volatiles removed in vac. The crude material was purified by chromatography on silica gel with 20% acetone:hexanes to yield the title compound.
LRMS calc: 380.2. obs: 403.0 (M+Na).

General Procedure 11.2 (Chlorination)

EXAMPLE 11.2 tert-butyl 1'-(5-chloropyrazin-2-yl)-4,4'-bipiperidine-1-carboxylate

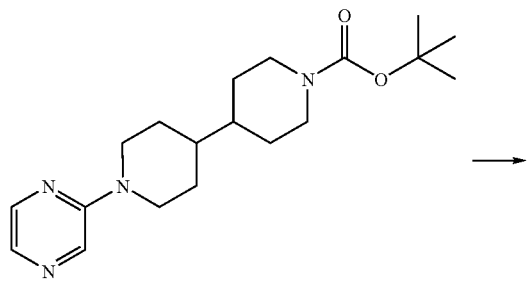

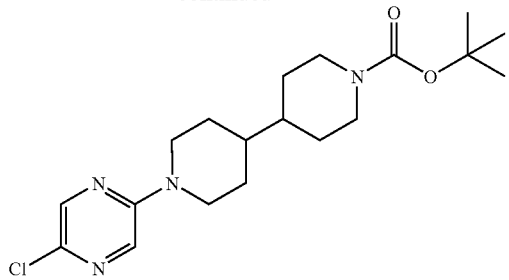

The tert-butyl 1'-pyrazin-2-yl-4,4'-bipiperidine-1-carboxylate (64 mg, 0.19 mmol, prepared as described for Example 8) and N-chlorosuccinimide (27 mg, 0.20 mmol) were dissolved in DMF (0.9 ml) and the solution stirred overnight at 50 C. The slurry was diluted with 15% brine:water (40 ml) and extracted with ethyl acetate (3×25 ml). The combined organic fraction was washed with brine, dried over magnesium sulfate, filtered, and the volatiles removed in vac. The crude material was purified by chromatography on silica gel with 10% acetone:hexanes to yield the title compound.
LRMS calc: 380.2. obs: 403.0 (M+Na).

General Procedure 11.3 (Bromination)

EXAMPLE 11.15 tert-butyl 1'-(5-bromopyrazin-2-yl)-4,4'-bipiperidine-1-carboxylate

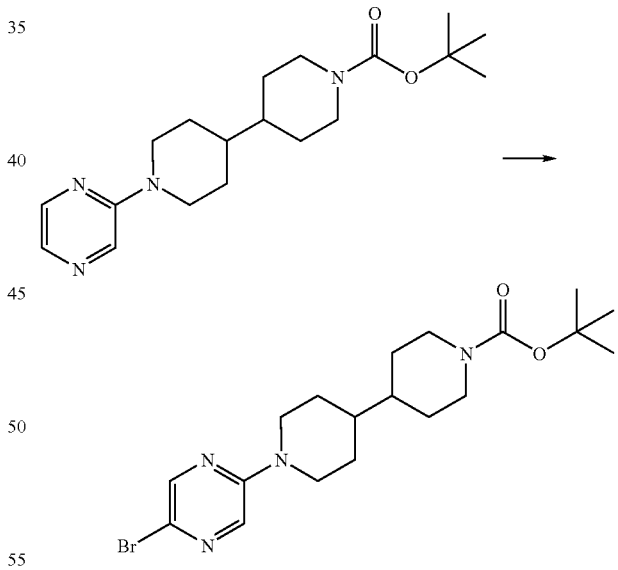

The tert-butyl 1'-pyrazin-2-yl-4,4'-bipiperidine-1-carboxylate (16 mg, 0.046 mmol, prepared as described for Example 8) and N-bromosuccinimide (8.2 mg, 0.046 mmol) were dissolved in DMF (0.2 ml) and the solution stirred overnight at 50 C. The slurry was diluted with 15% brine:water (40 ml) and extracted with ethyl acetate (3×25 ml). The combined organic fraction was washed with brine, dried over magnesium sulfate, filtered, and the volatiles removed in vac. The crude material was purified by chromatography on silica gel with 20% acetone:hexanes to yield the title compound.
LRMS calc: 424.1. obs: 447.0 (M+Na).

Examples reported in Table 11 can be prepared using general procedure 11.1 from readily available starting materials and tert-butyl 4,4'-bipiperidine-1-carboxylate.

TABLE 11

| Ex. # | Procedure | Chemical name | Chemical Structure | (M + 1) |
|---|---|---|---|---|
| 11.1 | 11.1 | tert-butyl 1'-(1,3-thiazol-2-yl)-4,4'-bipiperidine-1-carboxylate | 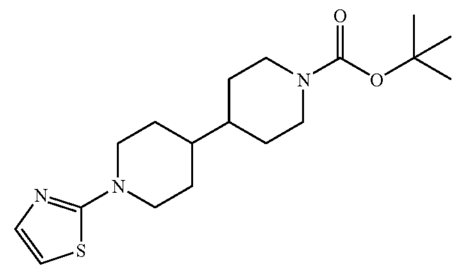 [SMILES: CC(C)(C)OC(=O)N1CCC(C2CCN(c3nccs3)CC2)CC1] | 352.0 |
| 11.2 | 11.1 | tert-butyl 1'-pyridin-2-yl-4,4'-bipiperidine-1-carboxylate | 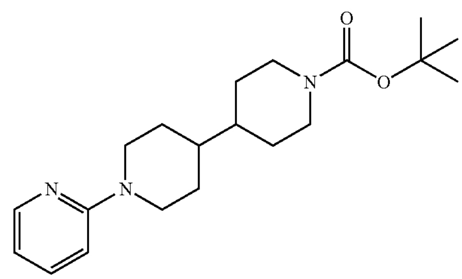 [SMILES: CC(C)(C)OC(=O)N1CCC(C2CCN(c3ccccn3)CC2)CC1] | 346.1 |
| 11.3 | 11.1 | tert-butyl-1'-(5-methylpyridin-2-yl)-4,4'-bipiperidine-1-carboxylate | 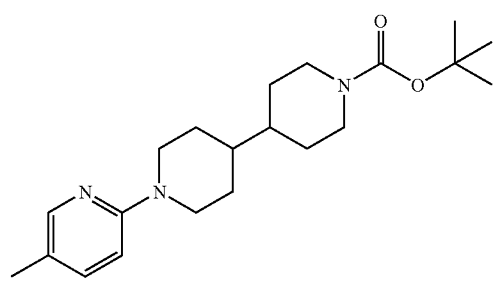 [SMILES: Cc1ccc(N2CCC(C3CCN(C(=O)OC(C)(C)C)CC3)CC2)nc1] | |
| 11.4 | 11.1 | tert-butyl 1'-pyrazin-2-yl-4,4'-bipiperidine-1-carboxylate | 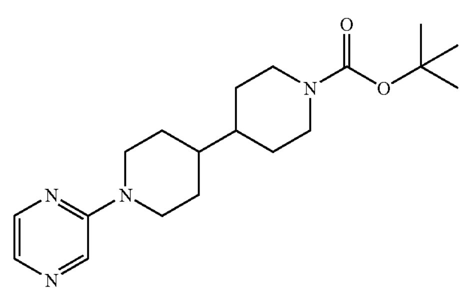 [SMILES: CC(C)(C)OC(=O)N1CCC(C2CCN(c3cnccn3)CC2)CC1] | 369.08 (M + Na) |
| 11.5 | 11.1 | tert-butyl 1'-pyrimidin-2-yl-4,4'-bipiperidine-1-carboxylate | 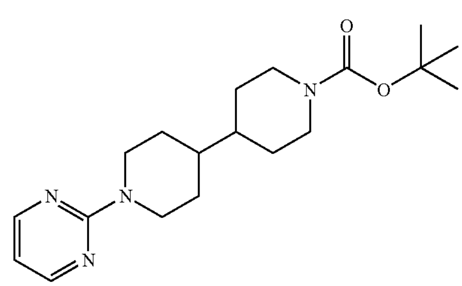 [SMILES: CC(C)(C)OC(=O)N1CCC(C2CCN(c3ncccn3)CC2)CC1] | 347.0 |

TABLE 11-continued

| Ex. # | Procedure | Chemical name | Chemical Structure | (M + 1) |
|---|---|---|---|---|
| 11.6 | 11.1 | tert-butyl 1'-(6-cyano-2-methylpyrimidin-4-yl)-4,4'-bipiperidine-1-carboxylate | 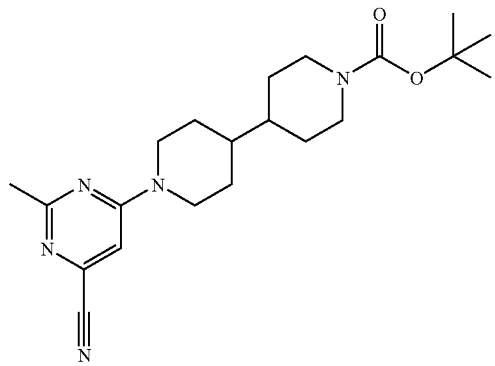 [SMILES: Cc1nc(C#N)cc(N2CCC(C3CCN(C(=O)OC(C)(C)C)CC3)CC2)n1] | 386.4 |
| 11.7 | 11.1 | tert-butyl 1'-(1,3-benzothiazol-2-yl)-4,4'-bipiperidine-1-carboxylate | 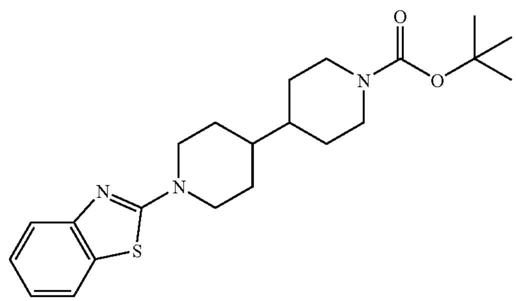 [SMILES: CC(C)(C)OC(=O)N1CCC(C2CCN(c3nc4ccccc4s3)CC2)CC1] | 402.1 |
| 11.8 | 11.1 | tert-butyl 1'-(5-bromo-1,3-thiazol-2-yl)-4,4'-bipiperidine-1-carboxylate | 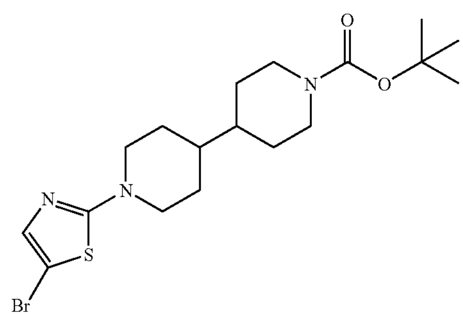 [SMILES: CC(C)(C)OC(=O)N1CCC(C2CCN(c3ncc(Br)s3)CC2)CC1] | 430.0 |
| 11.9 | 11.1 | tert-butyl 1'-(6-chloropyrimidin-4-yl)-4,4'-bipiperidine-1-carboxylate | 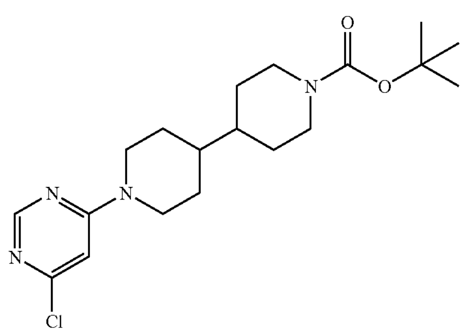 [SMILES: CC(C)(C)OC(=O)N1CCC(C2CCN(c3cc(Cl)ncn3)CC2)CC1] | 381.0 |
| 11.10 | 11.1 | tert-butyl 1'-quinoxalin-2-yl-4,4'-bipiperidine-1-carboxylate | 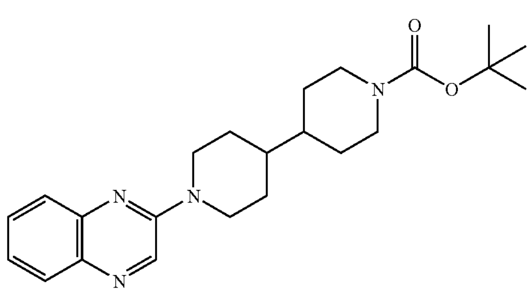 [SMILES: CC(C)(C)OC(=O)N1CCC(C2CCN(c3cnc4ccccc4n3)CC2)CC1] | 397.1 |
| 11.11 | 11.1 | tert-butyl 1'-(3- | 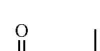 | 383.1 |

General Procedure 11.6 (Dechlorination)

EXAMPLE 11.16 tert-butyl 1'-pyrimidin-4-yl-4,4'-bipiperidine-1-carboxylate

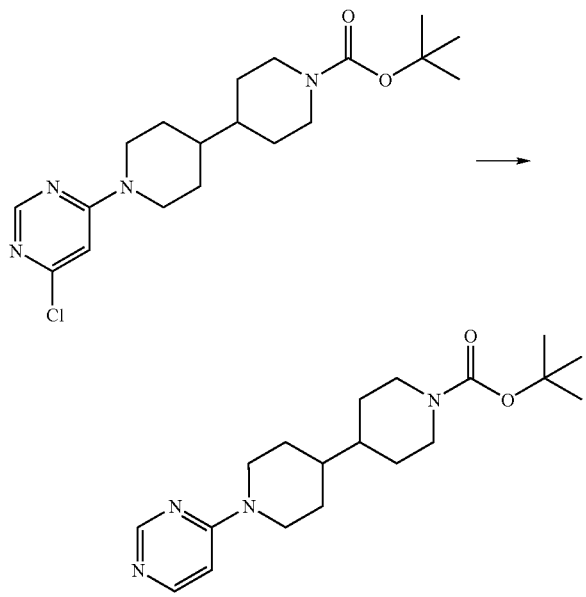

The tert-butyl 1'-(6-chloropyrimidin-4-yl)-4,4'-bipiperidine-1-carboxylate (50 mg, 0.13 mmol, prepared as described for Example 13) and sodium acetate (11 mg, 0.13 mmol) were dissolved in methanol (1.3 ml), 10% palladium on carbon (14 mg) added and the solution stirred overnight under a hydrogen atmosphere. The solution was diluted with 4:1 water: saturated sodium bicarbonate (40 ml) and extracted with ethyl acetate (3×25 ml). The combined organic fraction was washed with brine, dried over magnesium sulfate, filtered, and the volatiles removed in vac. The crude material was purified by chromatography on silica gel with 35% acetone: hexanes to yield the titled compound.

LRMS calc: 346.2. obs: 347.1 (M+H).

General Procedure 12.1 (Nucleophilic Aromatic Substitution)

EXAMPLE 12.1

Preparation of tert-butyl-1'-[4-(cyano)phenyl]-4,4'-bipiperidine-1-carboxylate

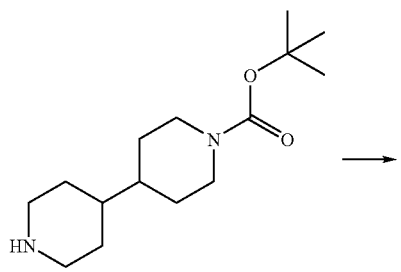

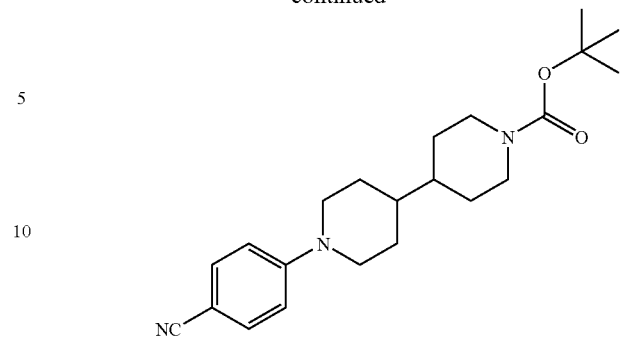

A solution of tert-butyl 4,4'-bipiperidine-1-carboxylate (181 mg; 0.674 mmol) in DMF (3 mL) was treated with 4-fluorobenzonitrile (98 mg; 0.809 mmol) and cesium carbonate (264 mg; 0.809 mmol). The mixture was stirred at 70° C. for 18 hr. The mixture was partitioned between isopropyl acetate (25 mL) and pH7 phosphate buffer (10 mL). The organic was washed twice more with pH7 phosphate buffer (2×10 mL). The organic was dried over magnesium sulfate, filtered and evaporated to a solid. The crude product was chromatographed over silica gel (PTLC; 2:1 hex/MTBE). The major band was recovered affording the title compound. LRMS calc: 369.2. obs: 370.1 (M+H), 270.1 (M-BOC+H).

General Procedure 12.2 (Copper Mediated N-arylation)

EXAMPLE 12.2

Preparation of tert-butyl 1'-[4-(methylthio)phenyl]-4,4'-bipiperidine-1-carboxylate

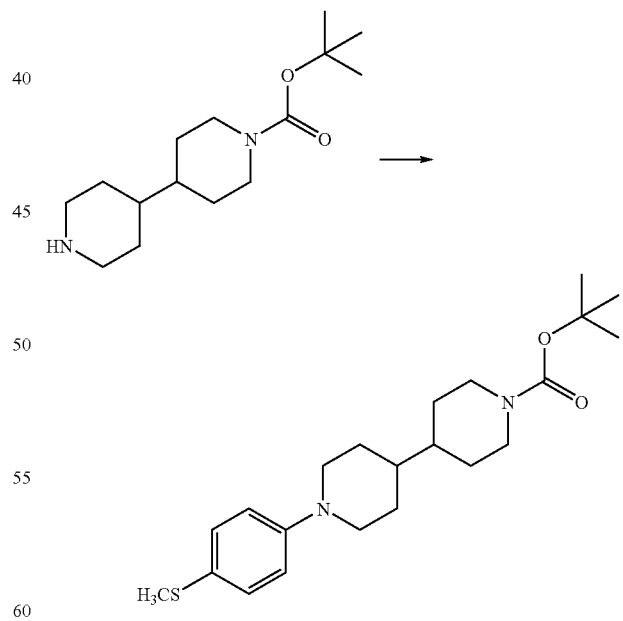

A suspension of 4-methylthiophenylboronic acid (240 mg; 1.431 mmol) in dichloromethane (6 mL) was treated with activated powdered 4 Å molecular sieves (1.5 g), Cu(OAc)$_2$ (87 mg; 0.477 mmol), tert-butyl 4,4'-bipiperidine-1-carboxylate (128 mg; 0.477 mmol) and triethylamine (134 µL; 0.954 mmol). The reaction vessel was purged with oxygen and the mixture stirred under an oxygen atmosphere at ambient temperature for 18 hr. The now brown mixture was filtered through Celite. The eluant was adsorbed onto silica gel. The silica gel was exhaustively eluted without fractionation (1:1 hex/MTBE). The eluant was evaporated to a yellow oil and chromatographed (PTLC; 2:1 hex/MTBE). The major band was collected affording the title compound. LRMS calc: 390.2. obs: 391.1 (M+H), 291.1 (M-BOC+H).

General Procedure 12.3 (Palladium Mediated N-arylation)

EXAMPLE 12.3

Preparation of tert-Butyl-1'-[4-(methoxycarbonyl)phenyl]-4,4'-bipiperidine-1-carboxylate General Procedure 12.4 (Ester Hydrolysis)

EXAMPLE 12.4

Preparation of 4-[1'-(tert-butoxycarbonyl)-4,4'-bipiperidin-1-yl]benzoic acid

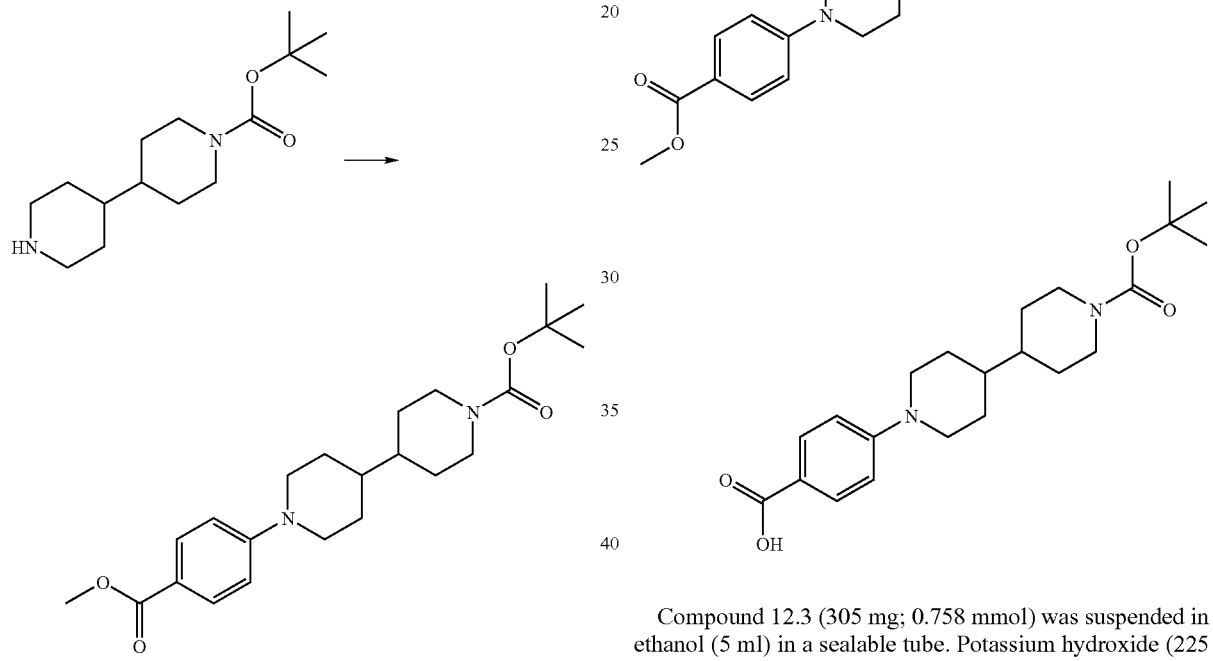

A 100 mL reaction flask was charged with tert-butyl 4,4'-bipiperidine-1-carboxylate (1.14 g; 4.25 mmol), methyl 4-bromobenzoate (913 mg; 4.25 mmol), cesium carbonate (4.15 g; 12.74 mmol), Pd(OAc)$_2$ (48 mg; 0.212 mmol) and 2-(diphenylphosphino)-2'-(N-N-dimethylamino)biphenyl (162 mg; 0.425 mmol). NMP (outgassed by bubbling with nitrogen for 10 min; 10 mL) was added and the mixture stirred at 90° C. for 18 hr. The mixture was diluted with dichloromethane (100 mL) and filtered through Celite. The filtrate was washed with water (4×25 mL). The organic was dried over magnesium sulfate, filtered and evaporated to a solid. The solid was digested at reflux (MTBE). After cooling, the white solid was recovered by filtration. The filtrate was evaporated and chromatographed (Horizon; 0% to 100% EtOAc/hex; linear gradient). The fractions containing the desired compound were recovered and combined with the solid to give the title compound.

LRMS calc: 402.3. obs: 403.2 (M+H), 303.2 (M-BOC+H).

Compound 12.3 (305 mg; 0.758 mmol) was suspended in ethanol (5 ml) in a sealable tube. Potassium hydroxide (225 mg; 3.41 mmol) was added. The tube was sealed and heated in a 105° C. bath for 1 hr. The solid mass was washed out with water and the pH adjusted to 4.0 with 1N HCl. The title compound was recovered by filtration. LRMS calc: 388.2. obs: 389.2 (M+H), 289.1 (M-BOC+H).

General Procedure 12.5 (Amide Formation)

EXAMPLE 12.5

Preparation of tert-Butyl-1'-{4-[(1,2,4-thiadiazol-5-ylamino)carbonyl]phenyl}-4,4'-bipiperidine-1-carboxylate

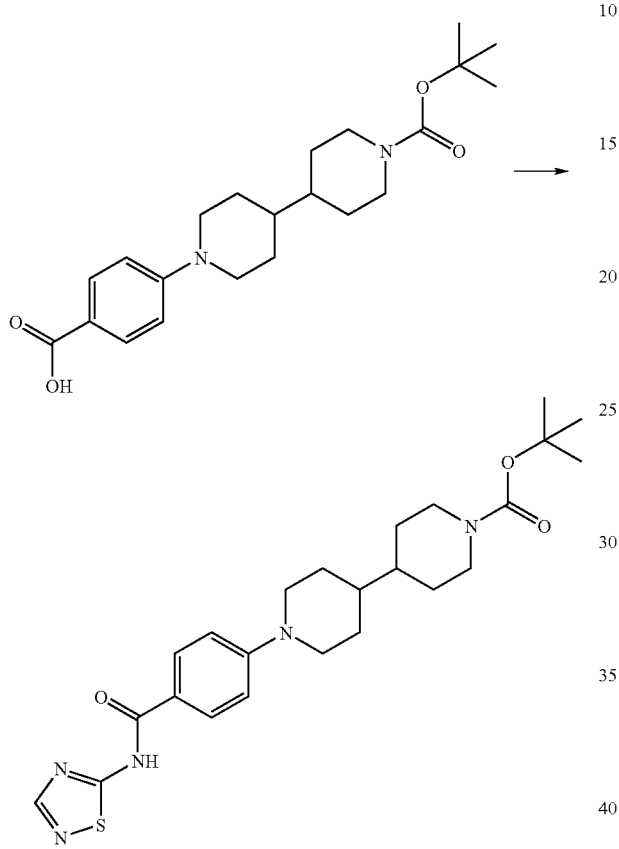

Compound 12.4 (56 mg; 0.144 mmol) was suspended in dry DMF (2 ml). 2-Amino-1,2,4-thiadiazole (29 mg; 0.288 mmol) was added, followed by DMAP (35 mg; 0.288 mmol) and EDC (55 mg; 0.288 mmol). The mixture was stirred at ambient temperature for 24 hr. The reaction was diluted with iPrOAc (50 mL) and washed once with aq. sodium bicarbonate (10 mL), then twice more with water (2×10 mL). The organic was dried over magnesium sulfate, filtered and evaporated to a yellow solid. The solid was digested in refluxing MTBE. The mixture was cooled and the supernatant was drawn off. The remaining off-white solid was rinsed with cold MTBE, affording the title compound.

LRMS calc: 471.2. obs: 472.1 (M+H), 372.1 (M-BOC+H).

Examples reported in Table 12 can be prepared by one or more of the procedures described above (12.1-5) from readily available starting materials and tert-butyl 4,4'-bipiperidine-1-carboxylate by one skilled in the art (*=see below Table 1 for additional synthetic information). The LRMS of all BOC containing compounds gave an M+1 and an M-100+1 (M-BOC+1) ion.

TABLE 12

| Ex.* | Procedures | Chemical name | Chemical Structure | (M + 1) |
|---|---|---|---|---|
| 12.1 | 12.1 | tert-Butyl 1'-(4-cyanophenyl)-4,4'-bipiperidine-1-carboxylate | 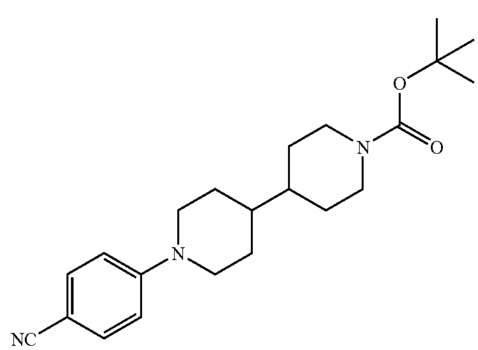 | 370.2<br>270.2<br>(M-BOC + 1) |

TABLE 12-continued

| Ex.* | Procedures | Chemical name | Chemical Structure | (M + 1) |
|---|---|---|---|---|
| 12.2* | 12.1 | tert-butyl 1'-[4-(aminocarbonyl)phenyl]-4,4'-bipiperidine-1-carboxylate | 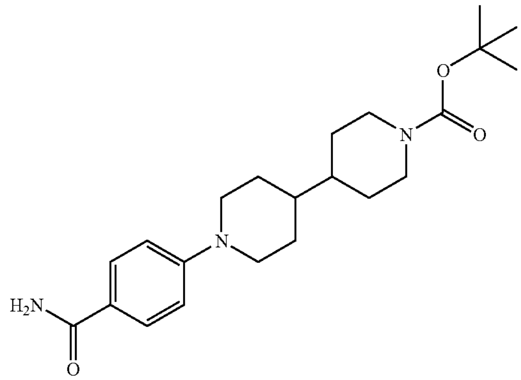 [SMILES: CC(C)(C)OC(=O)N1CCC(C2CCN(c3ccc(C(N)=O)cc3)CC2)CC1] | 388.2<br>288.3 |
| 12.3 | 12.2 | tert-Butyl 1'-[4-(methylthio)phenyl]-4,4'-bipiperidine-1-carboxylate | 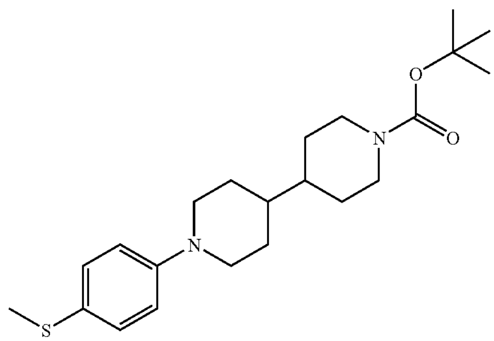 [SMILES: CSc1ccc(N2CCC(C3CCN(C(=O)OC(C)(C)C)CC3)CC2)cc1] | 391.2<br>291.3 |
| 12.4* | 12.2 | tert-butyl 1'-[4-(methylsulfinyl)phenyl]-4,4'-bipiperidine-1-carboxylate | 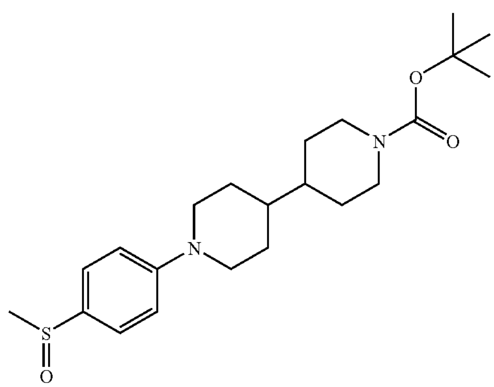 [SMILES: CS(=O)c1ccc(N2CCC(C3CCN(C(=O)OC(C)(C)C)CC3)CC2)cc1] | 407.2<br>307.1 |
| 12.5 | 12.2 | tert-butyl 1'-(4-bromophenyl)-4,4'-bipiperidine-1-carboxylate | 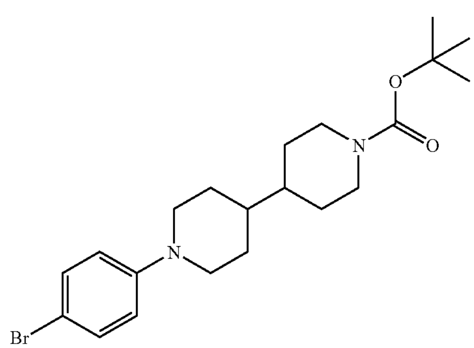 [SMILES: CC(C)(C)OC(=O)N1CCC(C2CCN(c3ccc(Br)cc3)CC2)CC1] | 423.2<br>323.2 |

TABLE 12-continued

| Ex.* | Procedures | Chemical name | Chemical Structure | (M + 1) |
|---|---|---|---|---|
| 12.6 | 12.2 | tert-butyl 1'-[4-(aminosulfonyl)phenyl]-4,4'-bipiperidine-1-carboxylate | 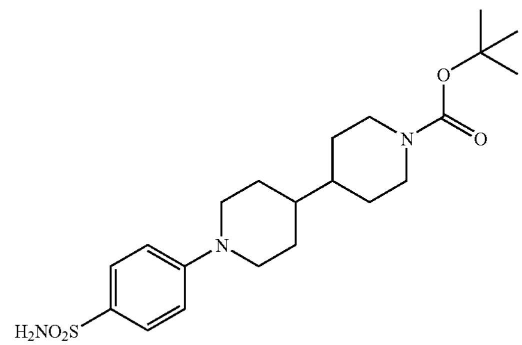 [SMILES: CC(C)(C)OC(=O)N1CCC(C2CCN(c3ccc(S(N)(=O)=O)cc3)CC2)CC1] | 423.2 323.2 |
| 12.7 | 12.2 | tert-butyl 1'-{4-[(methylamino)sulfonyl]phenyl}-4,4'-bipiperidine-1-carboxylate | 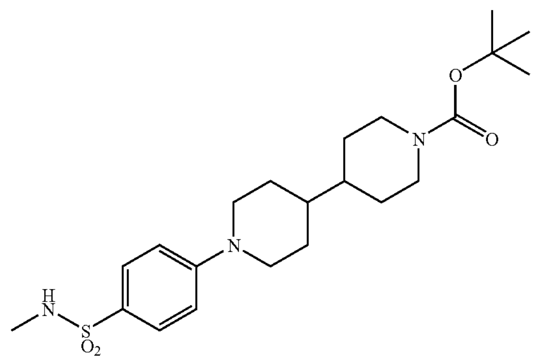 | 438.2 338.3 |
| 12.8 | 12.2 | tert-butyl 1'-{4-[(dimethylamino)sulfonyl]phenyl}-4,4'-bipiperidine-1-carboxylate | 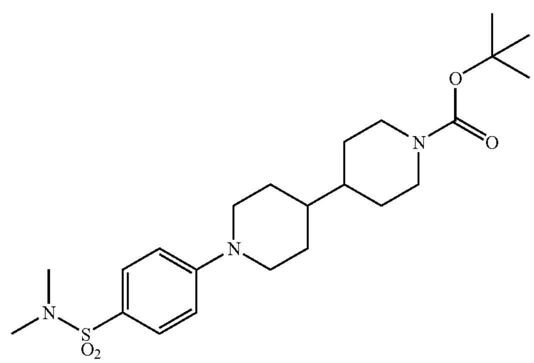 [SMILES: CN(C)S(=O)(=O)c1ccc(N2CCC(C3CCN(C(=O)OC(C)(C)C)CC3)CC2)cc1] | 452.2 352.3 |
| 12.9 | 12.2 | tert-butyl 1'-(3-cyanophenyl)-4,4'-bipiperidine-1-carboxylate | 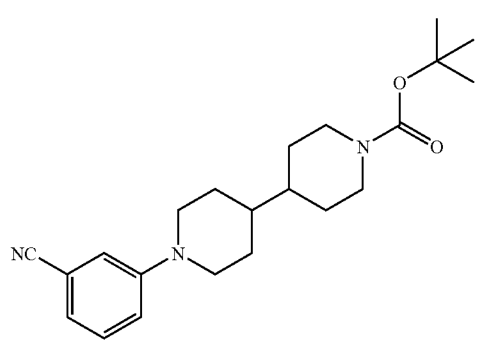 | 370.2 270.2 |

TABLE 12-continued

| Ex.* | Procedures | Chemical name | Chemical Structure | (M + 1) |
|---|---|---|---|---|
| 12.10 | 12.2 | tert-butyl 1'-{3-chloro-4-[(dimethylamino)carbonyl]phenyl}-4,4'-bipiperidine-1-carboxylate | 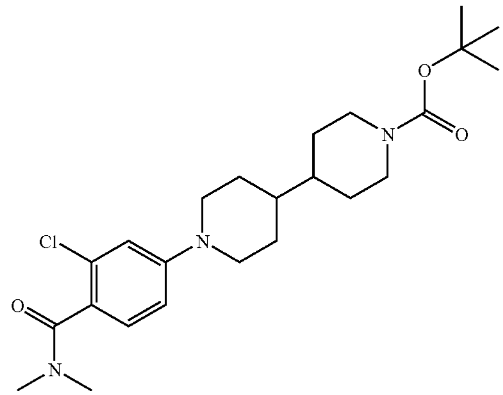 [SMILES: CN(C)C(=O)c1ccc(N2CCC(C3CCN(C(=O)OC(C)(C)C)CC3)CC2)cc1Cl] | 450.2<br>350.1 |
| 12.11 | 12.3, 4, 5 | tert-butyl 1'-{4-[(1,2,4-thiadiazol-5-ylamino)carbonyl]phenyl}-4,4'-bipiperidine-1-carboxylate | 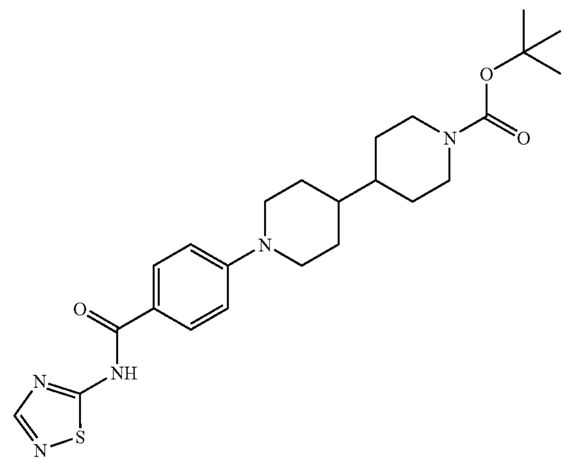 [SMILES: CC(C)(C)OC(=O)N1CCC(C2CCN(c3ccc(C(=O)Nc4ncns4)cc3)CC2)CC1] | 472.2<br>372.2 |
| 12.12 | 12.3, 4, 5 | tert-butyl 1'-{4-[(1,3-thiazol-2-ylamino)carbonyl]phenyl}-4,4'-bipiperidine-1-carboxylate | 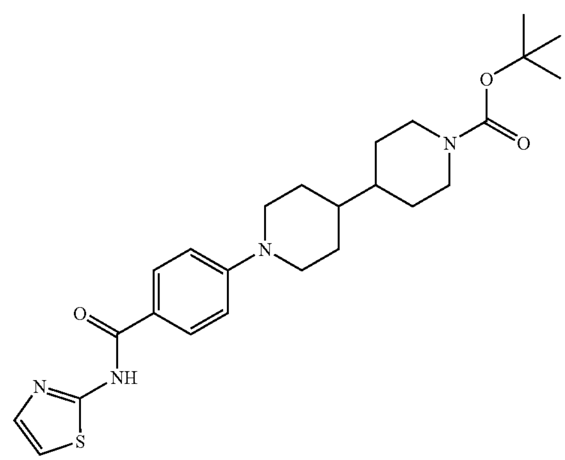 [SMILES: CC(C)(C)OC(=O)N1CCC(C2CCN(c3ccc(C(=O)Nc4nccs4)cc3)CC2)CC1] | 471.2<br>371.3 |

TABLE 12-continued

| Ex.* | Procedures | Chemical name | Chemical Structure | (M + 1) |
|---|---|---|---|---|
| 12.13 | 12.3, 4, 5 | tert-butyl 1'-{4-[(1H-imidazol-2-ylamino)carbonyl]phenyl}-4,4'-bipiperidine-1-carboxylate | 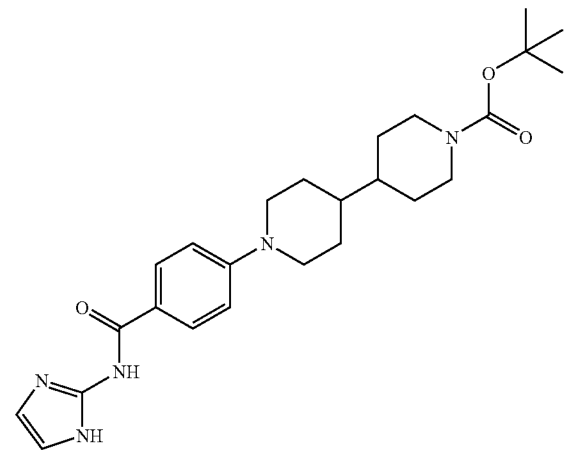 [SMILES: CC(C)(C)OC(=O)N1CCC(C2CCN(c3ccc(C(=O)Nc4ncc[nH]4)cc3)CC2)CC1] | 454.2 354.3 |
| 12.14 | 12.3, 4, 5 | tert-butyl 1'-{4-[(1H-1,2,4-triazol-3-ylamino)carbonyl]phenyl}-4,4'-bipiperidine-1-carboxylate | 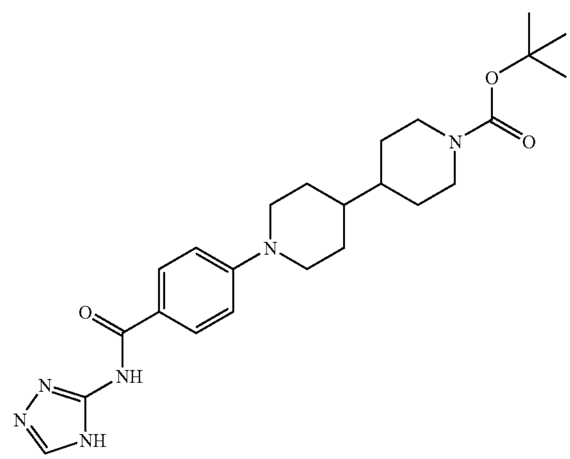 [SMILES: CC(C)(C)OC(=O)N1CCC(C2CCN(c3ccc(C(=O)Nc4nnc[nH]4)cc3)CC2)CC1] | 455.3 355.3 |
| 12.15 | 12.3, 4, 5 | tert-butyl 1'-{3-chloro-4-[(1,3-thiazol-2-ylamino)carbonyl]phenyl}-4,4'-bipiperidine-1-carboxylate | 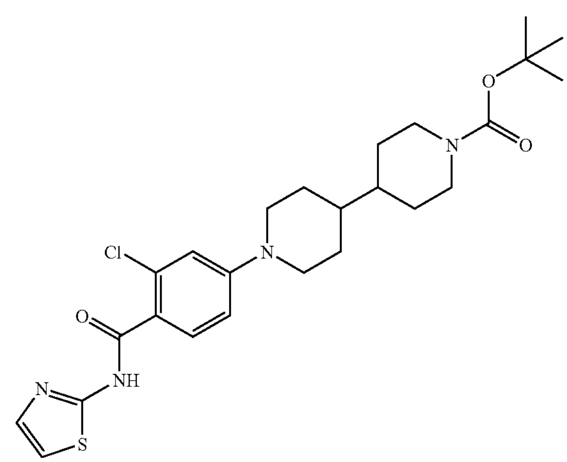 | 505.1 405.1 |

TABLE 12-continued

| Ex.* | Procedures | Chemical name | Chemical Structure | (M + 1) |
|---|---|---|---|---|
| 12.16 | 12.3, 4, 5 | tert-butyl 1'-{3-fluoro-4-[(1,3-thiazol-2-ylamino)carbonyl]phenyl}-4,4'-bipiperidine-1-carboxylate | 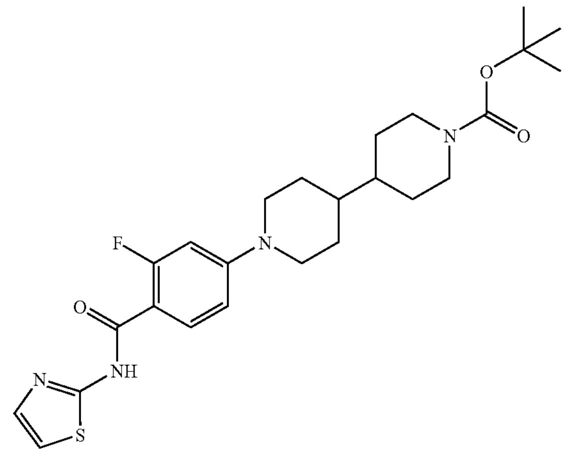 [SMILES: CC(C)(C)OC(=O)N1CCC(C2CCN(c3ccc(C(=O)Nc4nccs4)c(F)c3)CC2)CC1] | 489.2<br>389.3 |
| 12.17 | 12.3, 4, 5 | tert-butyl 1'-{3-fluoro-4-[(dimethylamino)carbonyl]phenyl}-4,4'-bipiperidine-1-carboxylate | 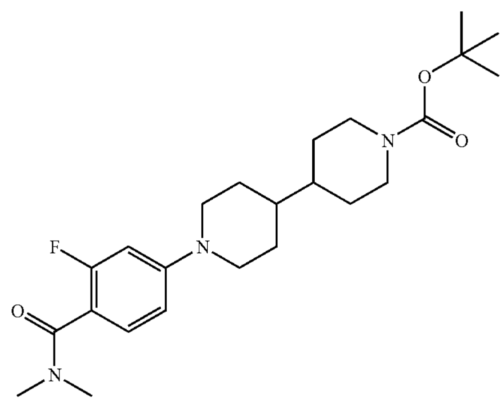 [SMILES: CN(C)C(=O)c1ccc(N2CCC(C3CCN(C(=O)OC(C)(C)C)CC3)CC2)cc1F] | 434.2<br>334.3 |
| 12.18 | 12.2 | tert-butyl 1'-{4-[(methylamino)carbonyl]phenyl}-4,4'-bipiperidine-1-carboxylate | 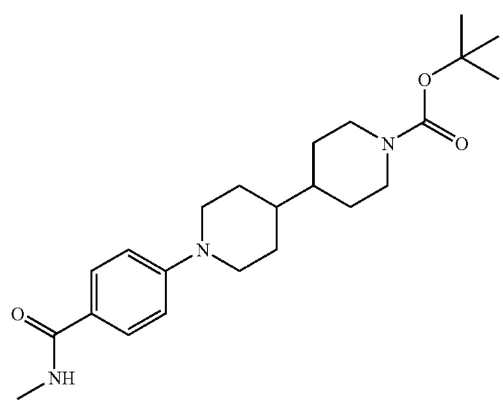 [SMILES: CNC(=O)c1ccc(N2CCC(C3CCN(C(=O)OC(C)(C)C)CC3)CC2)cc1] | 402.3<br>302.2 |

TABLE 12-continued

| Ex.* | Procedures | Chemical name | Chemical Structure | (M + 1) |
|---|---|---|---|---|
| 12.19 | 12.2 | tert-butyl 1'-{4-[(dimethylamino)carbonyl]phenyl}-4,4'-bipiperidine-1-carboxylate | 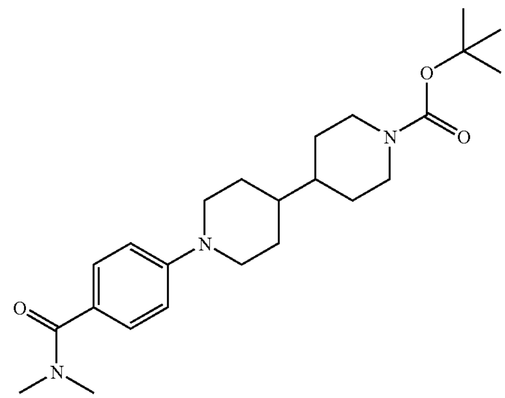 [SMILES: CN(C)C(=O)c1ccc(N2CCC(C3CCN(C(=O)OC(C)(C)C)CC3)CC2)cc1] | 416.3 316.3 |
| 12.20* | 12.3, 4 | tert-butyl 1'-[4-(2-amino-2-oxoethyl)phenyl]-4,4'-bipiperidine-1-carboxylate | 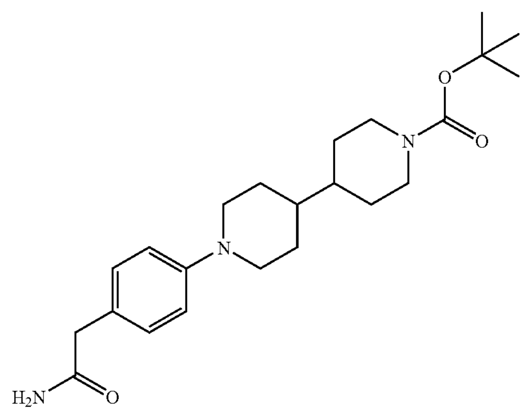 [SMILES: CC(C)(C)OC(=O)N1CCC(C2CCN(c3ccc(CC(N)=O)cc3)CC2)CC1] | 402.2 302.2 |
| 12.21 | 12.3, 4, 5 | tert-butyl 1'-(4-{[ethyl(methyl)amino]carbonyl}phenyl)-4,4'-bipiperidine-1-carboxylate | 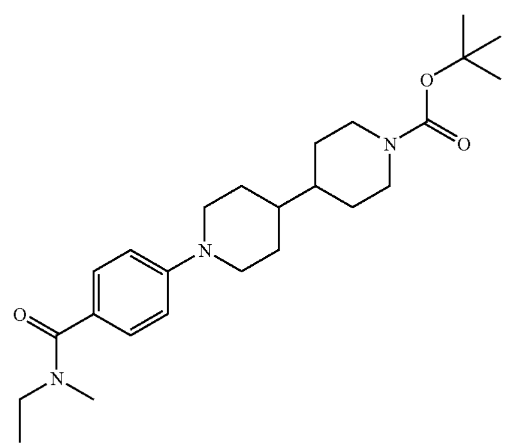 [SMILES: CCN(C)C(=O)c1ccc(N2CCC(C3CCN(C(=O)OC(C)(C)C)CC3)CC2)cc1] | 430.3 330.2 |

TABLE 12-continued

| Ex.* | Procedures | Chemical name | Chemical Structure | (M + 1) |
|---|---|---|---|---|
| 12.22* | 12.2 | tert-butyl 1'-[4-(hydroxymethyl)phenyl]-4,4'-bipiperidine-1-carboxylate | 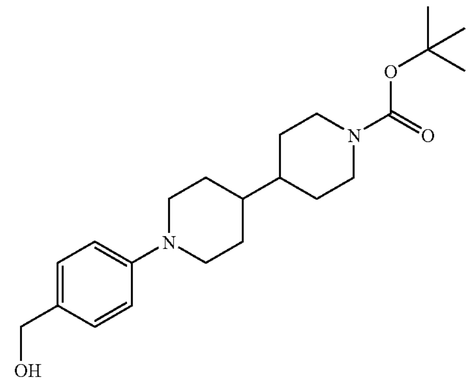 [SMILES: CC(C)(C)OC(=O)N1CCC(C2CCN(c3ccc(CO)cc3)CC2)CC1] | 375.2<br>275.3 |
| 12.23 | 12.3, 4, 5 | tert-butyl 1'-{3-[(1,3-thiazol-2-ylamino)carbonyl]phenyl}-4,4'-bipiperidine-1-carboxylate | 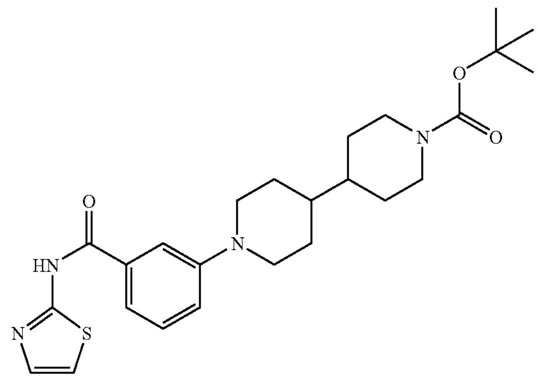 [SMILES: CC(C)(C)OC(=O)N1CCC(C2CCN(c3cccc(C(=O)Nc4nccs4)c3)CC2)CC1] | 471.2<br>371.2 |
| 12.24* | 12.3, 4 | tert-butyl 1'-[4-(1,3-thiazol-2-yl)phenyl]-4,4'-bipiperidine-1-carboxylate | 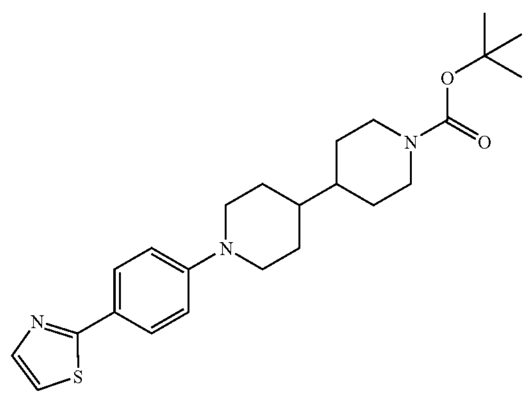 [SMILES: CC(C)(C)OC(=O)N1CCC(C2CCN(c3ccc(-c4nccs4)cc3)CC2)CC1] | 428.2<br>328.3 |
| 12.25* | 12.3, 4 | tert-butyl 1'-{4-[2-(1,3-thiazol-2-yl)ethyl]phenyl}-4,4'-bipiperidine-1-carboxylate | 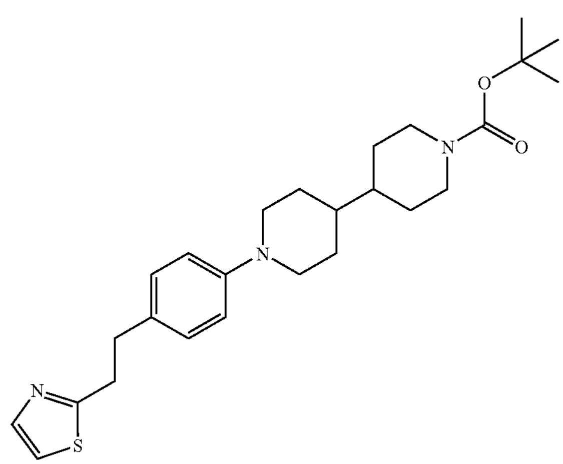 [SMILES: CC(C)(C)OC(=O)N1CCC(C2CCN(c3ccc(CCc4nccs4)cc3)CC2)CC1] | 456.2<br>356.2 |

TABLE 12-continued

| Ex.* | Procedures | Chemical name | Chemical Structure | (M + 1) |
|---|---|---|---|---|
| 12.26* | 12.2 | tert-butyl 1'-[4-(1,3-oxazol-2-yl)phenyl]-4,4'-bipiperidine-1-carboxylate | 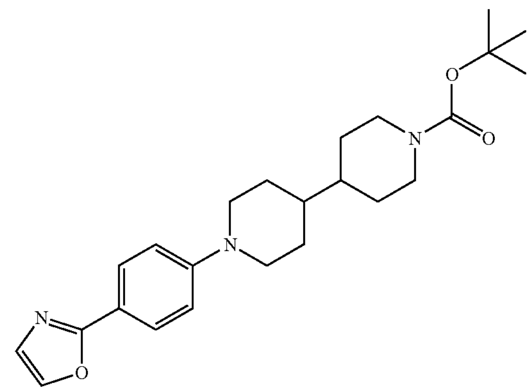 | 412.2 312.2 |
| 12.27* | 12.3, 4, 5 | tert-butyl 1'-[4-(4,5-dihydro-1,3-oxazol-2-yl)phenyl]-4,4'-bipiperidine-1-carboxylate | 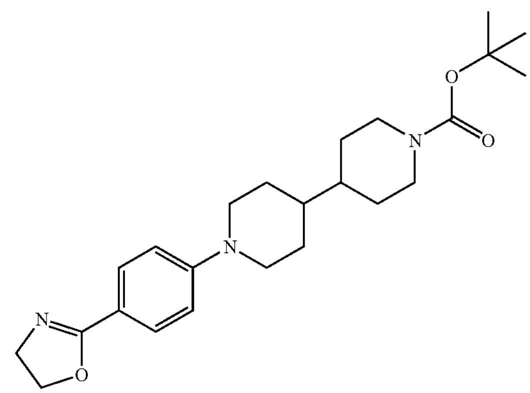 [SMILES: CC(C)(C)OC(=O)N1CCC(C2CCN(c3ccc(C4=NCCO4)cc3)CC2)CC1] | 414.3 314.2 |
| 12.28 | 12.3 | tert-butyl 1'-[6-(methylthio)-3-pyridinyl]-4,4'-bipiperidine-1-carboxylate | 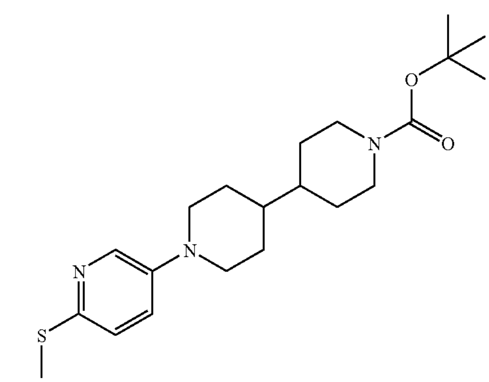 [SMILES: CSc1ccc(N2CCC(C3CCN(C(=O)OC(C)(C)C)CC3)CC2)cn1] | 392.1 292.2 |
| 12.29* | 12.3, 4, 5 | tert-butyl 1'-{4-[(1,3-thiazol-2-ylcarbonyl)amino]phenyl}-4,4'-bipiperidine-1-carboxylate | 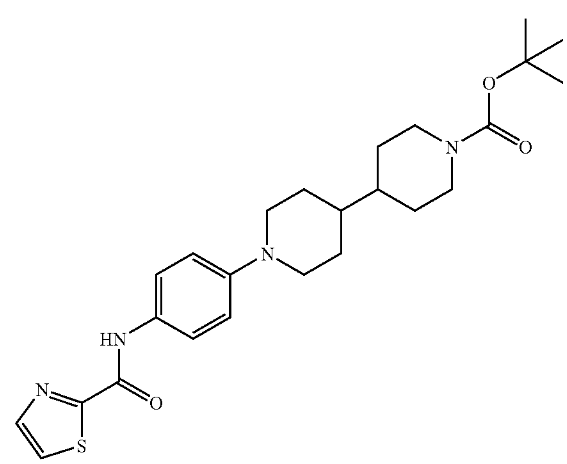 [SMILES: CC(C)(C)OC(=O)N1CCC(C2CCN(c3ccc(NC(=O)c4nccs4)cc3)CC2)CC1] | 471.2 371.1 |

TABLE 12-continued

| Ex.* | Procedures | Chemical name | Chemical Structure | (M + 1) |
|---|---|---|---|---|
| 12.30* | 12.1, 5 | tert-butyl 1'-{4-[(1,3-thiazol-4-ylcarbonyl)amino]phenyl}-4,4'-bipiperidine-1-carboxylate | 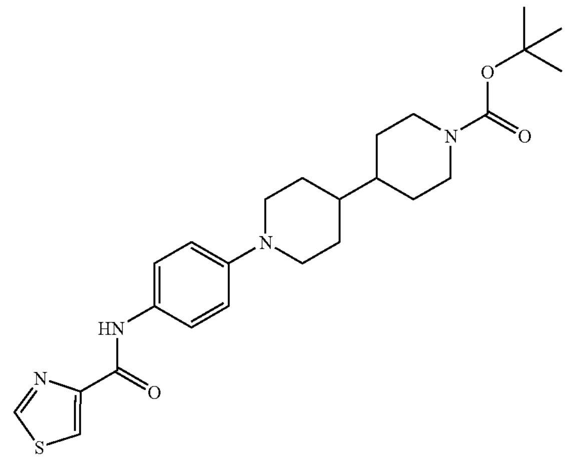 [SMILES: CC(C)(C)OC(=O)N1CCC(C2CCN(c3ccc(NC(=O)c4cscn4)cc3)CC2)CC1] | 471.1<br>371.1 |
| 12.31* | 12.1, 5 | tert-butyl 1'-{3-chloro-4-[(1,3-thiazol-4-ylcarbonyl)amino]phenyl}-4,4'-bipiperidine-1-carboxylate | 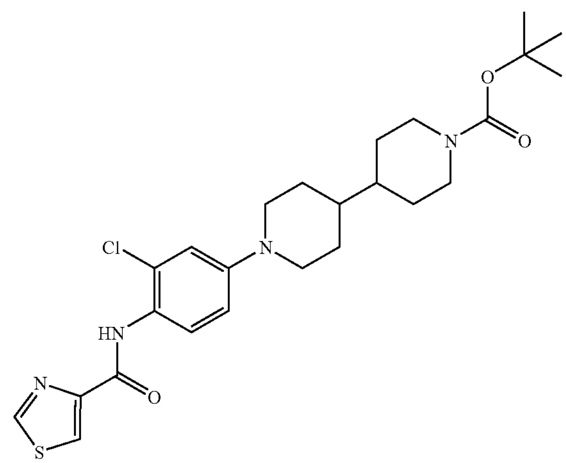 [SMILES: CC(C)(C)OC(=O)N1CCC(C2CCN(c3ccc(NC(=O)c4cscn4)c(Cl)c3)CC2)CC1] | 505.2<br>405.2 |

*Additional information

EXAMPLE 12.2

Preparation of tert-butyl 1'-[4-(aminocarbonyl)phenyl]-4,4'-bipiperidine-1-carboxylate

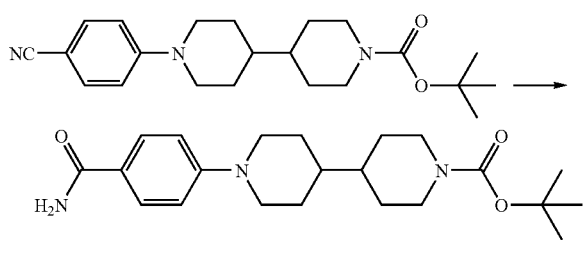

A solution of compound 12.1 (26 mg; 0.070 mmol) in EtOH (2 mL) was treated with an aqueous solution of NaO$_2$H (280 µL; 2M; 0.56 mmol). The mixture was refluxed for 18 hr. The reaction was partitioned between dichloromethane and water. The organic was dried over magnesium sulfate, filtered and evaporated to afford the title compound as a white solid. LRMS calc: 387.3. obs: 388.2 (M+H), 288.3 (M-BOC+H).

EXAMPLE 12.4

Preparation of tert-butyl-1'-[4-(methylsulfinyl)phenyl]-4,4'-bipiperidine-1-carboxylate

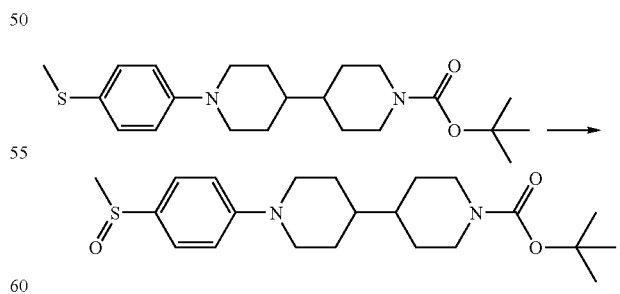

A solution of compound 12.3 (76 mg; 0.195 mmol) in dichloromethane (2 mL) was treated with mCPBA (45 mg; 75 wt %; 0.195 mmol). The mixture was stirred at ambient temperature for 30 min. The reaction was partitioned between iPrOAc (50 mL) and aq. sodium bicarbonate (10 mL). The organic was washed three more times with aq. sodium bicarbonate (3×10 mL). The organic was dried over magnesium sulfate, filtered and evaporated to a solid. The solid was digested in refluxing hexane. The mixture was cooled and filtered, affording the title compound as a white solid.

LRMS calc: 406.2. obs: 407.1 (M+H), 307.2 (M-BOC+H).

EXAMPLE 12.20

Preparation of tert-butyl-1'-[4-(2-amino-2-oxoethyl) phenyl]-4,4'-bipiperidine-1-carboxylate

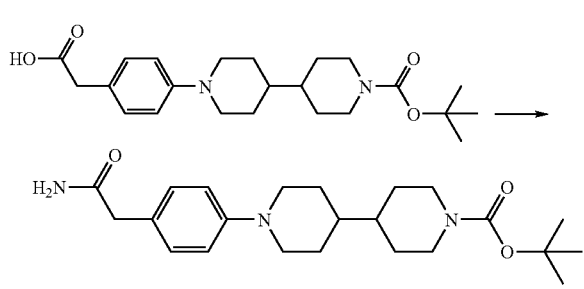

1-Hydroxybenzotriazole hydrate (53 mg; 0.388 mmol) was dissolved in a solution of ammonia in methanol (5 mL; 7M). The solution was evaporated to a white solid. A solution of {4-[1'-(tert-butoxycarbonyl)-4,4'-bipiperidin-1-yl] phenyl}acetic acid (52 mg; 0.129 mmol) in DMF (2 mL) was added, followed by EDC (75 mg; 0.388 mmol). The mixture was stirred at ambient temperature for 1 hr. The reaction was partitioned between iPrOAc (50 mL) and aq. sodium bicarbonate (10 mL). The organic was washed twice more with water (2×10 mL). The organic was dried over magnesium sulfate, filtered and evaporated to a solid. The solid was chromatographed (PTLC; 40:1 CH$_2$Cl$_2$/MeOH), affording the title compound.

LRMS calc: 401.3. obs: 402.3 (M+H), 302.2 (M-BOC+H).

EXAMPLE 12.22

Preparation of tert-Butyl 1'-[4-(hydroxymethyl)phenyl]-4,4'-bipiperidine-1-carboxylate

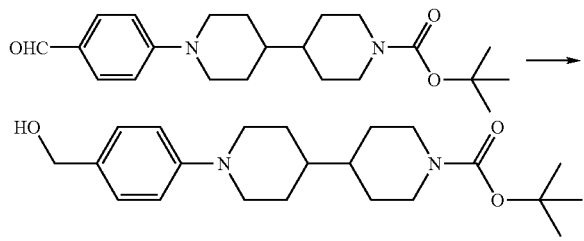

A solution of tert-Butyl 1'-(4-formylphenyl)-4,4'-bipiperidine-1-carboxylate (72 mg; 0.193 mmol) in EtOH (1 mL) was treated with NaBH$_4$ (8 mg; 0.213 mmol). The solution was stirred at ambient temperature for 1 hr. The reaction was partitioned between iPrOAc and water. The organic was dried over magnesium sulfate, filtered and evaporated to afford the title compound.

LRMS calc: 374.3. obs: 375.3 (M+H), 275.2 (M-BOC+H).

EXAMPLE 12.24

Preparation of tert-Butyl-1'-[4-(1,3-thiazol-2-yl)phenyl]-4,4'-bipiperidine-1-carboxylate Step 1: tert-Butyl-1'-[4-(aminocarbonothioyl)phenyl]-4,4'-bipiperidine-1-carboxylate

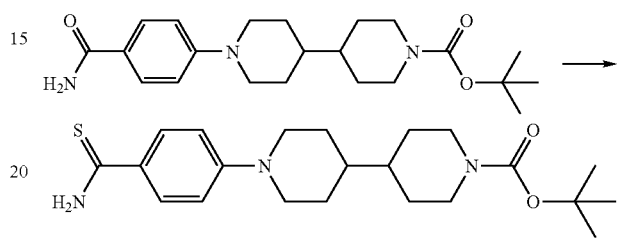

A suspension of compound 12.2 (227 mg; 0.586 mmol) in dioxane (8 ml) was treated with Lawesson's Reagent (355 mg; 0.879 mmol). The mixture was stirred at ambient temperature for 56 hr. The mixture was filtered and evaporated to a yellow solid. The solid was adsorbed onto silica gel and eluted exhaustively without fractionation (40:1 CH2Cl2/MeOH). The eluant was evaporated to a yellow solid. The solid was chromatographed (Horizon; 0% to 7% MeOH/CH2Cl2; linear gradient). The yellow fractions were collected and evaporated to give the title compound.

LRMS calc: 403.2. obs: 404.2 (M+H), 304.1 (M-BOC+H).

Step 2 tert-Butyl-1'-[4-(1,3-thiazol-2-yl)phenyl]-4,4'-bipiperidine-1-carboxylate

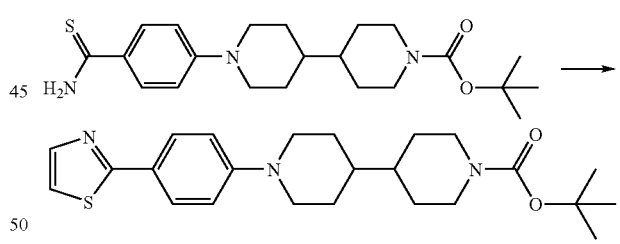

A solution of the product of Example 12.24, Step 1 above (151 mg; 0.374 mmol) in DMF (3 ml) was treated with Ac$_2$O (1 ml) and chloroacetaldehyde (587 mg; 50% aq. solution; 3.74 mmol). The solution was stirred at 80° C. for 1 hr. The reaction was partitioned between iPrOAc (50 mL) and aq. sodium bicarbonate (20 mL). The organic was washed three more times with aq. sodium bicarbonate (3×10 mL). The organic was dried over magnesium sulfate, filtered and evaporated to a brown semi-solid. The solid was digested (refluxing MTBE). The nearly homogenous solution was allowed to stand at −10° C. for 1 hr, causing the deposition of a tan solid. The supernatant was drawn off and the solid rinsed with MTBE. All volatiles were removed and light tan solid was chromatographed (PTLC; 40:1 CH$_2$Cl$_2$/MeOH), affording the title compound.

LRMS calc: 427.2. obs: 428.1 (M+H), 328.1 (M-BOC+H).

EXAMPLE 12.25 tert-butyl-1'-{4-[2-(1,3-thiazol-2-yl)ethyl]phenyl}-4,4'-bipiperidine-1-carboxylate Step 1: tert-butyl-1'-[4-(3-amino-3-oxopropyl)phenyl]-4,4'-bipiperidine-1-carboxylate

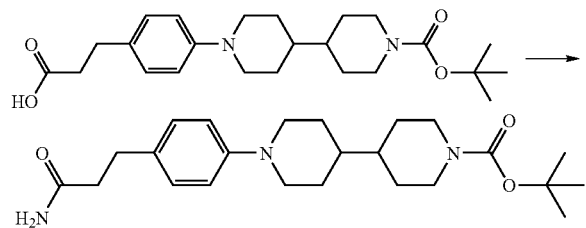

This compound was prepared using the method of Example 12.20 above.
LRMS: calc. 415.3. obs. 416.2 (M+H), 316.3 (M-BOC+H).

Step 2: tert-butyl-1'-[4-(3-amino-3-thioxopropyl)phenyl]-4,4'-bipiperidine-1-carboxylate

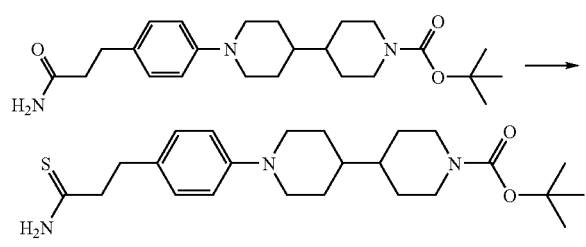

This compound was prepared using the method of Example 12.24, Step 1.
LRMS: calc. 431.3. obs. 432.3 (M+H), 332.3 (M-BOC+H).

Step 3: tert-butyl-1'-{4-[2-(1,3-thiazol-2-yl)ethyl]phenyl}-4,4'-bipiperidine-1-carboxylate

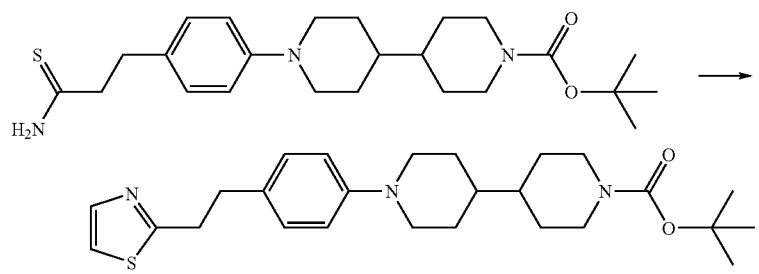

This compound was prepared using the method of Example 12.24, Step 2. LRMS: calc. 455.3. obs. 456.2 (M+H), 356.2 (M-BOC+H).

EXAMPLE 12.26

Preparation of tert-butyl-1'-[4-(1,3-oxazol-2-yl)phenyl]-4,4'-bipiperidine-1-carboxylate Step 1: tert-butyl 1'-(4-iodophenyl)-4,4'-bipiperidine-1-carboxylate

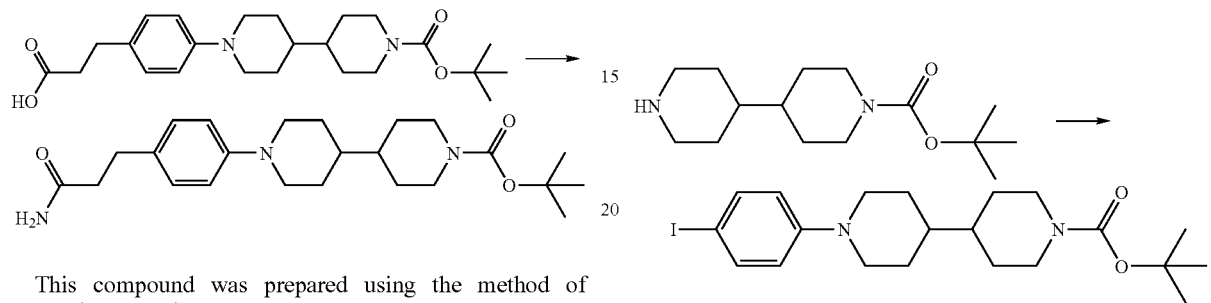

This compound was prepared using the method of General Procedure 12.2. LRMS: calc. 470.1. obs. 471.2 (M+H), 371.3 (M-BOC+H).

Step 2: tert-butyl-1'-[4-(1,3-oxazol-2-yl)phenyl]-4,4'-bipiperidine-1-carboxylate

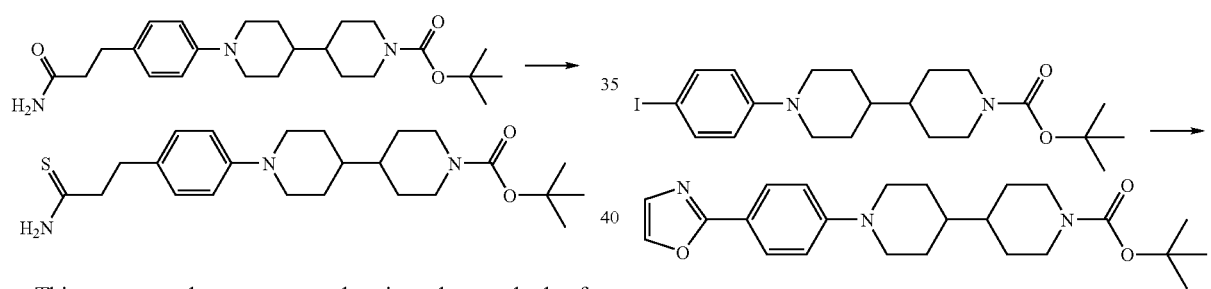

A −10° C. solution of MgBr$_2$ (37 mg; 0.202 mmol) in THF (1 mL) was treated with nBuLi (0.333 mL; 1.82M; 0.606 mmol) The solution was stirred at −10° C. for 1 hr. A solution of oxazole (42 mg; 0.606 mmol) in THF (0.5 mL) was added and the solution was stirred at 25° C. for 2 hr. This solution was added to a refluxing solution of tert-butyl 1'-(4-iodophenyl)-4,4'-bipiperidine-1-carboxylate (285 mg; 0.606 mmol) and PdCl$_2$(dppf) (495 mg; 0.606 mmol) in THF (4 mL). The mixture was refluxed 1 hr. The reaction was partitioned between CH$_2$Cl$_2$ and water. The organic was dried over magnesium sulfate, filtered and evaporated to a solid. The solid was chromatographed (PTLC; 40:1 CH$_2$Cl$_2$/MeOH) to afford the title compound.

LRMS: calc. 411.3. obs. 412.2 (M+H), 312.3 (M+H-BOC).

EXAMPLE 12.27

Preparation of tert-butyl-1'-[4-(4,5-dihydro-1,3-oxazol-2-yl)phenyl]-4,4'-bipiperidine-1-carboxylate Step 1: tert-butyl 1'-(4-{[(2-hydroxyethyl)amino]carbonyl}phenyl)-4,4'-bipiperidine-1-carboxylate

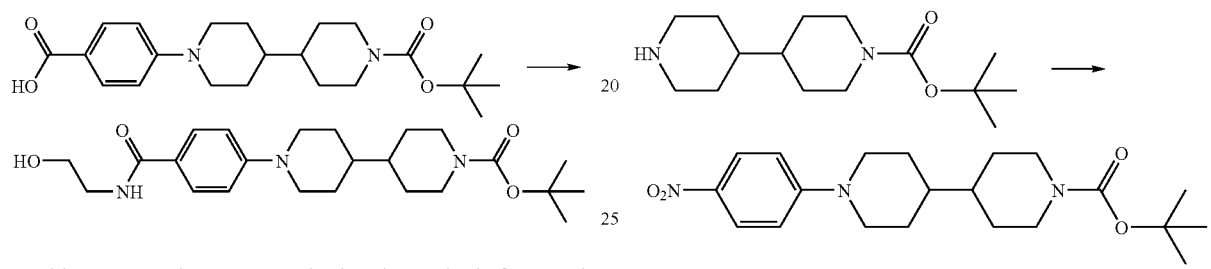

This compound was prepared using the method of General Procedure 12.5 and ethanolamine as starting material.

LRMS: calc. 431.3. obs. 432.2 (M+H), 332.2 (M-BOC+H).

Step 2: tert-butyl-1'-[4-(4,5-dihydro-1,3-oxazol-2-yl)phenyl]-4,4'-bipiperidine-1-carboxylate

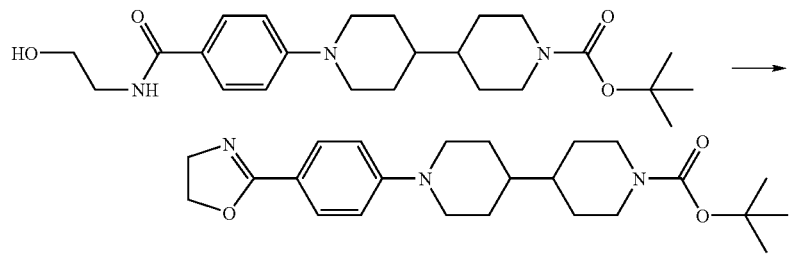

A solution of tert-butyl 1'-(4-{[(2-hydroxyethyl)amino]carbonyl}phenyl)-4,4'-bipiperidine-1-carboxylate (234 mg; 0.542 mmol) in dioxane (5 mL) was treated with N,N'-diisopropylcarbodiimide (68 mg; 0.084 mmol) and Cu(OTf)$_2$ (10 mg; 0.027 mmol). The mixture was refluxed for 5 hr. The reaction was evaporated and chromatographed (PTLC; 40:1 CH$_2$Cl$_2$/MeOH), giving the title compound.

LRMS: calc. 413.3. obs. 414.3 (M+H), 314.2 (M-BOC+H).

EXAMPLE 12.29

Preparation of tert-Butyl-1'-{4-[(1,3-thiazol-2-ylcarbonyl)amino]phenyl}-4,4'-bipiperidine-1-carboxylate Step 1: tert-Butyl 1'-(4-nitrophenyl)-4,4'-bipiperidine-1-carboxylate

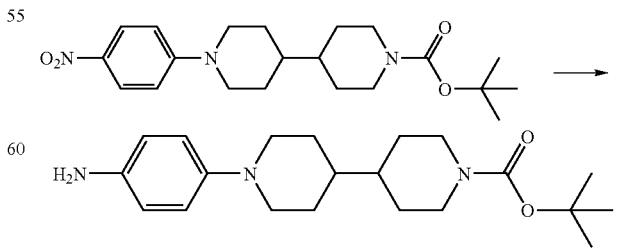

Using General Procedure 12.1 with 4-fluoro-nitrobenzene as starting material the title compound was obtained.

LRMS calc: 389.2. obs: 390.2 (M+H), 290.1 (M-BOC+H).

Step 2: tert-Butyl 1'-(4-aminophenyl)-4,4'-bipiperidine-1-carboxylate

A suspension of the product of Example 12.29, Step 1 above (640 mg; 1.643 mmol) in an EtOH/EtOAc mixture (15 mL; 1:2 vol. ratio) was hydrogenated (35 psi) in the presence 10% Pd/C catalyst (150 mg) for 1 hr. The mixture was filtered through Celite and evaporated to afford the title compound as a gray solid.

LRMS calc: 359.3 obs: 360.2. (M+H), 260.3 (M-BOC+H).

Step 3: Thiazole-2-carboxylic acid

A solution of ethyl thiazole-2-carboxylate (1.46 g; 9.29 mmol), obtained using a literature method (Helv. Chim Acta 1945, 28, p. 924), in EtOH (10 ml) was placed in a sealable vessel and treated with KOH (3.07 g; 46.4 mmol). The vessel was sealed and heated at 120° C. for 30 min. After cooling, the solution was poured into water (50 mL) and the pH adjusted to 4.0 with con. HCl. The now turbid mixture was extracted with iPrOAc (50 mL), dried over magnesium sulfate, filtered and evaporated to a brown oil. The oil was dissolved in $CH_2Cl_2$ and filtered, then evaporated to afford the title compound as a brown pasty solid.

Step 4: tert-Butyl-1'-{4-[(1,3-thiazol-2-ylcarbonyl)amino]phenyl}-4,4'-bipiperidine-1-carboxylate

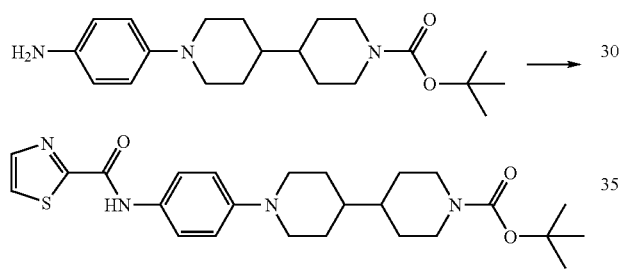

A solution of the product of Example 12.29, Step 2 above (50 mg; 0.139 mmol) and Example 12.29, Step 3 (36 mg; 0.278 mmol) in DMF (1 ml) was treated with PyBOP (145 mg; 0.278 mmol). The reaction was stirred at ambient temperature for 4 hr. The reaction was partitioned between iPrOAc (50 mL) and pH7 phosphate buffer (10 mL). The organic was washed twice more with pH7 buffer (2×10 mL). The wet organic was evaporated and repartitioned between $CH_2Cl_2$ and water. The organic was dried over magnesium sulfate, filtered and evaporated. The derived residue was digested in refluxing MTBE. The red-brown supernatant was found to be enriched in the title compound. The solution was evaporated to an oil and chromatographed (PTLC; 20:1 $CH_2Cl_2$/MeOH). The title compound was a rust colored solid. The material was rechromatographed (PTLC; MTBE). The baseline band was recovered giving the title compound as a light rust colored powdery solid.

LRMS calc: 470.2. obs: 471.2 (M+H), 371.3 (M-BOC+H).

EXAMPLE 12.30

Preparation of tert-Butyl-1'-{4-[(1,3-thiazol-4-ylcarbonyl)amino]phenyl}-4,4'-bipiperidine-1-carboxylate

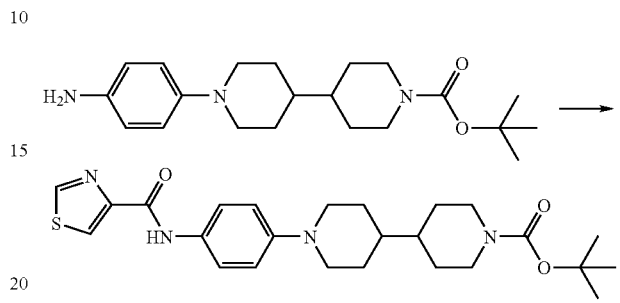

This compound was prepared according to the method of Example 12.29, Step 4.

EXAMPLE 12.31

Preparation of tert-butyl-1'-{3-chloro-4-[(1,3-thiazol-4-ylcarbonyl)amino]phenyl}-4,4'-bipiperidine-1-carboxylate Step 1: tert-Butyl 1'-(3-chloro-4-nitrophenyl)-4,4'-bipiperidine-1-carboxylate

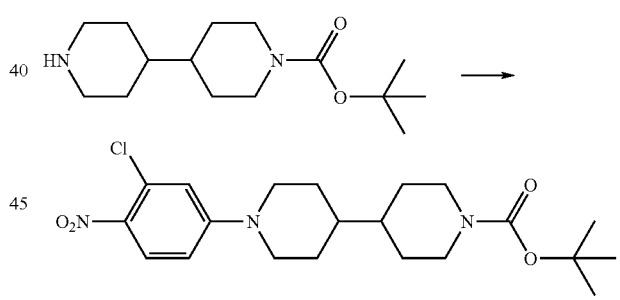

Using the method of Example 12.29, Step 1 with 2-chloro-4-fluoro-nitrobenzene as starting material the title compound was obtained.

LRMS calc: 423.2. obs: 424.1 (M+H), 324.1 (M-BOC+H).

Step 2: tert-Butyl 1'-(3-chloro-4-aminophenyl)-4,4'-bipiperidine-1-carboxylate

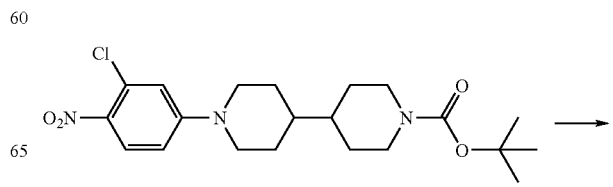

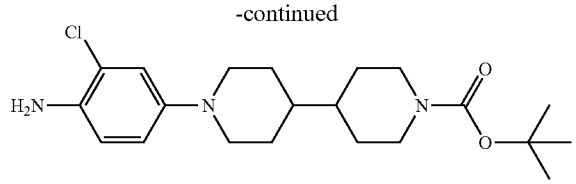

Using the method of Example 12.29, Step 2 the title compound was obtained.

LRMS calc: 393.2. obs: 394.1 (M+H), 294.2 (M-BOC+H).

Step 3: tert-Butyl-1'-{3-chloro-4-[(1,3-thiazol-4-ylcarbonyl)amino]phenyl}-4,4'-bipiperidine-1-carboxylate

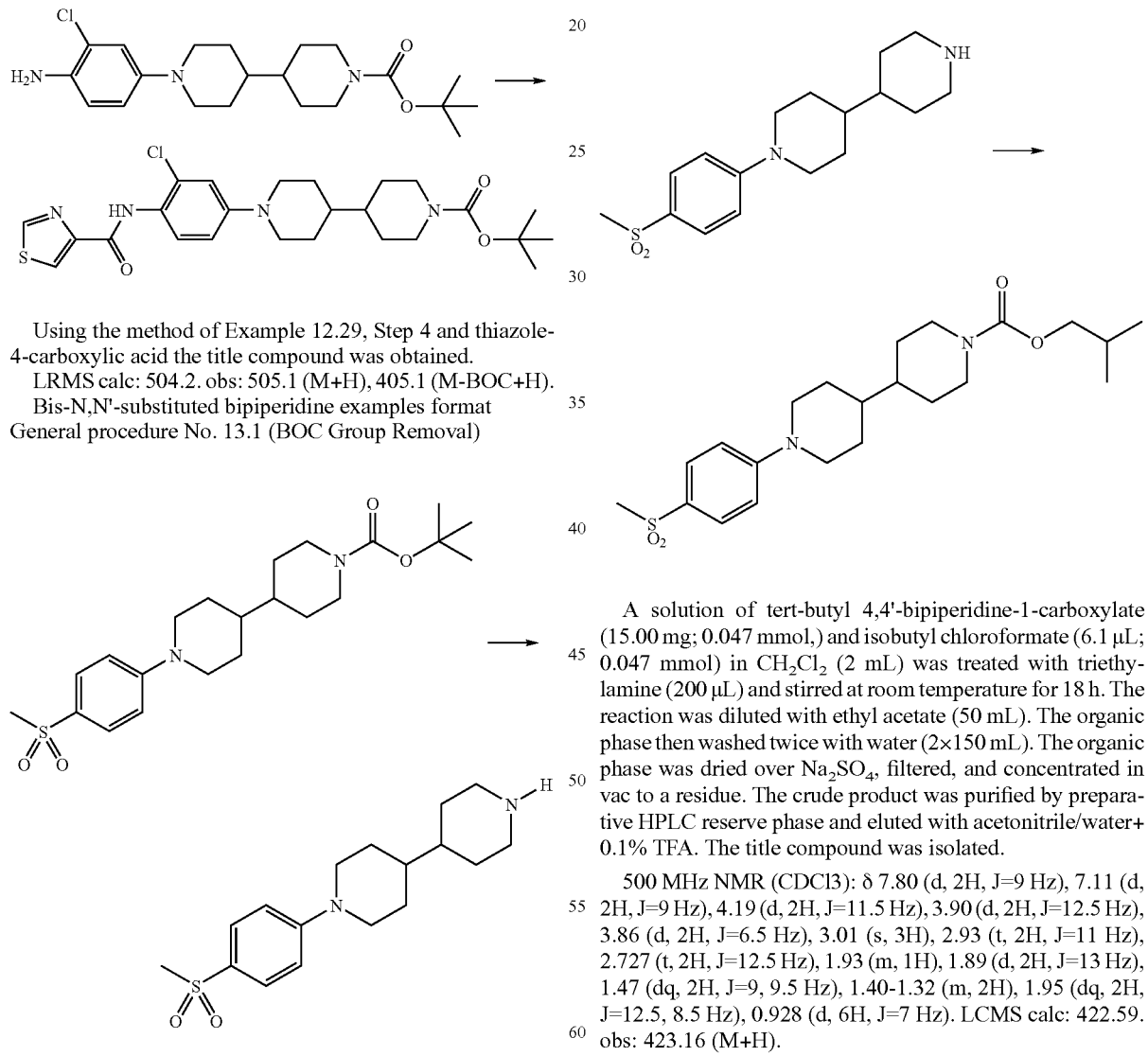

Using the method of Example 12.29, Step 4 and thiazole-4-carboxylic acid the title compound was obtained.

LRMS calc: 504.2. obs: 505.1 (M+H), 405.1 (M-BOC+H).

Bis-N,N'-substituted bipiperidine examples format
General procedure No. 13.1 (BOC Group Removal)

A solution of tert-butyl 1'-[4-(methylsulfonyl)phenyl]-4,4'-bipiperidine-1-carboxylate (4.95 g, 11.71 mmol) in CH$_2$Cl$_2$ (20 mL) was treated with trifluoroacetic acid (4 mL) and stirred at room temperature for 3 hr. The reaction was diluted with CH$_2$Cl$_2$ (50 mL) and washed with 1 N HCl (50 mL). The aqueous layers were combined and washed with 5N NaOH (100 ml). The mixture was extracted with CHCl$_3$, dried over Na$_2$SO$_4$, filtered and concentrated in vac to afford title compound.

500 MHz NMR (CD3OD): δ 7.69 (d, 2H, J=9 Hz), 7.02 (d, 2H, J=9.5 Hz), 3.99 (d, 2H, J=13 Hz), 3.02 (m, 5H), 2.83 (t, 2H, J=12 Hz), 2.52 (t, 2H, J=12 Hz), 1.83 (d, 2H, J=10 Hz), 1.72 (d, 2H, J=11 Hz), 1.24 (m, 6H). LCMS calc: 322.47. obs: 323.17 (M+H).

General Procedure 13.2 (Carbamates)

EXAMPLE 13.1 isobutyl 1'-[4-(methylsulfonyl)phenyl]-4,4'-bipiperidine-1-carboxylate

A solution of tert-butyl 4,4'-bipiperidine-1-carboxylate (15.00 mg; 0.047 mmol,) and isobutyl chloroformate (6.1 μL; 0.047 mmol) in CH$_2$Cl$_2$ (2 mL) was treated with triethylamine (200 μL) and stirred at room temperature for 18 h. The reaction was diluted with ethyl acetate (50 mL). The organic phase then washed twice with water (2×150 mL). The organic phase was dried over Na$_2$SO$_4$, filtered, and concentrated in vac to a residue. The crude product was purified by preparative HPLC reserve phase and eluted with acetonitrile/water+ 0.1% TFA. The title compound was isolated.

500 MHz NMR (CDCl3): δ 7.80 (d, 2H, J=9 Hz), 7.11 (d, 2H, J=9 Hz), 4.19 (d, 2H, J=11.5 Hz), 3.90 (d, 2H, J=12.5 Hz), 3.86 (d, 2H, J=6.5 Hz), 3.01 (s, 3H), 2.93 (t, 2H, J=11 Hz), 2.727 (t, 2H, J=12.5 Hz), 1.93 (m, 1H), 1.89 (d, 2H, J=13 Hz), 1.47 (dq, 2H, J=9, 9.5 Hz), 1.40-1.32 (m, 2H), 1.95 (dq, 2H, J=12.5, 8.5 Hz), 0.928 (d, 6H, J=7 Hz). LCMS calc: 422.59. obs: 423.16 (M+H).

General Procedure 13.3 (Acylation)

EXAMPLE 12.4

4-methyl-1-{1'-[4-(methylsulfonyl)phenyl]-4,4'-bipiperidin-1-yl}-1-oxopentan-2-one

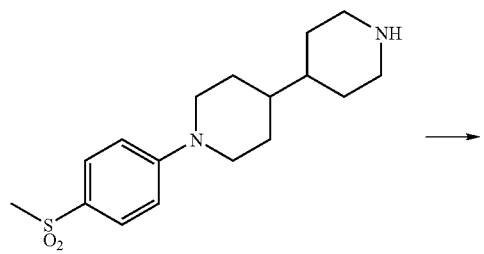

→

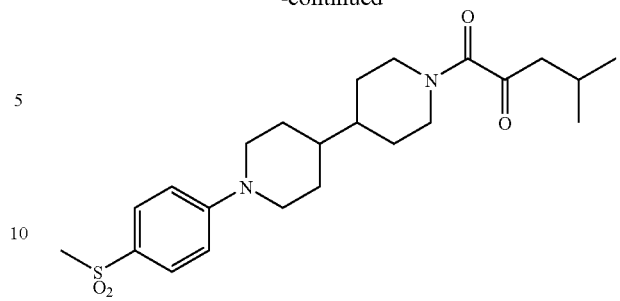

A solution of 4-methyl-2-oxovaleric acid (8.07 mg; 0.062 mmol) was treated sequentially with 1-hydroxybenzotriazole hydrate (11.4 mg; 0.0741 mmol), EDC (14.3 mg; 0.074 mmol) and 1 1-[4-(methylsulfonyl)phenyl]-4,4'-bipiperidine (20.0.0 mg; 0.062 mmol) and stirred at ambient temperature for 18 h. The reaction was diluted with $CH_2Cl_2$(10 mL) and washed with water (15 mL). The organic phase was then dried over $Na_2SO_4$, filtered and concentrated in. vac to a residue. The crude product was purified by preparative HPLC reserve phase and eluted with acetonitrile/water+0.1% TFA. The title compound was isolated.

500 MHz NMR (CDCl3) δ: 7.73 (d, 2H, J=9 Hz), 6.91 (d, 2H, J=9 Hz), 4.55 (dt, 1H, J=2 Hz), 3.92 (d, 2H, J=12.5 Hz), 3.77 (dt, 2H, J=2 Hz), 3.01 (s, 3H), 2.83 (t, 2H, J=12 Hz), 2.68-2.58 (m, 2H), 2.20 (m, 1H), 1.86-1.76 (m, 4H), 1.44-1.18 6H), 0.980 (d, 6H, J=6.5 Hz). LCMS calc: 434.60. obs: 435.17 (M+H).

Examples reported in Table 13 can be prepared by the procedures described above from readily available starting materials and tert-butyl 4,4'-bipiperidine-1-carboxylate.

TABLE 13

| Example | Procedure | Chemical name | Chemical Structure | (M + 1) |
|---------|-----------|---------------|--------------------|---------|
| 13.5 | 13.2 | isopropyl 1'-[4-(methylsulfonyl)phenyl]-4,4'-bipiperidine-1-carboxylate | 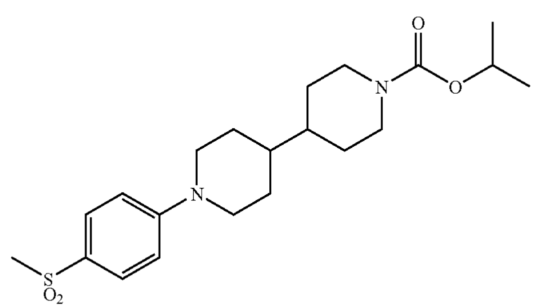 | 409.29 |
| 13.6 | 13.2 | isobutyl 1'-[2-fluoro-4-(methylsulfonyl)phenyl]-4,4'-bipiperidine-1-carboxylate | 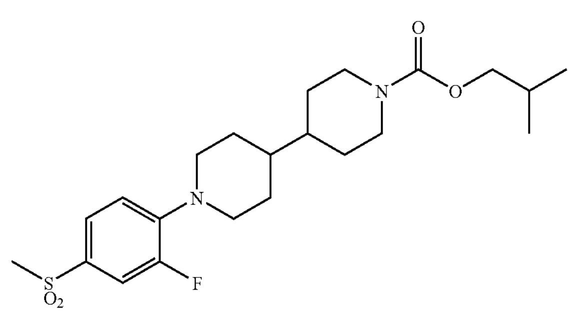 [SMILES: CC(C)COC(=O)N1CCC(C2CCN(c3ccc(S(C)(=O)=O)cc3F)CC2)CC1] | 441.15 |

TABLE 13-continued

| Example | Procedure | Chemical name | Chemical Structure | (M + 1) |
|---|---|---|---|---|
| 13.7 | 13.2 | propyl 1'-[4-(methylsulfonyl)phenyl]-4,4'-bipiperidine-1-carboxylate | 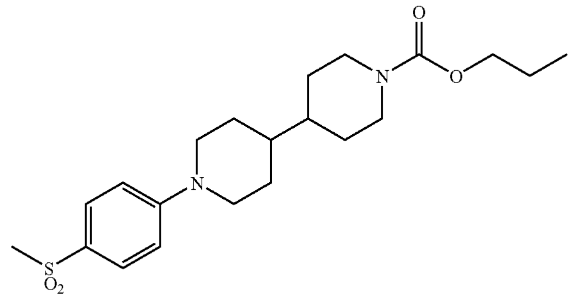 [SMILES: CCCOC(=O)N1CCC(C2CCN(c3ccc(S(C)(=O)=O)cc3)CC2)CC1] | 409.12 |
| 13.8 | 13.2 | phenyl 1'-[4-(methylsulfonyl)phenyl]-4,4'-bipiperidine-1-carboxylate | 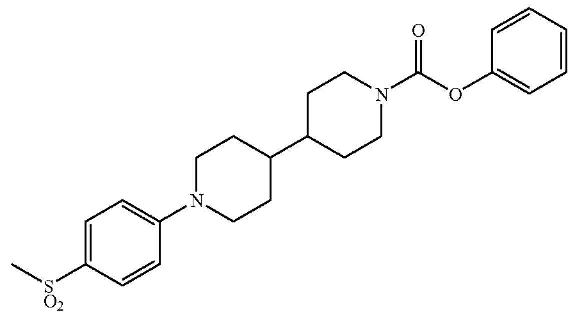 [SMILES: CS(=O)(=O)c1ccc(N2CCC(C3CCN(C(=O)Oc4ccccc4)CC3)CC2)cc1] | 443.11 |
| 13.9 | 13.2 | methyl 1'-[4-(methylsulfonyl)phenyl]-4,4'-bipiperidine-1-carboxylate | 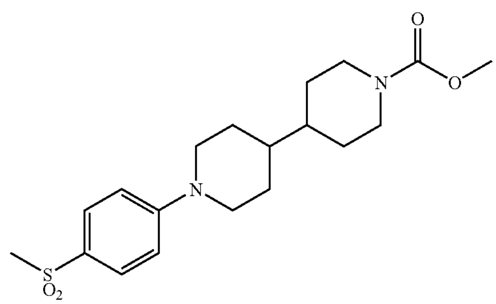 | 381.17 |
| 13.10 | 13.22 | ethyl 1'-[4-(methylsulfonyl)phenyl]-4,4'-bipiperidine-1-carboxylate | 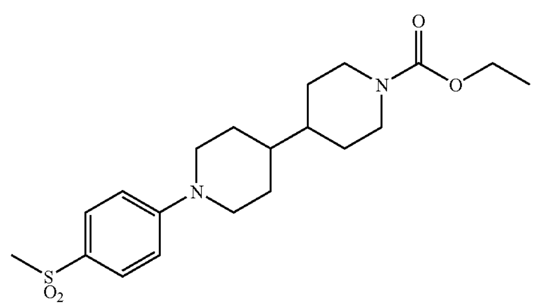 [SMILES: CCOC(=O)N1CCC(C2CCN(c3ccc(S(C)(=O)=O)cc3)CC2)CC1] | 395.20 |
| 13.11 | 13.2 | 4-methoxyphenyl 1'-[4-(methylsulfonyl)phenyl]-4,4'-bipiperidine-1-carboxylate | | 473.29 |
| 13.11 | 13.2 | 2,2-dimethylpropyl 1'-[4-(methylsulfonyl)phenyl]-4,4'-bipiperidine-1- | | 437.32 |

General Procedure 14.1:

Preparation of 1-(5-fluoro-2-methylpyrimidin-4-yl)-1'-(5-fluoropyrimidin-2-yl)-4,4'-bipiperidine Step 1: tert-butyl 1'-(2-chloro-5-fluoropyrimidin-4-yl)-4,4'-bipiperidine-1-carboxylate: same as Procedure 2.1, substituting the dichlorofluoropyrimidine shown below for dichloropyrazine

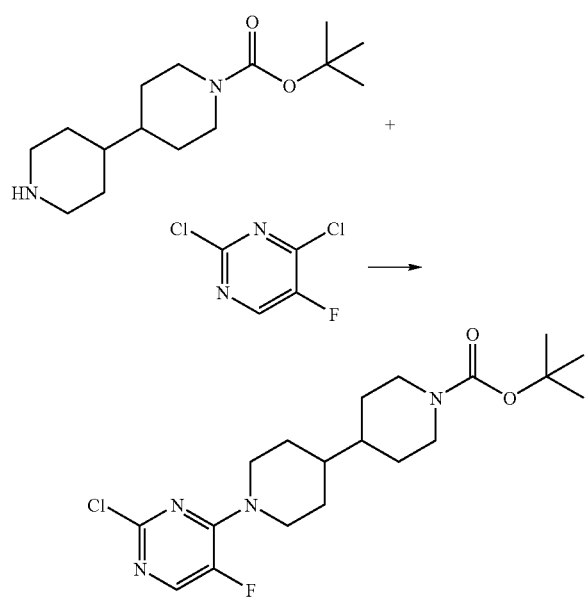

Step 2: tert-butyl 1'-(5-fluoro-2-methylpyrimidin-4-yl)-4,4'-bipiperidine-1-carboxylate: same as Procedure 4.1, step 2

General Procedure 15.1:

Preparation of 1-(5-fluoro-2-methylpyrimidin-4-yl)-1'-pyrimidin-2-yl-4,4'-bipiperidine Step 1: tert-butyl 1'-(2-chloro-5-fluoropyrimidin-4-yl)-4,4'-bipiperidine-1-carboxylate: same as Procedure 14.1 above

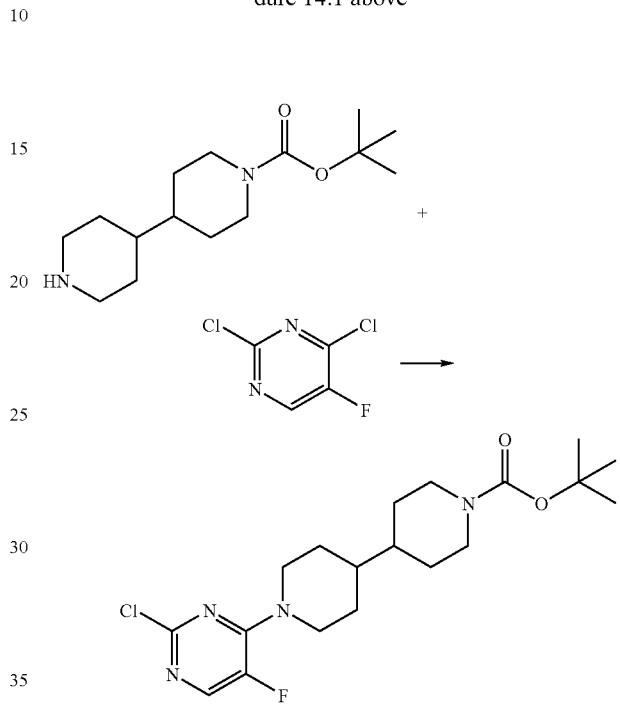

Step 2: tert-butyl 1'-(5-fluoro-2-methylpyrimidin-4-yl)-4,4'-bipiperidine-1-carboxylate: same as Procedure 4.1, step 2

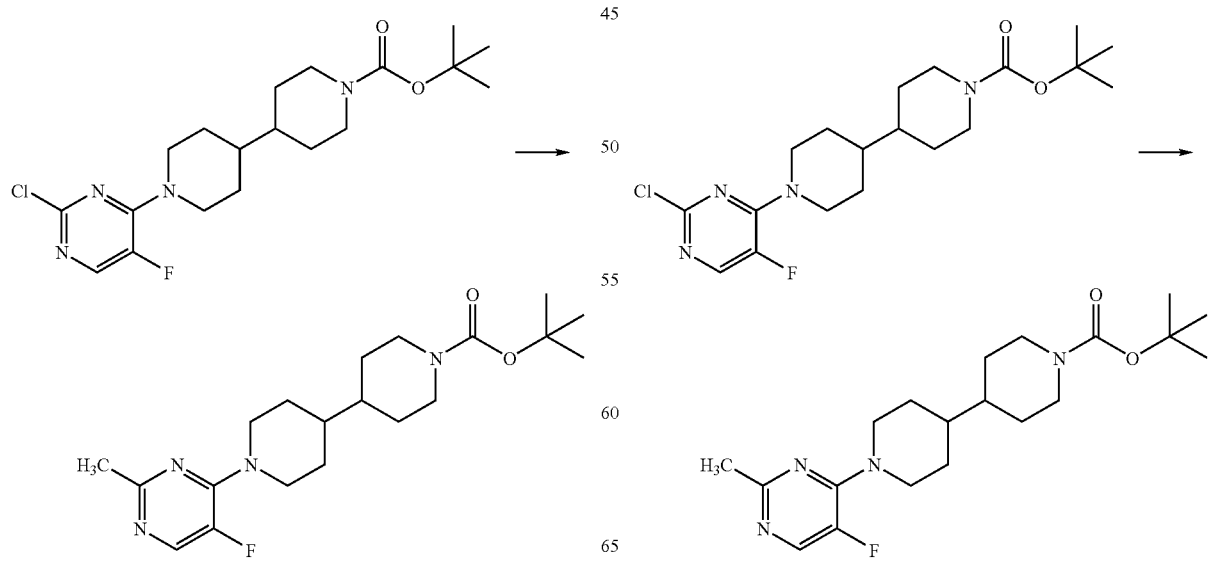

General Procedure 16.1:

Preparation of 6-[1'-(5-chloropyrimidin-2-yl)-4,4'-bipiperidin-1-yl]pyrimidine-4-carbonitrile Step 1: tert-butyl 1'-(6-chloropyrimidin-4-yl)-4,4'-bipiperidine-1-carboxylate: same as Procedure 2.1, substituting the dichloropyrimidine shown below for dichloropyrazine

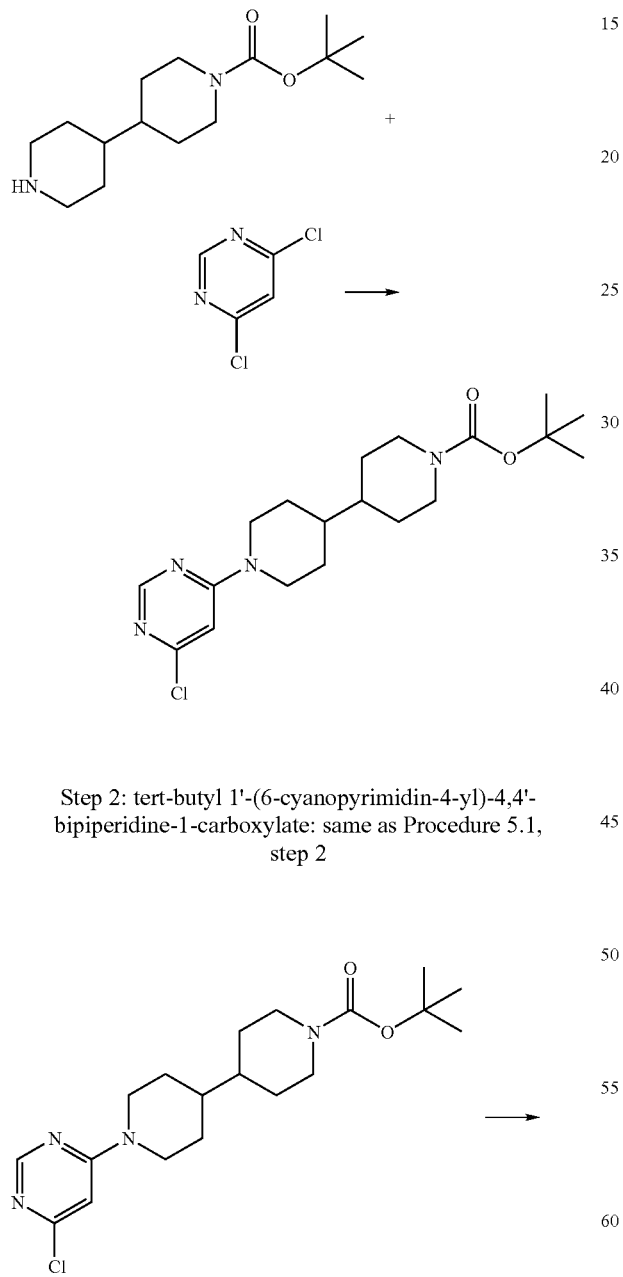

Step 2: tert-butyl 1'-(6-cyanopyrimidin-4-yl)-4,4'-bipiperidine-1-carboxylate: same as Procedure 5.1, step 2

General Procedure 17.1:

Preparation of 6-(1'-pyrimidin-2-yl-4,4'-bipiperidin-1-yl)pyrimidine-4-carbonitrile Step 1: tert-butyl 1'-(6-chloropyrimidin-4-yl)-4,4'-bipiperidine-1-carboxylate: same as Procedure 2.1

Step 2: tert-butyl 1'-(6-cyanopyrimidin-4-yl)-4,4'-bipiperidine-1-carboxylate: same as Procedure 5.1, step 2

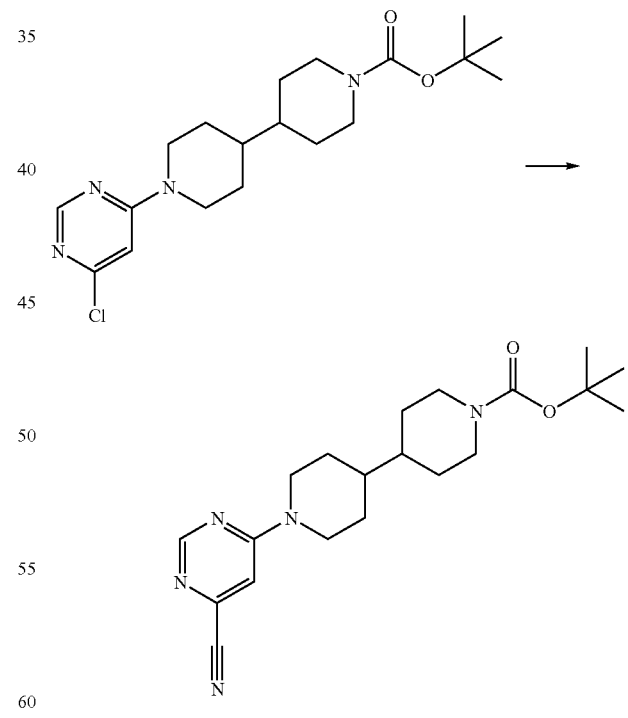

General Procedure 19.1 (Nucleophilic Aromatic Substitution)

Preparation of tert-butyl-1'-(3-chloro-1,2,4-thiadiazol-5-yl)-4,4'-bipiperidine-1-carboxylate

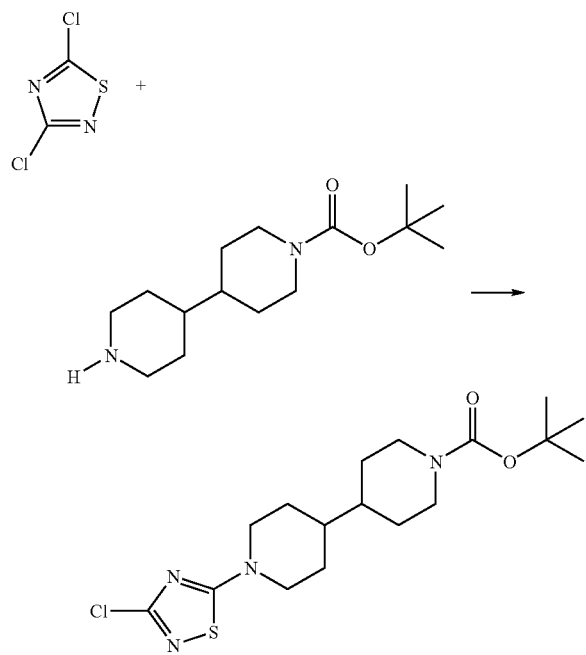

A solution of tert-butyl 4,4'-bipiperidine-1-carboxylate (537 mg; 2.00 mmol) in dry THF (10 mL) was treated with triethylamine (307 μL; 2.20 mmol). A solution of 3,5-dichloro-1,2,4-thiadiazole (341 mg; 2.20 mmol) in THF (5 mL) was added dropwise at ambient temperature. An immediate precipitate was accompanied by a mild exotherm. The mixture was stirred until it returned to ambient temperature. The mixture was filtered and the filtrate evaporated to afford the title compound.

LRMS calc: 386.2. obs: 387.2 (M+H), 287.1 (M-BOC+H).

General Procedure 19.2 (Dimethylamination)

EXAMPLE 19.2

Preparation of tert-butyl-1'-[3-(dimethylamino)-1,2,4-thiadiazol-5-yl]-4,4'-bipiperidine-1-carboxylate

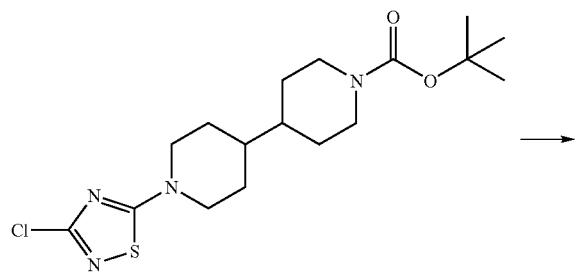

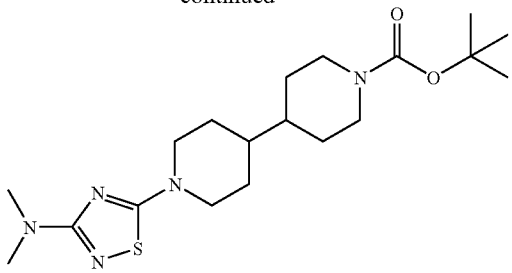

in a sealable vessel, a −10° C. solution of compound 19.1 (755 mg; 1.95 mmol) in DMF (10 mL) was permeated with anhydrous dimethylamine until the initial volume had increased to approximately 15 mL. The vessel was sealed and the solution heated in a 100° C. bath for 4 hr. After cooling the solution was outgassed with nitrogen at ambient temperature for 30 min. The reaction was partitioned between iPrOAc (75 mL) and water (20 mL). The organic was washed three more times with water (3×20 mL), dried over magnesium sulfate, filtered and evaporated to a solid. The solid was digested in refluxing MTBE, cooled and allowed to stand at ambient temperature for 72 hr. The supernatant was drawn off and the solid rinsed with MTBE to give the title compound.

LRMS calc: 395.2. obs: 396.2 (M+H), 296.2 (M-BOC+H).

Measurement of GPR119 Signaling Using a Cyclic AMP (cAMP) Homogenous Time Resolved Fluorescence (HTRF) Assay Chinese hamster ovary (CHO) cell lines stably transfected with the permissive guanine nucleotide binding protein alpha 15 (Gα15) and a human SNP variant of GPR119 or murine GPR119 were maintained in DMEM media containing FBS, penicillin-streptomycin, puromycin, and G418. A homogenous time resolved fluorescence (HTRF) assay for GPR119 receptor activation was used to measure cAMP accumulation in transfected cells upon incubation with compounds of this invention as per the manufacturer's instructions (CisBio, Bedford, Mass.). Cells were incubated with compound at room temperature for 60 min, and subsequently with XL-665 and anti-cAMP cryptate for an additional 60 min. The assay was conducted in 96 half-well plate format and the plate was read using a Perkin Elmer Envision plate reader. For compounds of this invention, "activation" of the GPR119 receptor in a cAMP HTRF assay denotes induction of about a five fold increase in intracellular cAMP concentration.

Evaluation of Glucose Dependent Insulin Secretion (GDIS) in Static Isolated Mouse Islets.

Pancreatic islets of Langerhans were isolated from the pancreata of 10-12 wk-old C57BL/6 mice by collagenase digestion and discontinuous Ficoll gradient separation, a modification of the original method of Lacy and Kostianovsky (Lacy & Kostianovsky, 1967 Diabetes 16-35-39). The islets were cultured overnight in RPMI 1640 medium (11 mM glucose, 10% FCS) before experimental treatment. The acute effects of compounds of this invention on GDIS were determined by 60-min static incubation with islets in Krebs-Ringers' bicarbonate (KRB) medium. The KRB medium contained, in mM, 143.5 $Na^+$, 5.8 $K^+$, 2.5 $Ca^{2+}$, 1.2 $Mg^{2+}$, 124.1 $Cl^-$, 1.2 $PO_4^{3-}$, 1.2 $SO_4^{2+}$, 25 $CO_3^{2-}$, and 10 HEPES, pH 7.4, in addition to 2 mg/ml bovine serum albumin, and either 2 (G2) or 16 (G16) mM glucose (pH 7.4). The static incubation was performed with round-bottomed 96-well plates (one islet/well with 200 μl KRB medium). The compounds were added to KRB medium just before the initiation of the 60-min incubation. Insulin concentration in aliquots of the incubation buffer was measured by the ultra-sensitive rat insulin EIA kit from ALPCO Diagnostics (Windham, N.H.).

Example of a Pharmaceutical Formulation

As a specific embodiment of an oral composition of a compound of the present invention, 50 mg of any of the examples is formulated with sufficient finely divided lactose to provide a total amount of 580 to 590 mg to fill a size O hard gelatin capsule.

While the invention has been described and illustrated in reference to specific embodiments thereof, various changes, modifications, and substitutions can be made therein without departing from the invention. For example, alternative effective dosages may be applicable, based upon the responsiveness of the patient being treated. Likewise, the pharmacologic response may vary depending upon the particular active compound selected, formulation and mode of administration. All such variations are included within the present invention.

What is claimed is:
1. A compound represented by formula I

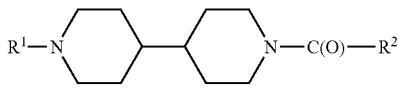

or a pharmaceutically acceptable salt thereof wherein
$R^1$ represents a 6-10 membered aryl group or a 5-10 membered heteroaryl group containing one or two rings, at least one nitrogen atom 0-2 additional nitrogen atoms, and 0-1 oxygen or sulfur atoms,
said 6-10 membered aryl or 5-10 membered heteroaryl group being optionally substituted with 1-3 halo groups,
wherein said 6-10 membered aryl or 5-10 membered heteroaryl group is substituted with 1-2 members selected from the group consisting of:
(1) $C_{1-6}$alkyl or $C_{3-6}$cycloalkyl, substituted with 1-2 members selected from the group consisting of:
  i) $S(O)_xC_{1-3}$alkyl, wherein x is 0, 1 or 2 and the alkyl portion is optionally substituted with 1-3 halo atoms; and
  ii) $C(O)NR^dR^e$ or $NR^dC(O)R^e$, wherein $R^d$ is selected from H and $C_{1-3}$alkyl and $R^e$ is selected from H, $C_{1-6}$alkyl, $C_{3-6}$cycloalkyl, a 5-6 membered Heteroaryl group and phenyl;
(2) $S(O)_xC_{1-6}$alkyl, and $SO_2NR^dR^e$ wherein the $C_{1-6}$alkyl group is optionally substituted with 1-3 halo groups, wherein x is 0, 1 or 2 and wherein $R^d$ and $R^e$ are as defined above; and
(3) $C(O)NR^dR^e$ or $NR^d(O)R^e$ wherein $R^d$ and $R^e$ are as defined above;
and
$R^2$ is selected from the group consisting of $C_{1-8}$alkyl, $C_{3-6}$cycloalkyl, $OC_{1-8}$alkyl and O-Phenyl, the phenyl portion of which being optionally substituted with 1-3 halo groups and 0-1 $C_{1-3}$alkyl, haloalkyl, alkoxy or haloalkoxy groups, and each of said $C_{1-8}$alkyl, $C_{3-6}$cycloalkyl and $OC_{1-8}$alkyl being optionally substituted with 1-3 halo proups, and 0-1 members selected from the group consisting of OH, oxo CN, $OC_{1-6}$alkyl, $haloC_{1-6}$alkoxy, pyridyl, $C(O)C_{1-3}$ alkyl phenyl, and $C(O)$phenyl,
said phenyl, pyridyl and the phenyl portion of $C(O)$phenyl being optionally substituted with 1-3 halo atoms, and 1-2 $C_{1-6}$ alkyl or $OC_{1-6}$alkyl groups.

2. A compound in accordance with claim 1 or a pharmaceutically acceptable salt thereof, wherein $R^1$ represents an optionally substituted 6-10 membered aryl group.

3. A compound in accordance with claim 1 or a pharmaceutically acceptable salt thereof, wherein $R^1$ represents optionally substituted phenyl.

4. A compound in accordance with claim 1 or a pharmaceutically acceptable salt thereof, wherein $R^1$ represents an optionally substituted 5-10 membered heteroaryl group.

5. A compound in accordance with claim 1 or a pharmaceutically acceptable salt thereof, wherein $R^1$ represents an optionally substituted 5-10 membered heteroaryl group, selected from the group consisting of thiazolyl, thadiazolyl pyridyl, pyrimidinyl, pyrazinyl and quinoxalinyl.

6. A compound in accordance with claim 1 or a pharmaceutically acceptable salt thereof, wherein $R^1$ represents a member selected from the group consisting of optionally substituted phenyl pyridyl, pyrimidinyl and pyrazinyl.

7. A compound in accordance with claim 1 or a pharmaceutically acceptable salt thereof, wherein $R^1$ represents optionally substituted phenyl or pyrimidinyl.

8. A compound in accordance with claim 1 or a pharmaceutically acceptable salt thereof, wherein $R^1$ represents a 6-10 membered aryl or 5-10 membered heteroaryl, optionally substituted with 1-2 halo atoms selected from fluoro, chloro and bromo,
wherein said 6-10 membered 5-10 membered heteroaryl is substituted with 1-2 members selected from the group consisting of:
(1) $C_{1-3}$alkyl or $C_{3-6}$ cycloalkyl, substituted with 1 member selected from the group consisting of:
  i) $S(O))_xC_{1-3}$ alkyl, wherein x is 0 or 2 and the alkyl portion is optionally substituted with 1-3 fluorine atoms; and
  ii) $C(O)NR^dR^e$ or $NR^dC(O)R^e$, wherein $R^d$ is selected from H and methyl, and $R^e$ is selected from H, methyl, $C_{3-6}$cycloalkyl, phenyl and a 5-6 membered heteroaryl group selected from thiazole, imidazole and triazole;
(2) $S(O)_xC_{1-3}$alkyl, and $SO_2NR^dR^e$ wherein x is 0, 1 or 2, $R^d$ and $R^e$ are as defined above, and the $C_{1-3}$alkyl portion is optionally substituted 1-3 halo groups selected from Cl and F; and
(3) $C(O)NR^dR^e$ or $NR^dC(O)R^e$ wherein $R^d$ and $R^e$ are as defined above.

9. A compound in accordance with claim 1 or a pharmaceutically acceptable salt thereof, wherein $R^1$ is phenyl or a 5-9 membered heteroaryl group, optionally substituted with 1-2 halo atoms selected from fluoro and chloro,
wherein said phenyl or 5-9 membered heteroaryl group is substituted with 1-2 members selected from the group consisting of:
(1) $CH_3$ or cyclopronyl, substituted with 1 member selected from the group consisting of:
  i) $S(O)_2C_{1-3}$alkyl, wherein the alkyl portion is optionally substituted with 1-3 fluorine atoms; and
  ii) $C(O)NR^dR^e$ or $NR^dC(O)R^e$, wherein $R^d$ is selected from H and methyl, and $R^e$ is selected from H, methyl, $C_{3-6}$cycloalkyl, phenyl and a 5-6 membered heteroaryl group selected from thiazole, imidazole and triazole;

(2) S(O)$_x$C$_{1-3}$alkyl, and SO$_2$NR$^d$R$^e$ wherein x is 0, 1 or 2 R$^d$ and R$^e$ are as defined above, and the C$_{1-3}$alkyl portion is optionally substituted with 1-3 halo groups selected from Cl and F; and (3) C(O)NR$^d$R$^e$ or NR$^d$C(O)R$^e$, wherein R$^e$ and R$^e$ are as defined above.

10. A compound in accordance with claim 1 or a pharmaceutically acceptable salt thereof, wherein:

R$^2$ is selected from the group consisting of C$_{1-7}$alkyl, C$_{3-6}$cycloalkyl, OC$_{1-6}$alkyl and O-phenyl, the phenyl portion of which being optionally substituted with 1-3 halo groups selected from chloro and fluoro, and 0-1 C$_{1-3}$alkyl, haloC$_{1-3}$alkyl, C$_{1-3}$alkoxy or haloC$_{1-3}$alkoxy groups, wherein the halo atoms are fluorine or chlorine, and each of said C$_{1-7}$alkyl, C$_{3-6}$cycloalkyl and OC$_{1-6}$alkyl being optionally substituted with 1-3 fluoro or chloro groups, and 0-1 members selected from the group consisting of OH, oxo, CN, OC$_{1-3}$alkyl, haloC$_{1-3}$alkoxy, C(O)C$_{1-3}$alkyl, phenyl, and C(O)phenyl, said phenyl and the phenyl portion of C(O)phenyl being optionally substituted with 1-3 chlorine or fluorine atoms, and 1-2 C$_{1-3}$alkyl or OC$_{1-3}$alkyl groups.

11. A compound in accordance with claim 1 or a pharmaceutically acceptable salt thereof, wherein:

R$^2$ is selected from the group consisting of C$_{1-4}$alkyl, cyclopropyl, cyclohexyl, OC$_{1-6}$alkyl and O-phenyl, the phenyl portion of which being optionally substituted with 1-3 halo groups selected from chloro and fluoro, and 0-1 C$_{1-3}$alkyl, haloC$_{1-3}$alkyl, C$_{1-3}$alkoxy or haloC$_{1-3}$alkoxy groups, wherein the halo atoms are fluorine or chlorine, and each of said C$_{1-4}$alkyl, cyclopropyl, cyclohexyl and OC$_{1-6}$alkyl being optionally substituted with 1-3 fluoro or chloro groups, and 0-1 members selected from the group consisting of OH, oxo, CN, OCH$_3$, OCF$_3$, C(O)CH$_3$, phenyl, and C(O)phenyl, said phenyl and the phenyl portion of C(O)phenyl being optionally substituted with 1-3 chlorine or fluorine atoms, and 1-2 CH$_3$ or OCH$_3$ groups.

12. A compound in accordance with claim 1 or a pharmaceutically acceptable salt thereof, wherein:

R$^1$ represents a member selected from the group consisting of phenyl pyridyl, pyrimidinyl and pyrazinyl; optionally substituted with 1-2 halo atoms selected from fluoro, chloro and bromo, wherein said phenyl pyridyl, pyrimidinyl or pyazinyl is substituted with 1-2 members selected from the group consisting of:

(1) C$_{1-3}$alkyl or C$_{3-6}$cycloalkyl, substituted with 1 member selected from the group consisting of:

i) S(O)$_x$C$_{1-3}$alkyl, wherein x is 0 or 2 and the alkyl portion is optionally substituted with 1-3 fluorine atoms; and ii) C(O)NR$^d$R$^e$ or NR$^d$C(O)R$^e$, wherein R$^d$ is selected from H and methyl, and R$^e$ is selected from H, methyl, C$_{3-6}$cycloalkyl, phenyl and a 5-6 membered heteroaryl group selected from thiazole, imidazole and triazole;

(2) S(O)$_x$C$_{1-3}$alkyl, and SO$_2$NR$^d$R$^e$ wherein x is 0, 1 or 2, R$^d$ and R$^e$ are as defined above and the C$_{1-3}$alkyl portion is optionally substituted with 1-3 halo groups selected from Cl and F; and (3) C(O)NR$^d$R$^e$ or NR$^d$C(O)R$^e$ wherein R$^d$ and R$^e$ are defined as above;

R$^2$ is selected from the group consisting of C$_{1-7}$alkyl, C$_{3-6}$cycloalkyl, OC$_{1-6}$alkyl and O-phenyl, the phenyl portion of which being optionally substituted with 1-3 halo groups selected from chloro and fluoro, and 0-1 C$_{1-3}$alkyl, haloC$_{1-3}$alkyl, C$_{1-3}$alkoxy or haloC$_{1-3}$alkoxy groups, wherein the halo atoms are fluorine or chlorine, and each of said C$_{1-7}$alkyl, C$_{3-6}$cycloalkyl and OC$_{1-6}$alkyl being optionally substituted with 1-3 fluoro or chloro groups, and 0-1 members selected from the group consisting of OH, oxo, CN, OC$_{1-3}$alkyl, haloC$_{1-3}$alkoxy, C(O)C$_{1-3}$alkyl, phenyl, and C(O)phenyl, said phenyl and the phenyl portion of C(O)phenyl being optionally substituted with 1-3 chlorine or fluorine atoms, and 1-2 C$_{1-3}$alkyl or OC$_{1-3}$alkyl groups.

13. A compound in accordance with claim 1 or a pharmaceutically acceptable salt thereof wherein:

R$^1$ represents a member selected from the group consisting of phenyl pyridyl, pyrimidinyl and pyrazinyl, optionally substituted with 1-2 halo atoms selected from fluoro and chloro, wherein said phenyl, pyridyl, pyrimidinyl or pyrazinyl is substituted with 1-2 members selected from the group consisting of:

(1) CH$_3$ or cyclopropyl, substituted with 1 member selected from the group consisting of:

i) S(O)$_2$C$_{1-3}$alkyl, wherein the alkyl portion is optionally substituted with 1-3 fluorine atoms; and ii) C(O)NR$^d$R$^e$ or NR$^d$C(O)R$^e$, wherein R$^d$ is selected from H and methyl, and R$^e$ is selected from H, methyl, C$_{3-6}$cycloalkyl, phenyl and a 5-6 membered heteroaryl group selected from thiazole, imidazole and triazole;

(2) S(O)$_x$C$_{1-3}$alkyl, and SO$_2$NR$^d$R$^e$ wherein the x 0, 1,or 2, R$^d$ and R$^e$ are as defined above, and the C$_{1-3}$alkyl portion is optionally substituted with 1-3 halo groups selected from Cl and F; and (3) C(O)NR$^d$R$^e$ or NR$^d$C(O)R$^e$ wherein R$^d$ and R$^e$ are as defined above;

R$^2$ is selected from the group consisting of C$_{1-4}$alkyl, cyclopropyl, cyclohexyl, OC$_{1-6}$alkyl and O-Phenyl, the phenyl portion of which being optionally substituted with 1-3 halo groups selected from chloro and fluoro, and 0-1 C$_{1-3}$alkyl, haloC$_{1-3}$alkyl, C$_{1-3}$alkoxy or haloC$_{1-3}$alkoxy groups, wherein the halo atoms are fluorine or chlorine, and each of said C$_{1-4}$alkyl, cyclopropyl, cyclohexyl and OC$_{1-6}$alkyl being optionally substituted with 1-3 fluoro or chloro groups, and 0-1 members selected from the group consisting of OH, oxo, CN, OCH$_3$, OCF$_3$, C(O)CH$_3$, phenyl, and C(O)phenyl, said phenyl and the phenyl portion of C(O)phenyl being optionally substituted with 1-3 chlorine or fluorine atoms, and 1-2 CH$_3$ or OCH$_3$ groups.

14. A compound in accordance with claim 1 which is:

tert-butyl 1'-[4-(methylsulfonyl)phenyl]-4,4'-bipiperidine-1-carboxylate;

tert-butyl 1'-{4-[(trifluoromethyl)sulfonyl]phenyl}-4,4'-bipiperidine-1-carboxylate;

tert-butyl 1'-{4-[(methylsulfonyl)methyl]phenyl}-4,4'-bipiperidine-1-carboxylate;

tert-butyl 1'-[6-(methylsulfonyl)pyrimidin-4-yl]-4,4'-bipiperidine-1-carboxylate;

tert-butyl 1'-[4-(methylthio)phenyl]-4,4'-bipiperidine-1-carboxylate;

tert-Butyl-1'-{4-[(1,2,4-thiadiazol-5-ylamino)carbonyl]phenyl}-4,4'-bipiperidine-1-carboxylate;

tert-butyl 1'-[4-(aminocarbonyl)phenyl]-4,4'-bipiperidine-1-carboxylate;

tert-butyl-1'-[4-(methylsulfinyl)phenyl]-4,4'-bipiperidine-1-carboxylate;

tert-butyl-1'-[4-(2-amino-2-oxoethyl)phenyl]-4,4'-bipiperidine-1-carboxylate;
tert-Butyl-1'-{4-[(1,3-thiazol-2-ylcarbonyl)amino]phenyl}-4,4'-bipiperidine-1-carboxylate;
tert-Butyl-1'-{4-[(1,3-thiazol-4-ylcarbonyl)amino]phenyl}-4,4'-bipiperidine-1-carboxylate;
tert-butyl-1'-{3-chloro-4-[(1,3-thiazol-4-ylcarbonyl)amino]phenyl}-4,4'-bipiperidine-1-carboxylate;
isobutyl 1'-[4-(methylsulfonyl)phenyl]-4,4'-bipiperidine-1-carboxylate;
4-methyl-1-{1'-[4-(methylsulfonyl)phenyl]-4,4'-bipiperidin-1-yl}-1-oxopentan-2-one;
or a pharmaceutically acceptable salt thereof.

15. A compound of claim 1 which is:
tert-butyl 1'-[2-flour-4-(methylsulfonyl)phenyl]-4,4'-bipiperidine-1-carboxylate;
tert-butyl 1'-[4-(methylsulfonyl)-2-(trifluoromethyl)phenyl]-4,4'-bipiperidine-1-carboxylate;
tert-butyl 1'-{4-[2-(methylsulfonyl)ethyl]phenyl}-4,4'-bipiperidine-1-carboxylate;
tert-butyl 1'-[3-chloro-4(methylsulfonyl)phenyl]-4,4'-bipiperidine-1-carboxylate;
tert-butyl 1'-{4-[(methylsulfonyl)methyl]phenyl}-4,4'-bipiperidine-1-carboxylate;
tert-butyl 1'-[2-(methylthio)pyrimidin-4-yl]-4,4'-bipiperidine-1-carboxylate;
tert-butyl 1'-[6-(methylsulfonyl)pyrimidin-4-yl]-4,4'-bipiperidine-1-carboxylate;
tert-butyl 1'-[4-(aminosulfonyl)phenyl]-4,4'-bipiperidine-1-carboxylate;
tert-butyl 1-{-4-[(methylamino)sulfonyl]phenyl}-4,4'-bipiperidine-1-carboxylate;
tert-butyl 1'-{4-[(dimethylamino)sulfonyl]phenyl}-4,4'-bipiperidine-1-carboxylate;
tert-butyl 1'-{3-chloro-4-[(dimethylamino)carbonyl]phenyl}-4,4'-bipiperidine-1-carboxylate;
tert-butyl 1'-{4-[(1,2,4-thiadizol-5-ylamino)carbonyl]phenyl}-4,4'-bipiperidine-1-carboxylate;
tert-butyl 1'-{4-[(1,3-thiazol-2-ylamino)carbonyl]phenyl}-4,4'-bipiperidine-1-carboxylate;
tert-butyl 1'-{4-[(1H-imidazol-2-ylamino)carbonyl]phenyl}-4,4'-bipiperidine-1-carboxylate;
tert-butyl 1'-{4-[(1H-1,2,4-triazol-3-ylamino)carbonyl]phenyl}-4,4'-bipiperidine-1-carboxylate;
tert-butyl 1'-{(3-chloro-4-[(1,3-thiazol-2-ylamino)carbonyl]phenyl}-4,4'-bipiperidine-1-carboxylate;
tert-butyl 1'-{3-flouro-4-[(1,3-thiazol-2-ylamino)carbonyl]phenyl}-4,4'-bipiperidine-1-carboxylate;
tert-butyl 1'-{3-flouro-4[(dimethylamino)carbonyl]phenyl}-4,4'-bipiperidine-1-carboxylate;
tert-butyl 1'-{4[(methylamino)carbonyl]phenyl}-4,4'-bipiperidine-1-carboxylate;
tert-butyl 1'-{4-[(dimethylamino)carbonyl]phenyl}-4,4'-bipiperidine-1-carboxylate;
tert-butyl 1'-(4-{[ethyl(methyl)amino]carbonyl}phenyl)-4,4'-bipiperidine-1-carboxylate;
tert-butyl 1'-{3-[(1,3-thiazol-2-ylamino)carbonyl]phenyl}-4,4'-bipiperidine-1-carboxylate;
tert-butyl 1'-[6-(methylthio)-3-pyridinyl]-4,4'-bipiperidine-1-carboxylate;
isopropyl 1'-[4-(methylsulfonyl)phenyl]-4,4'-bipiperidine-1-carboxylate;
isobutyl 1'-[2-fluoro-4-(methylsulfonyl)phenyl]-4,4'-bipiperidine-1-carboxylate;
propyl 1'-[4-(methylsulfonyl)phenyl]-4,4'-bipiperidine-1-carboxylate;
phenyl 1'-[4-(methylsulfonyl)phenyl]-4,4'-bipiperidine-1-carboxyate;
methyl 1'-[4-(methylsulfonyl)phenyl]-4,4'-bipiperidine-1-carboxylate;
ethyl 1'-[4-(methylsulfonyl)phenyl]-4,4'-bipiperidine-1-carboxylate;
4-methoxyphenyl 1'-[4-(methylsulfonyl)phenyl]4,4'-bipiperidine-1-carboxylate;
2,2-dimethylpropyl 1'-[4-(methylsulfonyl)phenyl]-4,4'-bipiperidine-1-carboxylate;
1-butyryl-1'-[4-(methylsulfonyl)phenyl]-4,4'-bipiperidine;
1-(2,2-dimethylpropanoyl)-1'[4-(methylsulfonyl)phenyl]-4,4'-bipiperidine;
1-(3-methylbutanoyl)-1'-[4-(methylsulfonyl)phenyl]-4,4'-bipiperidine;
1-(cyclohexylcarbonyl)-1'-[4-(methylsulfonyl)phenyl]-4,4'-bipiperidine;
1-[4-(methylsulfonyl)phenyl]-1'-(phenylacety)-4,4'-bipiperidine;
1-[methoxy(phenyl)acetyl]-1'-[4-(methylsulfonyl)phenyl]-4,4'-bipiperidine;
4-methyl-1-{1'-[4-(methylsulfonyl)phenyl]-4,4'-bipiperidin-1-yl}-1-oxopentan-2-ol;
4-methyl-1-{1'-[4-(methylsulfonyl)phenyl]-4,4'-bipiperidin-1-yl}-1-oxoperitan-2-one;
2-{1'-[4-(methylsulfonyl)phenyl]-4,4'-bipiperidin-1-yl}-2-oxo-1-phenylethanone;
2-{1'-[4-(methylsulfonyl)phenyl]-4,4'-bipiperidin-1-yl}-2-oxo-1-phenylethanol;
1{1'-[4-(methylsulftonyl)phenyl]-4,4'-bipiperidin-1-yl}-1-oxooctan-2-one;
(2S)-4-methyl-1-{1'-[4-(methylsulfonyl)phenyl]-4,4'-bipiperidin-1-yl}-1-oxopentan-2-ol;
1-[4-(methylsulfonyl)phenyl]-1'-{[1-(trifluoromethyl)cyclopropyl]carbonyl}-4,4'-bipiperidine;
3,3-dimethyl-1-{1'-[4-(methylsulfonyl)phenyl]-4,4'-bipiperidin-1-yl}-1-oxobutan-2-one;
1-({1'-[4-(methylsulfonyl)phenyl]-4,4'-bipiperidin-1-yl}carbonyl)cyclo propanecarbonitrile; or
1,1,1-trifluoro-3-{1'[4-(methylsulfonyl)phenyl]-4,4'-bipiperidin-1-yl}-3-oxoacetone;
or a pharmaceutically acceptable salt thereof.

16. A pharmaceutical composition comprised of a compound in accordance with claim 1 or a pharmaceutically acceptable salt thereof, in combination with a pharmaceutically acceptable carrier.

17. A method of treating hyperglycemia, diabetes or insulin resistance in a mammalian patient in need of such treatment which comprises administering to said patient a compound in accordance with claim 1 or a pharmaceutically acceptable salt thereof in an amount that is effective to treat hyperglycemia, diabetes or insulin resistance.

* * * * *